United States Patent
Goldhahn et al.

(10) Patent No.: US 11,351,223 B2
(45) Date of Patent: Jun. 7, 2022

(54) METHODS AND COMPOSITIONS FOR TREATMENT OF CARTILAGE DAMAGE AND ARTHRITIS

(71) Applicant: Novartis AG, Basel (CH)

(72) Inventors: Jörg Goldhahn, Walbach (CH); Kristen Johnson, Santee, CA (US); Celeste Scotti, Basel (CH); Igor Vostiar, Basel (CH)

(73) Assignee: Novartis AG, Basel (CH)

( * ) Notice: Subject to any disclaimer, the term of this patent is extended or adjusted under 35 U.S.C. 154(b) by 51 days.

(21) Appl. No.: 16/349,435

(22) PCT Filed: Nov. 13, 2017

(86) PCT No.: PCT/IB2017/057081
§ 371 (c)(1),
(2) Date: May 13, 2019

(87) PCT Pub. No.: WO2018/087727
PCT Pub. Date: May 17, 2018

(65) Prior Publication Data
US 2019/0269754 A1    Sep. 5, 2019

Related U.S. Application Data

(60) Provisional application No. 62/421,534, filed on Nov. 14, 2016, provisional application No. 62/560,301, filed on Sep. 19, 2017.

(51) Int. Cl.
*A61K 38/17* (2006.01)
*A61K 9/00* (2006.01)
*A61P 19/02* (2006.01)

(52) U.S. Cl.
CPC ........... *A61K 38/17* (2013.01); *A61K 9/0019* (2013.01); *A61P 19/02* (2018.01)

(58) Field of Classification Search
CPC ............................. A61K 38/17; A61P 19/02
See application file for complete search history.

(56) References Cited

U.S. PATENT DOCUMENTS

2014/0256643 A1* 9/2014 Johnson .............. A61K 31/728
514/17.1

FOREIGN PATENT DOCUMENTS

| WO | 2011/008773 A2 | 1/2011 |
| WO | 2014/138687 A1 | 9/2014 |

OTHER PUBLICATIONS

Lai Dar-Ming et al., Angiopoietin-Like Protein 1 Expression Is Related to Intermuscular Connective Tissue and Cartilage Development; Developmental Dynamics 236:2643-2652; Sep. 1, 2007.

\* cited by examiner

*Primary Examiner* — Xiaozhen Xie
(74) *Attorney, Agent, or Firm* — Seth E. Cockrum

(57) ABSTRACT

The invention provides methods and compositions for the treatment of cartilage damage or arthritis by administration of a protease-resistant ANGPTL3 polypeptide with chondrogenic activity.

15 Claims, 1 Drawing Sheet
Specification includes a Sequence Listing.

| Screening/Baseline/ Randomisation 14 Days | Cohort 1 4 patients* 0.2 mg/knee i.a. 7 days pre-TKR** | End of Study 28 Days post TKR Surgery |
|---|---|---|
| Screening/Baseline/ Randomisation 14 Days | Cohort 2 4 patients* 2 mg/knee i.a. 7 days pre-TKR** | End of Study 28 Days post TKR Surgery |
| Screening/Baseline/ Randomisation 14 Days | Cohort 3 4 patients* 10 mg/knee i.a. 7 days pre-TKR** | End of Study 28 Days post TKR Surgery |
| Screening/Baseline/ Randomisation 14 Days | Cohort 4 4 patients* 20 mg/knee i.a. 7 days pre-TKR** | End of Study 28 Days post TKR Surgery |
| Screening/Baseline/ Randomisation 14 Days | Cohort 5 4 patients* 20 mg/knee i.a. 2 hours pre-TKR** | End of Study 28 Days post TKR Surgery |
| Screening/Baseline/ Randomisation 14 Days | Cohort 6 4 patients* 20 mg/knee i.a. 21 days pre-TKR** | End of Study 28 Days post TKR Surgery |
| Screening/Baseline/ Randomisation 14 Days | Cohort 7 4 patients* 40 mg/knee i.a. 7 days pre-TKR** | End of Study 28 Days post TKR Surgery |

METHODS AND COMPOSITIONS FOR TREATMENT OF CARTILAGE DAMAGE AND ARTHRITIS

SEQUENCE LISTING

The instant application contains a Sequence Listing which has been submitted electronically in ASCII format and is hereby incorporated by reference in its entirety. Said ASCII copy, created on Oct. 26, 2017, is named PAT057513-WO-PCT_SL.txt and is 95,244 bytes in size.

TECHNICAL FIELD

The present invention relates to methods and compositions for the treatment of cartilage damage (e.g., articular cartilage damage) or arthritis.

BACKGROUND

Osteoarthritis (OA) represents the most common musculoskeletal disorder. Approximately 40 million Americans are currently affected; a number predicted to increase to 60 million within the next twenty years as a result of aging population and an increase in life expectancy, making it the fourth leading cause of disability. OA is characterized by a slow degenerative breakdown of a joint including both articular cartilage (containing the cells and matrix which produce lubrication and cushioning for the joint) and subchondral bone underlying the articular cartilage. OA can be considered a consequence of various etiologic factors. For example, it can be caused by abnormal biomechanical stress or genetic or acquired abnormalities of articular cartilage or bone.

Joint damage, e.g., acute joint injury, such as a meniscal or ligament tear, or an intra-articular fracture can also lead to arthritis, e.g., posttraumatic arthritis. Because articular cartilage has a limited ability to repair, even small undetectable damage can often get worse over time and lead to OA.

Though surgical techniques, and regenerative technology have made some progress in restoration of cartilage, slowing degeneration, and improved repair of joint damage, e.g., articular cartilage damage, a continued need exists for improvement of compositions and methods for cartilage regeneration, treatment of joint damage, e.g., articular cartilage damage, or OA.

SUMMARY OF THE INVENTION

The present invention provides methods and compositions for the treatment of arthritis or cartilage damage (e.g., articular cartilage damage) in a subject (e.g., a human subject) by administration to a joint of the subject an intra-articular dose of a protease resistant ANGPTL3 polypeptide with chondrogenic activity.

Provided herein are methods of treating arthritis or cartilage damage in a human subject by administering to a joint of the human subject an intra-articular dose of about 0.2-200 mg of a polypeptide comprising an amino acid sequence having at least 95% sequence identity to an amino acid sequence listed in Table 1, wherein the polypeptide comprises an amino acid that is a polar amino acid other than K or R at position 423, as determined with reference to SEQ ID NO:1, and the polypeptide has chondrogenic activity. In some embodiments, the human subject has cartilage damage. In some embodiments, the human subject has osteoarthritis, trauma arthritis, or autoimmune arthritis.

In some embodiments, the amino acid in the polypeptide corresponding to position 423 of SEQ ID NO: 1 is Q or S or deleted. In some embodiments, the polypeptide comprises an amino acid sequence listed in Table 1. In some embodiments, the polypeptide consists of an amino acid sequence listed in Table 1.

In some embodiments, provided herein are methods of treating arthritis or cartilage damage in a human subject by administering to a joint of the human subject an intra-articular dose of about 0.2-200 mg of a polypeptide comprising SEQ ID NO: 17. In some embodiments, provided herein are methods of treating arthritis or cartilage damage in a human subject by administering to a joint of the human subject an intra-articular dose of about 0.2-200 mg of a polypeptide consisting of SEQ ID NO: 17.

In some embodiments, the intra-articular dose of the ANGPTL3 polypeptide is about 0.2-100 mg. In some embodiments, the intra-articular dose of the ANGPTL3 polypeptide is about 0.2-60 mg. In some embodiments, the intra-articular dose of the ANGPTL3 polypeptide is about 0.2-40 mg. In some embodiments, the intra-articular dose of the ANGPTL3 polypeptide is about 2-40 mg. In some embodiments, the intra-articular dose of the ANGPTL3 polypeptide is about 10-40 mg. In some embodiments, the intra-articular dose of the ANGPTL3 polypeptide is about 20-40 mg. In some embodiments, the intra-articular dose of the ANGPTL3 polypeptide is about 40-60 mg. In some embodiments, the intra-articular dose of the ANGPTL3 polypeptide is about 0.2 mg. In some embodiments, the intra-articular dose of the ANGPTL3 polypeptide is about 2 mg. In some embodiments, the intra-articular dose of the ANGPTL3 polypeptide is about 10 mg. In some embodiments, the intra-articular dose of the ANGPTL3 polypeptide is about 20 mg. In some embodiments, the intra-articular dose of the ANGPTL3 polypeptide is about 40 mg. In some embodiments, the intra-articular dose of the ANGPTL3 polypeptide is about 60 mg.

In some embodiments, the ANGPTL3 polypeptide is administered to the joint of the subject in a single injection. In some embodiments, the ANGPTL3 polypeptide is administered to the joint of the subject in multiple injections. In some embodiments, the ANGPTL3 polypeptide is administered once every two weeks for a time period sufficient to treat the arthritis or cartilage damage. In some embodiments, the ANGPTL3 polypeptide is administered monthly for a time period sufficient to treat the arthritis or cartilage damage. In some embodiments, the ANGPTL3 polypeptide is administered weekly for a time period sufficient to treat the arthritis or cartilage damage.

In some embodiments, the methods further comprise performing a surgical procedure to an affected joint in the subject. The polypeptide can be administered before, during or after the surgical procedure.

In some embodiments, the methods further comprise an additional procedure. For example, the polypeptide or composition can be administered in conjunction with any one of bone marrow stimulation, cartilage replacement, autologous chondrocyte implantation (ACI), or matrix-induced autologous chondrocyte implantation (MACI). In some embodiments, the polypeptide or composition can be administered in conjunction with ACI.

Also provided herein are compositions comprising about 0.2-200 mg of a polypeptide comprising an amino acid sequence having at least 95% sequence identity to an amino acid sequence listed in Table 1, wherein the polypeptide comprises an amino acid that is a polar amino acid other than K or R at position 423, as determined with reference to SEQ ID NO:1, for use in the treatment of arthritis or cartilage damage in a human subject, wherein the polypeptide is administered intra-articularly. The arthritis can be osteoarthritis, trauma arthritis, or autoimmune arthritis.

In some embodiments, the amino acid in the polypeptide corresponding to position 423 of SEQ ID NO: 1 is Q or S or deleted. In some embodiments, the polypeptide comprises an amino acid sequence listed in Table 1. In some embodiments, the polypeptide consists of an amino acid sequence listed in Table 1.

In some embodiments, provided herein are compositions comprising about 0.2-200 mg of a polypeptide comprising SEQ ID NO: 17, for use in the treatment of arthritis or cartilage damage in a human subject, wherein the polypeptide is administered intra-articularly. In some embodiments, provided herein are compositions comprising about 0.2-200 mg of a polypeptide consisting of SEQ ID NO: 17, for use in the treatment of arthritis or cartilage damage in a human subject, wherein the polypeptide is administered intra-articularly.

In some embodiments, provided herein are compositions comprising about 0.2-60 mg (e.g., about 0.2-60 mg, about 0.2-55 mg, about 0.2-50 mg, about 0.2-45 mg, about 0.2-40 mg, about 0.2-35 mg, about 0.2-30 mg, about 0.2-25 mg, about 0.2-20 mg, about 0.2-15 mg, about 0.2-10 mg, about 0.2-5 mg, about 0.2-2 mg, about 2-60 mg, about 2-55 mg, about 2-50 mg, about 2-45 mg, about 2-40 mg, about 2-35 mg, about 2-30 mg, about 2-25 mg, about 2-20 mg, about 2-15 mg, about 2-10 mg, about 2-5 mg, about 5-60 mg, about 5-55 mg, about 5-50 mg, about 5-45 mg, about 5-40 mg, about 5-35 mg, about 5-30 mg, about 5-25 mg, about 5-20 mg, about 5-15 mg, about 5-10 mg, about 10-60 mg, about 10-55 mg, about 10-50 mg, about 10-45 mg, about 10-40 mg, about 10-35 mg, about 10-30 mg, about 10-25 mg, about 10-20 mg, about 10-15 mg, about 15-60 mg, about 15-55 mg, about 15-50 mg, about 15-45 mg, about 15-40 mg, about 15-35 mg, about 15-30 mg, about 15-25 mg, about 15-20 mg, about 20-60 mg, about 20-55 mg, about 20-50 mg, about 20-45 mg, about 20-40 mg, about 20-35 mg, about 20-30 mg, about 20-25 mg, about 25-60 mg, about 25-55 mg, about 25-50 mg, about 25-45 mg, about 25-40 mg, about 25-35 mg, about 25-30 mg, about 30-60 mg, about 30-55 mg, about 30-50 mg, about 30-45 mg, about 30-40 mg, about 30-35 mg, about 35-60 mg, about 35-55 mg, about 35-50 mg, about 35-45 mg, about 35-40 mg, about 40-60 mg, about 40-55 mg, about 40-50 mg, about 40-45 mg, about 45-60 mg, about 45-55 mg, about 45-50 mg, about 50-60 mg, about 50-55 mg, about 55-60 mg, about 0.2 mg, about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg) of a polypeptide comprising SEQ ID NO: 17, for use in the treatment of arthritis or cartilage damage in a human subject, wherein the polypeptide is administered intra-articularly.

In some embodiments, provided herein are compositions comprising about 0.2-60 mg (e.g., about 0.2-60 mg, about 0.2-55 mg, about 0.2-50 mg, about 0.2-45 mg, about 0.2-40 mg, about 0.2-35 mg, about 0.2-30 mg, about 0.2-25 mg, about 0.2-20 mg, about 0.2-15 mg, about 0.2-10 mg, about 0.2-5 mg, about 0.2-2 mg, about 2-60 mg, about 2-55 mg, about 2-50 mg, about 2-45 mg, about 2-40 mg, about 2-35 mg, about 2-30 mg, about 2-25 mg, about 2-20 mg, about 2-15 mg, about 2-10 mg, about 2-5 mg, about 5-60 mg, about 5-55 mg, about 5-50 mg, about 5-45 mg, about 5-40 mg, about 5-35 mg, about 5-30 mg, about 5-25 mg, about 5-20 mg, about 5-15 mg, about 5-10 mg, about 10-60 mg, about 10-55 mg, about 10-50 mg, about 10-45 mg, about 10-40 mg, about 10-35 mg, about 10-30 mg, about 10-25 mg, about 10-20 mg, about 10-15 mg, about 15-60 mg, about 15-55 mg, about 15-50 mg, about 15-45 mg, about 15-40 mg, about 15-35 mg, about 15-30 mg, about 15-25 mg, about 15-20 mg, about 20-60 mg, about 20-55 mg, about 20-50 mg, about 20-45 mg, about 20-40 mg, about 20-35 mg, about 20-30 mg, about 20-25 mg, about 25-60 mg, about 25-55 mg, about 25-50 mg, about 25-45 mg, about 25-40 mg, about 25-35 mg, about 25-30 mg, about 30-60 mg, about 30-55 mg, about 30-50 mg, about 30-45 mg, about 30-40 mg, about 30-35 mg, about 35-60 mg, about 35-55 mg, about 35-50 mg, about 35-45 mg, about 35-40 mg, about 40-60 mg, about 40-55 mg, about 40-50 mg, about 40-45 mg, about 45-60 mg, about 45-55 mg, about 45-50 mg, about 50-60 mg, about 50-55 mg, about 55-60 mg, about 0.2 mg, about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg) of a polypeptide consisting of SEQ ID NO: 17, for use in the treatment of arthritis or cartilage damage in a human subject, wherein the polypeptide is administered intra-articularly.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1 shows the study design of a randomized, placebo controlled, double-blind first-in-human single ascending dose study of ANGPTL3 polypeptide of SEQ ID NO: 17 in primary osteoarthritis patients scheduled for total knee replacement.

DETAILED DESCRIPTION

The present invention provides methods and compositions for the treatment of arthritis or cartilage damage (e.g., articular cartilage damage) in a subject (e.g., a human subject) by administration to a joint of the subject an intra-articular dose of a protease resistant ANGPTL3 polypeptide with chondrogenic activity.

DEFINITIONS

One skilled in the art will recognize many methods and materials similar or equivalent to those described herein, which could be used in the practice of the present invention. Indeed, the present invention is in no way limited to the methods and materials described.

As used herein, the singular forms "a," "an," and "the" include plural referents unless the context clearly dictates otherwise.

It is to be understood, although not always explicitly stated, that all numerical designations are preceded by the term "about." Accordingly, unless indicated to the contrary, the numerical parameters set forth in the specification and claims are approximations that may vary depending upon the desired properties sought to be obtained by the present disclosure. The term "about", when referring to a measurable value is meant to encompass variations of +/−10%, more preferably +/−5%, even more preferably +/−1%, and still more preferably +/−0.1% from a specified value. For example, the term "about" when referring to pH is meant to encompass variations of +/−0.3 of a specified pH value.

"ANGPTL3" refers to Angiopoietin-like 3, which is a member of the angiopoietin-like family of secreted factors. It is predominantly expressed in the liver, and has the characteristic structure of angiopoietins, consisting of a signal peptide, N-terminal coiled-coil domain (CCD) and the C-terminal fibrinogen (FBN)-like domain. ANGPTL3 was shown to bind αV/β3 integrins and FBN-like domain alone was sufficient to induce endothelial cell adhesion and in vivo angiogenesis (Camenisch et al., *J. Biol. Chem.* 277: 17281-17290, 2002). Endogenous ANGPTL3 is generally cleaved in vivo into amino-terminal and carboxyl-terminal fragments.

An amino acid sequence of ANGPTL3 (GenBank Accession No. NP_055310.1) is set forth in SEQ ID NO:1; and the corresponding polynucleotide sequence of which is set forth as SEQ ID NO: 2 (NCBI reference sequence number NM_014495.3).

```
Angiopoietin-related protein 3 preproprotein [Homo sapiens,
NP_055310.1]
                                                         (SEQ ID NO: 1)
MFTIKLLLFIVPLVISSRIDQDNSSFDSLSPEPKSRFAMLDDVKILANGLLQLGHGLKD

FVHKTKGQINDIFQKLNIFDQSFYDLSLQTSEIKEEEKELRRTTYTKLQVKNEEVKNMS

LELNSKLESLLEEKILLQQKVKYLEEQLTNLIQNQPETPEHPEVTSLKTFVEKQDNSIK

DLLQTVEDQYKQLNQQHSQIKEIENQLRRTSIQEPTEISLSSKPRAPRTTPFLQLNEIRN

VKHDGIPAECTTIYNRGEHTSGMYAIRPSNSQVFHVYCDVISGSPWTLIQFLRIDGSQN

FNEWENYKYGFGRLDGEFWLGLEKIYSIVKQSNYVLRIELEDWKDNKHYIEYSFYL

GNHETNYTLHLVAITGNVPNAIPENKDLVFSTWDHKAKGHFNCPEGYSGGWWWHD

ECGENNLNGKYNKPRAKSKPERRRGLSWKSQNGRLYSIKSTKMLIHPTDSESFE

Homo sapiens angiopoietin like 3 (ANGPTL3), cDNA [NM_014495.3]
                                                         (SEQ ID NO: 2)
    1 atatatagag ttaagaagtc taggtctgct tccagaagaa aacagttcca cgttgcttga 61 aattgaaaat caagataaaa atgttcacaa ttaagctcct tcttttattt gttcctctag 121 ttatttcctc cagaattgat caagacaatt catcatttga ttctctatct ccagagccaa 181 aatcaagatt tgctatgtta gacgatgtaa aaattttagc caatggcctc cttcagttgg 241 gacatggtct taaagacttt gtccataaga cgaagggcca aattaatgac atatttcaaa 301 aactcaacat atttgatcag tcttttatg atctatcgct gcaaaccagt gaaatcaaag 361 aagaagaaaa ggaactgaga agaactacat ataaactaca agtcaaaaat gaagaggtaa 421 agaatatgtc acttgaactc aactcaaaac ttgaaagcct cctagaagaa aaaattctac 481 ttcaacaaaa agtgaaatat ttagaagagc aactaactaa cttaattcaa aatcaacctg 541 aaactccaga acacccagaa gtaacttcac ttaaaacttt tgtagaaaaa caagataata 601 gcatcaaaga ccttctccag accgtggaag accaatataa acaattaaac caacagcata 661 gtcaaataaa agaaatagaa aatcagctca gaaggactag tattcaagaa cccacagaaa 721 tttctctatc ttccaagcca agagcaccaa gaactactcc ctttcttcag ttgaatgaaa 781 taagaaatgt aaaacatgat ggcattcctg ctgaatgtac caccatttat aacagaggtg
```

-continued

```
 841 aacatacaag tggcatgtat gccatcagac ccagcaactc tcaagttttt catgtctact
 901 gtgatgttat atcaggtagt ccatggacat taattcaaca tcgaatagat ggatcacaaa
 961 acttcaatga aacgtgggag aactacaaat atggttttgg gaggcttgat ggagaatttt
1021 ggttgggcct agagaagata tactccatag tgaagcaatc taattatgtt ttacgaattg
1081 agttggaaga ctggaaagac aacaaacatt atattgaata ttcttttttac ttgggaaatc
1141 acgaaaccaa ctatacgcta catctagttg cgattactgg caatgtcccc aatgcaatcc
1201 cggaaaacaa agatttggtg ttttctactt gggatcacaa agcaaaagga cacttcaact
1261 gtccagaggg ttattcagga ggctggtggt ggcatgatga gtgtggagaa acaacctaa
1321 atggtaaata taacaaacca agagcaaaat ctaagccaga gaggagaaga ggattatctt
1381 ggaagtctca aaatggaagg ttatactcta taaaatcaac caaaatgttg atccatccaa
1441 cagattcaga aagctttgaa tgaactgagg caaatttaaa aggcaataat ttaaacatta
1501 acctcattcc aagttaatgt ggtctaataa tctggtatta aatccttaag agaaagcttg
1561 agaaatagat ttttttttatc ttaaagtcac tgtctattta agattaaaca tacaatcaca
1621 taaccttaaa gaataccgtt tacatttctc aatcaaaatt cttataatac tatttgtttt
1681 aaattttgtg atgtgggaat caattttaga tggtcacaat ctagattata atcaataggt
1741 gaacttatta aataactttt ctaaataaaa aatttagaga cttttatttt aaaaggcatc
1801 atatgagcta atatcacaac tttcccagtt taaaaaaeta gtactcttgt taaaactcta
1861 aacttgacta aatacagagg actggtaatt gtacagttct taaatgttgt agtattaatt
1921 tcaaaactaa aaatcgtcag cacagagtat gtgtaaaaat ctgtaataca aattttaaa
1981 ctgatgcttc attttgctac aaaataattt ggagtaaatg tttgatatga tttatttatg
2041 aaacctaatg aagcagaatt aaatactgta ttaaaataag ttcgctgtct ttaaacaaat
2101 ggagatgact actaagtcac attgacttta acatgaggta tcactatacc ttatttgtta
2161 aaatatatac tgtatacatt ttatatattt taacacttaa tactatgaaa acaaataatt
2221 gtaaaggaat cttgtcagat tacagtaaga atgaacatat ttgtggcatc gagttaaagt
2281 ttatatttcc cctaaatatg ctgtgattct aatacattcg tgtaggtttt caagtagaaa
2341 taaacctcgt aacaagttac tgaacgttta aacagcctga caagcatgta tatatgttta
2401 aaattcaata aacaaagacc cagtccctaa attatagaaa tttaaattat tcttgcatgt
2461 ttatcgacat cacaacagat ccctaaatcc ctaaatccct aaagattaga tacaaatttt
2521 ttaccacagt atcacttgtc agaatttatt tttaaatatg atttttttaaa actgccagta
2581 agaaattta aattaaaccc atttgttaaa ggatatagtg cccaagttat atggtgacct
2641 acctttgtca atacttagca ttatgtattt caaattatcc aatatacatg tcatatatat
2701 ttttatatgt cacatatata aaagatatgt atgatctatg tgaatcctaa gtaaatattt
2761 tgttccagaa aagtacaaaa taataaaggt aaaaataatc tataattttc aggaccacag
2821 actaagctgt cgaaattaac gctgattttt ttagggccag aataccaaaa tggctcctct
2881 cttcccccaa aattggacaa tttcaaatgc aaaataattc attatttaat atatgagttg
2941 cttcctctat t
```

"ANGPTL3 polypeptide" refers to a naturally occurring ANGPTL3 protein or a fragment or variant thereof. For the purposes of the present disclosure, the numbering of an amino acid is typically determined with reference to the full-length wildtype human ANGPTL3 polypeptide sequence (SEQ ID NO:1). Thus, in embodiments in which a polypeptide of the invention contains only a C-terminal portion of full-length ANGPTL3, but not the N-terminal portion, although the peptide is less than 460 amino acids in length, the numbering of the positions is based on SEQ ID NO:1. For example, reference to position 423 of an ANGPTL3 polypeptide of the invention refers to position 423 of SEQ ID NO:1, even though the ANGPTL3 polypeptide of the invention itself may only be 200 amino acids in length. In determining an amino acid in a sequence of interest that "corresponds to" a position in a reference sequence, such as SEQ ID NO:1, this is performed by optimally aligning the sequences, e.g., using the default CLUSTAL alignment parameters or default BLAST 2 alignment parameters and comparing the sequences. For example, position 423 in a sequence of interest that is "determined with reference to SEQ ID NO:1", or an amino acid that "corresponds to" position 423 of SEQ ID NO:1, means the amino acid that aligns with position 423 of SEQ ID NO:1 when the sequence of interest is optimally aligned with SEQ ID NO:1.

The term "protease-resistant" as used herein refers to a polypeptide comprising a modification that renders the polypeptide less susceptible to cleavage by a trypsin-like protease than a corresponding non-modified wildtype polypeptide.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "variant" refers to a polypeptide that has a substantially identical amino acid sequence to a reference polypeptide, or is encoded by a substantially identical nucleotide sequence, and is capable of having one or more activities of the reference polypeptide. For example, a variant can have about 85%, 90%, 91%, 92%, 93%, 94%, 95%, 96%, 97%, 98%, 99% or higher sequence identity to a reference polypeptide, while retain one or more activities of the reference polypeptide.

The term "amino acid" refers to naturally occurring and synthetic amino acids, as well as amino acid analogs and amino acid mimetics that function in a manner similar to naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group. e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) as well as pyrrolysine, pyrroline-carboxyl-lysine, and selenocysteine.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations." which are one species of conservatively modified variations. Every polypeptide sequence herein which is encoded by a polynucleotide encompasses every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence. One of skill will recognize that individual substitutions, deletions or additions to a nucleic acid, peptide, polypeptide, or protein sequence which alters, adds or deletes a single amino acid or a small percentage of amino acids with reference to an original encoded amino acid sequence results in a "conservatively modified variant" where the alteration produces substitution of an amino acid with a chemically similar amino acid and/or a polypeptide sequence that produces a structurally similar protein having similar functional activity to the original protein. Conservative substitution tables providing functionally similar amino acids are well known in the art. Such conservatively modified variants are in addition to and do not exclude polymorphic variants, interspecies homologs, and alleles of the invention.

The term "conservative amino acid substitutions" refers to the substitution (conceptually or otherwise) of an amino acid from one such group with a different amino acid from the same group. One example of substitutions is based on analyzing the normalized frequencies of amino acid changes between corresponding proteins of homologous organisms (see, e.g., Schulz, G. E. and R. H. Schirmer, Principles of Protein Structure, Springer-Verlag). According to such analyses, groups of amino acids may be defined where amino acids within a group exchange preferentially with each other and, therefore, resemble each other most in their impact on the overall protein structure (see, e.g., Schulz, G. E. and R. H. Schirmer, Principles of Protein Structure, Springer-Verlag). One example of a set of amino acid groups defined in this manner include: (i) a charged group, consisting of Glu and Asp, Lys, Arg and His; (ii) a positively-charged group, consisting of Lys, Arg and His; (iii) a negatively-charged group, consisting of Glu and Asp; (iv) an aromatic group, consisting of Phe, Tyr and Trp; (v) a nitrogen ring group, consisting of His and Trp; (vi) a large aliphatic nonpolar group, consisting of Val, Leu and Ile; (vii) a slightly-polar group, consisting of Met and Cys; (viii) a small-residue group, consisting of Ser, Thr, Asp, Asn, Gly, Ala, Glu, Gln and Pro; (ix) an aliphatic group consisting of Val, Leu, Ile, Met and Cys; and (x) a small hydroxyl group consisting of Ser and Thr. Other examples of conservative substitutions based on shared physical properties are the substitutions within the following groups: 1) Alanine (A), Glycine (G); 2) Aspartic acid (D), Glutamic acid (E); 3)

Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. Percentage of "sequence identity" can be determined by comparing two optimally aligned sequences over a comparison window, where the fragment of the amino acid sequence in the comparison window may comprise additions or deletions (e.g., gaps or overhangs) as compared to the reference sequence (which does not comprise additions or deletions) for optimal alignment of the two sequences. The percentage can be calculated by determining the number of positions at which the identical amino acid residue occurs in both sequences to yield the number of matched positions, dividing the number of matched positions by the total number of positions in the window of comparison, and multiplying the result by 100 to yield the percentage of sequence identity. The output is the percent identity of the subject sequence with respect to the query sequence.

Two examples of algorithms that are suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands. The BLAST algorithm also performs a statistical analysis of the similarity between two sequences (see. e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "isolated," when applied to a nucleic acid or protein, denotes that the nucleic acid or protein is purified to be essentially free of other cellular components with which it is associated in the natural state. It is often in a homogeneous or nearly homogeneous state. It can be in either a dry or aqueous solution. Purity and homogeneity may be determined using analytical chemistry techniques known and used typically in the art, e.g., polyacrylamide gel electrophoresis, high performance liquid chromatography, etc. A protein that is the predominant species present in a preparation is substantially purified. The term "purified" in some embodiments denotes that a protein gives rise to essentially one band in an electrophoretic gel. Typically, it means that a protein is at least 85% pure, more preferably at least 95% pure, and most preferably at least 99% pure.

The term "subject" refers to an animal, human or non-human, to whom treatment according to the methods of the present invention is provided. Veterinary and non-veterinary applications are contemplated. The term includes, but is not limited to, mammals, e.g., humans, other primates, pigs, rodents such as mice and rats, rabbits, guinea pigs, hamsters, cows, horses, cats, dogs, sheep and goats. Typical subjects include humans, farm animals, and domestic pets such as cats and dogs.

The term "treat" or "treatment" refers to both therapeutic treatment and prophylactic or preventive measures, wherein the object is to prevent or slow down an undesired physiological change or disorder. For purpose of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable.

Protease-Resistant ANGPTL3 Polypeptides with Chondrogenic Activity

The present disclosure is directed to intra-articular administration to a subject (e.g., a human subject) of a protease-resistant ANGPTL3 polypeptide with chondrogenic activity for the treatment of cartilage damage (e.g., articular cartilage damage) or arthritis. Protease-resistant ANGPTL3 polypeptides with chondrogenic activities have been described in WO2014/138687, which is incorporated by reference in its entirety.

The ANGPTL3 polypeptides described herein have chondrogenic activity. As defined herein, chondrogenesis or chondrogenic activity refers to the development of chondrocytes from mesenchymal stem cells (MSCs). Mesenchymal stem cells (MSCs) are present in adult articular cartilage and upon isolation can be programmed in vitro to undergo differentiation to chondrocytes and other mesenchymal cell lineages, and may be used for cartilage regeneration. Indicators of chondrogenic activity include, but are not limited to, cartilage matrix production. Cartilage matrix production may be measured by various markers, for example, such as Sox9, type II collagen, or glycosaminoglycan (GAG) production. In some embodiments, type II collagen expression is measured as a marker for cartilage matrix production. In some embodiments, GAG production is measured as a marker for cartilage matrix production. In some embodiments, a 3-fold increase in GAG production with cartilage specific protein expression indicates positive cartilage matrix production.

The ANGPTL3 polypeptides described herein are protease resistant. A polypeptide may be evaluated for protease resistance using any known assay that measures cleavage by a serine protease such as trypsin. In some embodiments, the protease employed to evaluate proteolysis susceptibility is the serine protease trypsin. A polypeptide is considered to be protease-resistant if it has reduced sensitivity to trypsin when compared to its wild-type counterpart. An example of an assay is to measure the amount of cleaved product that is generated when a polypeptide is exposed to trypsin over a period of time in comparison to a corresponding native human peptide. Cleavage can be measured using any known assay, e.g., SDS PAGE or LCMS.

In an illustrative assay, limited proteolysis by trypsinolysis is performed by incubating 10 ng of the protein to be evaluated with trypsin at mass ratio of 8000:1 (Protein:Trypsin) for 1 hr at room temperature. The trypsinolysis reaction can then be quenched by addition of acetic acid to bring the reaction to pH 3.0. The quenched samples are then separated analyzed by SDS-PAGE, e.g., on a 4-12% Tris-Bis gel to identify proteins which are resistant to cleavage from those that are cleaved by the appearance of a fragment that is generated by trypsin cleavage. The cleavage product is absent or reduced in the protease-resistant polypeptides in comparison to their wildtype counterparts.

In some embodiments, the protease-resistant ANGPTL3 polypeptide comprises an amino acid sequence that has at least 95% identity, or at least 96%, 97%, 98%, or 99% identity, to an amino acid sequence listed in TABLE 1, wherein the polypeptide comprises an amino acid that is a polar amino acid other than K or R at position 423, as determined with reference to SEQ ID NO:1, and the polypeptide has chondrogenic activity. In some embodiments, the protease-resistant ANGPTL3 polypeptide comprises an amino acid sequence that has at least 95% identity, or at least 96%, 97%, 98%, or 99% identity, to an amino acid sequence listed in TABLE 1, wherein the amino acid residue corresponding to position 423 of SEQ ID NO: 1 is Q or S or deleted.

In some embodiments, the protease-resistant ANGPTL3 polypeptide comprises an amino acid sequence that has at least 95% identity, or at least 96%, 97%, 98%, or 99% identity, to an amino acid sequence selected from any one of SEQ ID NOs: 3-30, wherein the polypeptide comprises an amino acid that is a polar amino acid other than K or R at position 423, as determined with reference to SEQ ID NO:1, and the polypeptide has chondrogenic activity. In some embodiments, the protease-resistant ANGPTL3 polypeptide comprises an amino acid sequence that has at least 95% identity, or at least 96%/0, 97%, 98%, or 99% identity, to an amino acid sequence selected from any one of SEQ ID NOs: 3-30, wherein the amino acid residue corresponding to position 423 of SEQ ID NO: 1 is Q or S or deleted.

In a further embodiment, the protease-resistant ANGPTL3 polypeptide comprises an amino acid sequence that has at least 95% identity, or at least 96%, 97%, 98%, or 99% identity, to an amino acid sequence selected from any one of SEQ ID NOs: 3-18, wherein the polypeptide comprises an amino acid that is a polar amino acid other than K or R at position 423, as determined with reference to SEQ ID NO:1, and the polypeptide has chondrogenic activity. In some embodiments, the protease-resistant ANGPTL3 polypeptide comprises an amino acid sequence that has at least 95% identity, or at least 96%, 97%, 98%, or 99% identity, to an amino acid sequence selected from any one of SEQ ID NOs: 3-18, wherein the amino acid residue corresponding to position 423 of SEQ ID NO: 1 is Q or S or deleted.

In a further embodiment, the protease-resistant ANGPTL3 polypeptide comprises an amino acid sequence that has at least 95% identity, or at least 96%, 97%, 98%, or 99% identity, to SEQ ID NO: 17, wherein the polypeptide comprises an amino acid that is a polar amino acid other than K or R at position 423, as determined with reference to SEQ ID NO:1, and the polypeptide has chondrogenic activity. In a further embodiment, the protease-resistant ANGPTL3 polypeptide comprises an amino acid sequence that has at least 95% identity, or at least 96%, 97%, 98%, or 99% identity, to SEQ ID NO: 17, wherein the amino acid residue corresponding to position 423 of SEQ ID NO: 1 is Q or S or deleted.

In some embodiments, the protease-resistant ANGPTL3 polypeptide comprises an amino acid sequence selected from any one of the sequences listed in TABLE 1. In some embodiments, the protease-resistant ANGPTL3 polypeptide comprises an amino acid sequence selected from any one of SEQ ID NOs: 3-30. In some embodiments, the protease-resistant ANGPTL3 polypeptide comprises an amino acid sequence selected from any one of SEQ ID NOs: 3-18. In some embodiments, the protease-resistant ANGPTL3 polypeptide comprises SEQ ID NO: 17. In some embodiments, the protease-resistant ANGPTL3 polypeptide comprises SEQ ID NO: 18. In some embodiments, the protease-resistant ANGPTL3 polypeptide comprises SEQ ID NO: 37.

In some embodiments, the protease-resistant ANGPTL3 polypeptide consists of an amino acid sequence selected from any one of the sequences listed in TABLE 1. In some embodiments, the protease-resistant ANGPTL3 polypeptide consists of an amino acid sequence selected from any one of SEQ ID NOs: 3-30. In some embodiments, the protease-resistant ANGPTL3 polypeptide consists of an amino acid sequence selected from any one of SEQ ID NOs: 3-18. In some embodiments, the protease-resistant ANGPTL3 polypeptide consists of SEQ ID NO: 17. In some embodiments, the protease-resistant ANGPTL3 polypeptide consists of SEQ ID NO: 18. In some embodiments, the protease-resistant ANGPTL3 polypeptide consists of SEQ ID NO: 37.

TABLE 1

ANGPTL3 variant constructs

| SEQ ID NO | Construct | Sequence |
|---|---|---|
| 3 | 207KQ | IQEPTEISLSSKPRAPRTTPFLQLNEIRNVKHDGIPAECTTIYNRGEH TSGMYAIRPSNSQVFTIVYCDVISGSPWTLIQHRIDGSQNFNETWEN YKYGFGRLDGEFWLGLEKIYSIVKQSNYVLRIELEDWKDNKHYIE YSFYLGNHETNYTLHLVAITGNVPNAIPENKDLVFSTWDHKAKGH FNCPEGYSGGWWWHDECGENNLNGKYNKPRAQSKPERRRGLSW KSQNGRLYSTKSTKMLIHPTDSESFE |
| 4 | 207KS | IQEPTEISLSSKPRAPRTTPFLQLNEIRNVKHDGIPAECTTIYNRGEH TSGMYAIRPSNSQVFHVYCDVISGSPWTLIQHRIDGSQNFNETWEN YKYGFGRLDGEFWLGLEKIYSIVKQSNYVLRIELEDWKDNKHYIE YSFYLGNHETNYTLHLVAITGNVPNAIPENKDLVFSTWDHKAKGH FNCPEGYSGGWWWHDECGENNLNGKYNKPRASSKPERRRGLSW KSQNGRLYSIKSTKMLIHPTDSESFE |
| 5 | 225KQ | TTPFLQLNEIRNVKHDGTPAECTTIYNRGEHTSGMYAIRPSNSQVF HVYCDVISGSPWILIQHRIDGSQNFNETWENYKYGFGRLDGEFWL GLEKIYSIVKQSNYVLRIELEDWKDNKHYIEYSFYLGNHETNYTLH LVAITGNVPNAIPENKDLVFSTWDHKAKGHFNCPEGYSGGWWW HDECGENNLNGKYNKPRAQSKPERRRGLSWKSQNGRLYSIKSTK MLIHPTDSESFE |
| 6 | 225KS | TTPFLQLNEIRNVKHDGIPAECTTIYNRGEHTSGMYAIRPSNSQVF HVYCDVISGSPWTLIQHRIDGSQNFNETWENYKYGFGRLDGEFWL GLEKIYSIVKQSNYVLRIELEDWKDNKHYIEYSFYLGNHETNYTLH LVAITGNVPNAIPENKDLVFSTWDHKAKGHFNCPEGYSGGWWW HDECGENNLNGKYNKPRASSKPERRRGLSWKSQNGRLYSTKSTK MLIHPTDSESFE |
| 7 | 225ST | TTPFLQLNEIRNVKHDGIPAECTTIYNRGEHTSGMYAIRPSNSQVF HVYCDVISGSPWTLIQHRIDGSQNFNEWENYKYGFGRLDGEFWL GLEKIYSIVKQSNYVLRIELEDWKDNKHYIEYSFYLGNHETNYTLH LVAITGNVPNAIPENKDLVFSTWDHKAKGHFNCPEGYSGGWWW HDECGENNLNGKYNKPRAKTKPERRRGLSWKSQNGRLYSIKSTK MLIHPTDSESFE |
| 8 | 226KQ | TPFLQLNEIRNVKHDGIPAECTTIYNRGEHTSGMYAIRPSNSQVFH VYCDVISGSPWTLIQHRIDGSQNFNETWENYKYGFGRLDGEFWLG LEKIYSIVKQSNYVLRIELEDWKDNKHYIEYSFYLGNHETNYTLHL VAITGNVPNAIPENKDLVFSTWDHKAKGHFNCPEGYSGGWWWH DECGENNLNGKYNKPRAQSKPERRRGLSWKSQNGRLYSIKSTKM LIHPTDSESFE |
| 9 | 226KS | TPFLQLNEIRNVKHDGIPAECTTIYNRGEHTSGMYAIRPSNSQVFH VYCDVISGSPWTLIQHRIDGSQNFNETWENYKYGFGRLDGEFWLG LEKIYSIVKQSNYVLRIELEDWKDNKHYIEYSFYLGNHETNYTLHL VAITGNVPNAIPENKDLVFSTWDHKAKGHFNCPEGYSGGWWWH DECGENNLNGKYNKPRASSKPERRRGLSWKSQNGRLYSIKSTKM LIHPTDSESFE |
| 10 | 228KQ | FLQLNEIRNVKHDGIPAECTTIYNRGEHTSGMYAIRPSNSQVFKVY CDVISGSPWTLIQHRIDGSQNFNETWENYKYGFGRLDGEFWLGLE KIYSIVKQSNYVLRIELEDWKDNKHYIEYSFYLGNHETNYTLHLV AITGNVPNAIPENKDLVFSTWDHKAKGHFNCPEGYSGGWWWHD ECGENNLNGKYNKPRAQSKPERRRGLSWKSQNGRLYSIKSTKMLI HPTDSESFE |
| 11 | 228KS | FLQLNEIRNVKHDGIPAECTTIYNRGEHTSGMYAIRPSNSQVFHVY CDVISGSPWTLIQHRIDGSQNFNETWENYKYGFGRLDGEFWLGLE KIYSIVKQSNYVLRIELEDWKDNKHYIEYSFYLGNHETNYTLHLV AITGNVPNAIPENKDLVFSTWDHKAKGHFNCPEGYSGGWWWHD ECGENNLNGKYNKPRASSKPERRRGLSWKSQNGRLYSIKSTKMLI HPTDSESFE |
| 12 | 228ST | FLQLNEIRNVKHDGIPAECTTIYNRGEHTSGMYAIRPSNSQVFHVY CDVISGSPWTLIQHRIDGSQNFNETWENYKYGFGRLDGEFWLGLE KIYSIVKQSNYVLRIELEDWKDNKHYIEYSFYLGNHETNYTLHLV AITGNVPNAIPENKDLVFSTWDHKAKGHFNCPEGYSGGWWWHD ECGENNLNGKYNKPRAKTKPERRRGLSWKSQNGRLYSIKSTKMLI HPTDSESFE |
| 13 | 233KQ | EIRNVKHDGIPAECTTIYNRGEHTSGMYAIRPSNSQVFHVYCDVIS GSPWTLIQHRIDGSQNFNETWENYKYGFGRLDGEFWLGLEKIYSI VKQSNYYLRIELEDWKDNKHYIEYSFYLGNHETNYTLHLVAITGN |

TABLE 1-continued

ANGPTL3 variant constructs

| SEQ ID NO | Construct | Sequence |
|---|---|---|
| | | VPNAIPENKDLVFSTWDHKAKGHFNCPEGYSGGWWWHDECGEN NLNGKYNKPRAQSKPERRRGLSWKSQNGRLYSIKSTKMLIHPTDS ESFE |
| 14 | 233KS | EIRNVKHDGIPAECTTIYNRGEHTSGMYAIRPSNSQVFHVYCDVIS GSPWTLIQHRIDGSQNFNETWENYKYGFGRLDGEFWLGLEKIYSI VKQSNYVLRIELEDWKDNKHYIEYSFYLGNHETNYTLHLVAITGN VPNAIPENKDLVFSTWDHKAKGHFNCPEGYSGGWWWHDECGEN NLNGKYNKPRASSKPERRRGLSWKSQNGRLYSIKSTKMLIHPTDS ESFE |
| 15 | 241KQ | GIPAECTTIYNRGEHTSGMYAIRPSNSQVFHVYCDVISGSPWTLIQ HRIDGSQNFNETWENYKYGFGRLDGEFWLGLEKIYSIVKQSNYVL RIELEDWKDNKHYIEYSFYLGNHETNYTLHLVAITGNVPNAIPENK DLVFSTWDHKAKGHFNCPEGYSGGWWWHDECGENNLNGKYNK PRAQSKPERRRGLSWKSQNGRLYSIKSTKMLIHPTDSESFE |
| 16 | 241KS | GIPAECTTIYNRGEHTSGMYAIRPSNSQVFHVYCDVISGSPWTLIQ HRIDGSQNFNETWENYKYGFGRLDGEFWLGLEKIYSIVKQSNYVL RIELEDWKDNKHYIEYSFYLGNHETNYTLHLVAITGNVPNAIPENK DLVFSTWDHKAKGHFNCPEGYSGGWWWHDECGENNLNGKYNK PRASSKPERRRGLSWKSQNGRLYSIKSTKMLIHPTDSESFE |
| 17 | 242KQ | IPAECTTIYNRGEHTSGMYAIRPSNSQVFHYYCDVISGSPWTLIQHR IDGSQNFNETWENYKYGFGRLDGEFWLGLEKIYSIVKQSNYVLRI ELEDWKDNKHYIEYSFYLGNHETNYTLHLVAITGNVPNAIPENKD LVFSTWDHKAKGHFNCPEGYSGGWWWHDECGENNLNGKYNKP RAQSKPERRRGLSWKSQNGRLYSIKSTKMLIHPTDSESFE |
| 18 | 242KS | IPAECTTIYNRGEHTSGMYAIRPSNSQVFHVYCDVISGSPWTLIQHR IDGSQNFNETWENYKYGFGRLDGEFWLGLEKIYSIVKQSNYVLRI ELEDWKDNKHYIEYSFYLGNHETNYTLHLVAITGNVPNAIPENKD LVFSTWDHKAKGHFNCPEGYSGGWWWHDECGENNLNGKYNKP RASSKPERRRGLSWKSQNGRLYSIKSTKMLIHPTDSESFE |
| 19 | 225-455KQ | TTPFLQLNEIRNVKHDGIPAECTTIYNRGEHTSGMYAIRPSNSQVF HVYCDVISGSPWTLIQHRIDGSQNFNETWENYKYGFGRLDGEFWL GLEKIYSIVKQSNYVLRIELEDWKDNKHYIEYSFYLGNHETNYTLH LVAITGNVPNAIPENKDLVFSTWDHKAKGHFNCPEGYSGGWWW HDECGENNLNGKYNKPRAQSKPERRRGLSWKSQNGRLYSIKSTK MLIHPTD |
| 20 | 225-455KS | TTPFLQLNEIRNVKHDGIPAECTTIYNRGEHTSGMYAIRPSNSQVF HVYCDVISGSPWTLIQHRIDGSQNFNETWENYKYGFGRLDGEFWL GLEKIYSIVKQSNYVLRIELEDWKDNKHYIEYSFYLGNHETNYTLH LVAITGNVPNAIPENKDLVFSTWDHKAKGHFNCPEGYSGGWWW HDECGENNLNGKYNKPRASSKPERRRGLSWKSQNGRLYSIKSTK MLIHPTD |
| 21 | 226-455KQ | TPFLQLNEIRNVKHDGIPAECTTIYNRGEHTSGMYAIRPSNSQVFH VYCDVISGSPWTLIQHRIDGSQNFNETWENYKYGFGRLDGEFWLG LEKIYSIVKQSNYVLRIELEDWKDNKHYIEYSFYLGNHETNYTLHL VAITGNVPNAIPENKDLVFSTWDHKAKGHFNCPEGYSGGWWWH DECGENNLNGKYNKPRAQSKPERRRGLSWKSQNGRLYSIKSTKM LIHPTD |
| 22 | 226-455KS | TPFLQLNEIRNVKHDGIPAECTTIYNRGEHTSGMYAIRPSNSQVFH VYCDVISGSPWTLIQHRIDGSQNFNETWENYKYGFGRLDGEFWLG LEKIYSIVKQSNYVLRIELEDWKDNKHYIEYSFYLGNHETNYTLHL VAITGNVPNAIPENKDLVFSTWDHKAKGHFNCPEGYSGGWWWH DECGENNLNGKYNKPRASSKPERRRGLSWKSQNGRLYSIKSTKM LIHPTD |
| 23 | 228-455KQ | FLQLNEIRNVKHDGIPAECTTIYNRGEHTSGMYAIRPSNSQVFHVY CDVISGSPWTLIQHRIDGSQNFNETWENYKYGFGRLDGEFWLGLE KIYSIVKQSNYVLRIELEDWKDNKHYIEYSFYLGNHETNYTLHLV AITGNVPNAIPENKDLVFSTWDHKAKGHFNCPEGYSGGWWWHD ECGENNLNGKYNKPRAQSKPERRRGLSWKSQNGRLYSIKSTKMLI HPTD |

TABLE 1-continued

ANGPTL3 variant constructs

| SEQ ID NO | Construct | Sequence |
|---|---|---|
| 24 | 228-455KS | FLQLNEIRNVKHDGIPAECTTIYNRGEHTSGMYAIRPSNSQVFHVY CDVISGSPWTLIQHRIDGSQNFNETWENYKYGFGRLDGEFWLGLE KIYSIVKQSNYVLRIELEDWKDNKHYIEYSFYLGNHETNYTLHLV AITGNVPNAIPENKDLVFSTWDHKAKGHFNCPEGYSGGWWWHD ECGENNLNGKYNKPRASSKPERRRGLSWKSQNGRLYSIKSTKMLI HPTD |
| 25 | 233-455KQ | EIRNVKHDGIPAECTTIYNRGEHTSGMYAIRPSNSQVFHVYCDVIS GSPWTLIQHRIDGSQNFNETWENYKYGFGRLDGEFWLGLEKIYSI VKQSNYYLRIELEDWKDNKHYIEYSFYLGNHETNYTLHLVAITGN VPNAIPENKDLVFSWDHKAKGHFNCPEGYSGGWWWHDECGEN NLNGKYNKPRAQSKPERRRGLSWKSQNGRLYSIKSTKMLIHPTD |
| 26 | 233-455KS | EIRNVKHDGIPAECTTIYNRGEHTSGMYAIRPSNSQVFHVYCDVIS GSPWTLIQHRIDGSQNFNETWENYKYGFGRLDGEFWLGLEKIYSI VKQSNYVLRIELEDWKDNKHYIEYSFYLGNHETNYTLHLVAITGN VPNAIPENKDLVFSWDHKAKGHFNCPEGYSGGWWWHDECGEN NLNGKYNKPRASSKPERRRGLSWKSQNGRLYSIKSTKMLIHPTD |
| 27 | 241-455KQ | GIPAECTTIYNRGEHTSGMYAIRPSNSQVTHVYCDVISGSPWTLIQ HRIDGSQNFNETWENYKYGFGRLDGEFWLGLEKIYSIVKQSNYVL RIELEDWKDNKHYIEYSFYLGNHETNYTLHLVAITGNVPNAIPENK DLVFSTWDHKAKGHFNCPEGYSGGWWWHDECGENNLNGKYNK PRAQSKPERRRGLSWKSQNGRLYSIKSTKMLIHPTD |
| 28 | 241-455KS | GIPAECTTIYNRGEHTSGMYAIRPSNSQVFHVYCDVISGSPWTLIQ HRIDGSQNFNETWENYKYGFGRLDGEFWLGLEKIYSIVKQSNYVL RIELEDWKDNKHYIEYSFYLGNHETNYTLHLVAITGNVPNAIPENK DLVFSTWDHKAKGHFNCPEGYSGGWWWHDECGENNLNGKYNK PRASSKPERRRGLSWKSQNGRLYSIKSTKMLIHPTD |
| 29 | 242-455KQ | IPAECTTIYNRGEHTSGMYAIRPSNSQVFHVYCDVISGSPWTLIQHR IDGSQNFNETWENYKYGFGRLDGEFWLGLEKIYSIVKQSNYVLRT ELEDWKDNKHYIEYSFYLGNHETNYTLHLVAITGNVPNAIPENKD LVFSTWDHKAKGHFNCPEGYSGGWWWHDECGENNLNGKYNKP RAQSKPERRRGLSWKSQNGRLYSIKSTKMLIHPTD |
| 30 | 242-455KS | IPAECTTIYNRGEHTSGMYAIRPSNSQVFHVYCDVISGSPWTLIQHR IDGSQNFNETWENYKYGFGRLDGEFWLGLEKIYSIVKQSNYVLRI ELEDWKDNKHYIEYSFYLGNHETNYTLHLVAITGNVPNAIPENKD LVFSTWDHKAKGHFNCPEGYSGGWWWHDECGENNLNGKYNKP RASSKPERRRGLSWKSQNGRLYSIKSTKMLIHPTD |
| 31 | 207Kdel | IQEPTEISLSSKPRAPRTTPFLQLNEIRNVKHDGIPAECTTIYNRGEH TSGMYAIRPSNSQVFHVYCDVISGSPWTLIQHRIDGSQNFNETWEN YKYGFGRLDGEFWLGLEKIYSIVKQSNYVLRIELEDWKDNKHYIE YSFYLGNHETNYTLHLVAITGNVPNAIPENKDLVFSTWDHKAKGH FNCPEGYSGGWWWHDECGENNLNGKYNKPRASKPERRRGLSWK SQNGRLYSIKSTKMLIHPTDSESFE |
| 32 | 225Kdel | TTPFLQLNEIRNVKHDGIPAECTTIYNRGEHTSGMYAIRPSNSQVF HVYCDVISGSPWTLIQHRIDGSQNFNETWENYKYGFGRLDGEFWL GLEKIYSIVKQSNYVLRIELEDWKDNKHYIEYSFYLGNHETNYTLH LVAITGNVPNAIPENKDLVFSTWDHKAKGHFNCPEGYSGGWWW HDECGENNLNGKYNKPRASKPERRRGLSWKSQNGRLYSIKSTKM LIHPTDSESFE |
| 33 | 226Kdel | TPFLQLNEIRNVKHDGIPAECTTIYNRGEHTSGMYAIRPSNSQVFH VYCDVISGSPWTLIQHRIDGSQNFNETWENYKYGFGRLDGEFWLG LEKIYSIVKQSNYVLRIELEDWKDNKHYIEYSFYLGNHETNYTLHL VAITGNVPNAIPENKDLVFSTWDHKAKGHFNCPEGYSGGWWWH DECGENNLNGKYNKPRASKPERRRGLSWKSQNGRLYSIKSTKMLI HPTDSESFE |
| 34 | 228Kdel | FLQLNEIRNVKHDGIPAECTTIYNRGEHTSGMYAIRPSNSQVFKVY CDVISGSPWTLIQHRIDGSQNFNETWENYKYGFGRLDGEFWLGLE KIYSIVKQSNYVLRIELEDWKDNKHYIEYSFYLGNHETNYTLHLV AITGNVPNAIPENKDLVFSTWDHKAKGHFNCPEGYSGGWWWHD ECGENNLNGKYNKPRASKPERRRGLSWKSQNGRLYSIKSTKMLIH PTDSESFE |

TABLE 1-continued

ANGPTL3 variant constructs

| SEQ ID NO | Construct | Sequence |
|---|---|---|
| 35 | 233Kdel | EIRNVKHDGIPAECTTIYNRGEHTSGMYAIRPSNSQVFHVYCDVIS GSPWTLIQHRIDGSQNFNETWENYKYGFGRLDGEFWLGLEKIYSI VKQSNYVLRIELEDWKDNKHYIEYSFYLGNHETNYTLHLVAITGN VPNAIPENKDLVFSTWDHKAKGHFNCPEGYSGGWWWHDECGEN NLNGKYNKPRASKPERRRGLSWKSQNGRLYSIKSTKMLIHPTDSE SFE |
| 36 | 241Kdel | GIPAECTTIYNRGEHTSGMYAIRPSNSQVFHVYCDVISGSPWTLIQ HRIDGSQNFNETWENYKYGFGRLDGEFWLGLEKIYSIVKQSNYVL RIELEDWKDNKHYIEYSFYLGNHETNYTLHLVAITGNVPNAIPENK DLVFSTWDHKAKGHFNCPEGYSGGWWWHDECGENNLNGKYNK PRASKPERRRGLSWKSQNGRLYSIKSTKMLIHPTDSESFE |
| 37 | 242Kdel | IPAECTTIYNRGEHTSGMYAIRPSNSQVFHVYCDVISGSPWTLIQHR IDGSQNFNETWENYKYGFGRLDGEFWLGLEKIYSIVKQSNYVLRI ELEDWKDNKHYIEYSFYLGNHETNYTLHLVAITGNVPNAIPENKD LVFSTWDHKAKGHFNCPEGYSGGWWWHDECGENNLNGKYNKP RASKPERRRGLSWKSQNGRLYSIKSTKMLIHPTDSESFE |
| 38 | 225-455Kdel | TTPFLQLNEIRNVKHDGIPAECTTIYNRGEHTSGMYAIRPSNSQVF HVYCDVISGSPWTLIQHRIDGSQNFNETWENYKYGFGRLDGEFWL GLEKIYSIVKQSNYVLRIELEDWKDNKFSYIEYSFYLGNHETNYTLH LVAITGNVPNAIPENKDLVFSTWDHKAKGHFNCPEGYSGGWWW HDECGENNLNGKYNKPRASKPERRRGLSWKSQNGRLYSIKSTKM LIHPTD |
| 39 | 226-455Kdel | TPFLQLNEIRNVKHDGIPAECTTIYNRGEHTSGMYAIRPSNSQVFH VYCDVISGSPWTLIQHRIDGSQNFNETWENYKYGFGRLDGEFWLG LEKIYSIVKQSNYVLRIELEDWKDNKHYIEYSFYLGNHETNYTLHL VAITGNVPNAIPENKDLVFSTWDHKAKGHFNCPEGYSGGWWWH DECGENNLNGKYNKPRASKPERRRGLSWKSQNGRLYSIKSTKMLI HPTD |
| 40 | 228-455Kdel | FLQLNEIRNVKHDGIPAECTTIYNRGEHTSGMYAIRPSNSQVFHVY CDVISGSPWTLIQHRIDGSQNFNETWENYKYGFGRLDGEFWLG KIYSIVKQSNYVLRIELEDWKDNKHYIEYSFYLGNHETNYTLHLV AITGNVPNAIPENKDLVFSTWDHKAKGHFNCPEGYSGGWWWHD ECGENNLNGKYNKPRASKPERRRGLSWKSQNGRLYSIKSTKMLIH PTD |
| 41 | 233-455Kdel | EIRNVKHDGIPAECTTIYNRGEHTSGMYAIRPSNSQVFHVYCDVIS GSPWTLIQHRIDGSQNFNETWENYKYGFGRLDGEFWLGLEKIYSI VKQSNYVLRIELEDWKDNKHYIEYSFYLGNHETNYTLHLVAITGN VPNAIPENKDLVFSTWDHKAKGHFNCPEGYSGGWWWHDECGEN NLNGKYNKPRASKPERRRGLSWKSQNGRLYSIKSTKMLIHPTD |
| 42 | 241-455Kdel | GIPAECTTIYNRGEHTSGMYAIRPSNSQVFHVYCDVISGSPWTLIQ HRIDGSQNFNETWENYKYGFGRLDGEFWLGLEKIYSIVKQSNYVL RIELEDWKDNKHYIEYSFYLGNHETNYTLHLVAITGNVPNAIPENK DLVFSTWDHKAKGHFNCPEGYSGGWWWHDECGENNLNGKYNK PRASKPERRRGLSWKSQNGRLYSIKSTKMLIHPTD |
| 43 | 242-455Kdel | IPAECTTIYNRGEHTSGMYAIRPSNSQVFHVYCDVISGSPWTLIQHR IDGSQNFNETWENYKYGFGRLDGEFWLGLEKIYSIVKQSNYVLRI ELEDWKDNKHYIEYSFYLGNHETNYTLHLVAITGNVPNAIPENKD LVFSTWDHKAKGHFNCPEGYSGGWWWHDECGENNLNGKYNKP RASKPERRRGLSWKSQNGRLYSIKSTKMLIHPTD |

The ANGPTL3 polypeptides described herein can have at least one substitution or deletion in the C-terminal portion of the polypeptide to render the polypeptide protease resistant. The substitution or deletion is at an R or K residue so that polypeptides have increased resistance to proteases, e.g., to trypsin-like proteases. Any amino acid may be substituted for an R or K in a protease resistant ANGPTL3 polypeptide, or the R or K residue can be deleted. In some embodiments, a substitution is a polar amino acid, e.g., H, N, Q, S, T, A, or Y. In some embodiments, a substitution is H, N, Q, S, T, or Y. In some embodiments, a substitution is S or Q. In some embodiments, the substitution is Q. In some embodiments the substitution is S. In some embodiments, a protease-resistant ANGPTL3 peptide has an amino acid at position 423, with reference to SEQ ID NO:1, that is other than K or R. In some embodiments, a protease-resistant ANGPTL3 polypeptide comprises an amino acid at position 423 (with reference to SEQ ID NO:1) that is a polar amino acid, for example, the amino acid at position 423 (with reference to SEQ ID NO:1) may be Q or S or another polar amino acid. In certain embodiments, a protease-resistant ANGPTL3 polypeptide has a Q at position 423 (with reference to SEQ ID NO:1). In other embodiments, a protease-resistant ANGPTL3 polypeptide has an S at position 423 (with reference to SEQ ID NO:1). In some embodiments, in addition to substitution at 423 (with reference to SEQ ID NO:1), the protease-resistant ANGPTL3 peptide has a substitution of another R or K in the C-terminus of SEQ ID NO:1, or a variant thereof, wherein the substitution is a polar amino acid other than R or K. In some embodiments, the substitution at position 423 (with reference to SEQ ID NO:1) is Q or S in a protease-resistant ANGPTL3 peptide. In some embodiments, the amino acid corresponding to position 423 of SEQ ID NO: 1 is deleted in a protease-resistant ANGPTL3 peptide.

In some embodiments, the protease-resistant ANGPTL3 polypeptide is 250 amino acids or less in length and comprises an amino acid sequence selected from any one of SEQ ID NOs: 5-18.

In some embodiments, the protease-resistant ANGPTL3 polypeptide is a carboxyl-terminal (C-terminal) fragment (e.g., at least 100, 150, 200, 220 or 215 contiguous amino acids) of a human ANGPTL3 protein, or has a sequence substantially identical to the C-terminal fragment of human ANGPTL3 protein sequence, wherein the polypeptide retains chondrogenic activity. In some embodiments, the protease-resistant ANGPTL3 polypeptide lacks at least a portion of the C-terminal sequence, e.g., lacks 5, 10, 15, or 20 amino acids from the C-terminal end of SEQ ID NO:1 (i.e., lacks 456-460, 451-460, 446-460 or 441-460 of SEQ ID NO:1).

In some embodiments, a protease-resistant ANGPTL3 polypeptide comprises contiguous amino acids corresponding to the amino acid regions: amino acids 241-455, or 241-460 of SEQ ID NO:1; amino acids 242-455, or 242-460 of SEQ ID NO:1; amino acids 233-455 or 233-460 of SEQ ID NO:1; amino acids 228-455 or 228-460 of SEQ ID NO:1, amino acids 226-455- or 226-260 or amino acids 225-455- or 225-260 of SEQ ID NO:1, in which an amino acid is substituted for an R or K residue, or an R or K residue is deleted. In some embodiments, a substitution or deletion is at position 423 as determined with reference to SEQ ID NO:1. In some embodiments, a protease-resistant ANGPTL3 polypeptide comprises contiguous amino acids corresponding to the amino acid regions 207-455 or 207-460 of SEQ ID NO:1, in which an amino acid is substituted for an R or K residue, or an R or K residue is deleted. In some embodiments, a substitution or deletion is at position 423. In some embodiments, a substitution is a polar amino acid, e.g., H, N, Q, S, T, A, or Y. In some embodiments, a substitution is H, N, Q, S, T, or Y. In some embodiments, a substitution is S or Q. In some embodiments, a substitution is Q. In some embodiments, the amino acid residue corresponding to position 423 of SEQ ID NO:1 is deleted.

In some embodiments, a protease-resistant ANGPTL3 polypeptide comprises an amino acid sequence having at least 95% identity, or at least 96%, 97%, 98%, or 99% identity, to amino acids 240-454 of SEQ ID NO:1, amino acids 241-455 of SEQ ID NO:1, or amino acids 242-455 of SEQ ID NO:1 with a substitution at the amino acid corresponding to position 423 of SEQ ID NO:1, where the substituted amino acid is not R, and wherein the polypeptide has chondrogenic activity. In other embodiments, a protease-resistant ANGPTL3 polypeptide comprises amino acids 240-454 of SEQ ID NO:1, amino acids 241-455 of SEQ ID NO:1, or amino acids 242-455 of SEQ ID NO:1, each polypeptide with a substitution at the amino acid corresponding to position 423 of SEQ ID NO:1, where the substituted amino acid is Q or S. In other embodiments, a protease-resistant ANGPTL3 polypeptide comprises amino acids 240-454 of SEQ ID NO:1, amino acids 241-455 of SEQ ID NO:1, or amino acids 242-455 of SEQ ID NO:1, each polypeptide with a deletion of the amino acid residue corresponding to position 423 of SEQ ID NO:1.

In some embodiments, a protease-resistant ANGPTL3 polypeptide comprises an amino acid sequence having at least 95%, or at least 96%, at least 97%, at least 98%, or at least 99% identity to amino acids amino acids 242-455 or 242-460 of SEQ ID NO:1; 241-455 or 241-460 of SEQ ID NO:1; amino acids 233-455 or 233-460 of SEQ ID NO:1; amino acids 228-455 or 228-460 of SEQ ID NO:1, amino acids 226-455- or 226-260 of SEQ ID NO:1, or amino acids 225-455- or 225-260 of SEQ ID NO:1 in which an amino acid is substituted for an R or K. In some embodiments, the substitution is at position 423. In some embodiments, a substitution is a polar amino acid, e.g., H, N, Q, S, T, A, or Y. In some embodiments, a substitution is H, N, Q, S, T, or Y. In some embodiments, the substitution is S or Q. In some embodiments, the substitution is a Q. In some embodiments, the amino acid residue corresponding to position 423 of SEQ ID NO:1 is deleted.

In some embodiments, a protease-resistant ANGPTL3 polypeptide is PEGylated. In some embodiments, a protease-resistant ANGPTL3 polypeptide is fused to a heterologous peptide. In certain embodiments, a protease-resistant ANGPTL3 polypeptide is fused to any one of human serum albumin (HSA), an immunoglobulin heavy chain constant region (Fc), a polyhistidine, a glutathione S transferase (GST), a thioredoxin, a protein A, a protein G, a maltose binding protein (MBP), or a fragment of any of the foregoing heterologous polypeptide(s). In particular embodiments, the heterologous polypeptide is fused at the amino-terminal end of the protease-resistant ANGPTL3 polypeptide. In additional or alternative embodiments, the heterologous polypeptide is fused at the carboxyl-terminal end of the protease-resistant ANGPTL3 polypeptide.

In some embodiments, a protease-resistant ANGPTL3 polypeptide comprises at least one unnatural amino acid. In some embodiments, a polypeptide comprises 1, 2, 3, 4, or more unnatural amino acids. Methods of making and introducing a non-naturally-occurring amino acid into a protein are known. See, e.g., U.S. Pat. Nos. 7,083,970; and 7,524,647. The general principles for the production of orthogonal translation systems that are suitable for making proteins that comprise one or more desired unnatural amino acid are known in the art, as are the general methods for producing orthogonal translation systems. For example, see International Publication Numbers WO 2002/086075, entitled "METHODS AND COMPOSITION FOR THE PRODUCTION OF ORTHOGONAL tRNA-AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO 2005/007870, filed Jul. 7, 2004; WO 2005/007624, filed Jul. 7, 2004; WO 2006/110182, filed Oct. 27, 2005, entitled "ORTHOGONAL TRANSLATION COMPONENTS FOR THE VIVO INCORPORATION OF UNNATURAL AMINO ACIDS" and WO 2007/103490, filed Mar. 7, 2007, entitled "SYSTEMS FOR THE EXPRESSION OF ORTHOGONAL TRANSLATION COMPONENTS IN EUBACTERIAL HOST CELLS." For discussion of orthogonal translation systems that incorporate unnatural amino acids, and methods for their production and use, see also, Wang and Schultz, (2005) "Expanding the Genetic Code." Angewandte Chemie Int Ed 44: 34-66; Xie and Schultz, (2005) "An Expanding Genetic Code." Methods 36: 227-238; Xie and Schultz, (2005) "Adding Amino Acids to the Genetic Repertoire." Curr Opinion in Chemical Biology 9: 548-554; and Wang, et al., (2006) "Expanding the Genetic Code." Annu Rev Biophys Biomol Struct 35: 225-249; Deiters, et al, (2005) "In vivo incorporation of an alkyne into proteins in *Escherichia coli*." Bioorganic & Medicinal Chemistry Letters 15:1521-1524; Chin, et al., (2002) "Addition of p-Azido-L-phenylalanine to the Genetic Code of *Escherichia coli*." J Am Chem Soc 124: 9026-9027; and International Publication No. WO2006/034332, filed on Sep. 20, 2005. Additional details are found in U.S. Pat. Nos. 7,045,337; 7,083,970; 7,238,510; 7,129,333; 7,262,040; 7,183,082; 7,199,222; and 7,217,809.

A "non-naturally encoded amino acid" refers to an amino acid that is not one of the common amino acids or pyrolysine, pyrroline-carboxy-lysine, or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine, pyrroline-carboxy-lysine, and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

A non-naturally encoded amino acid is typically any structure having any substituent side chain other than one used in the twenty natural amino acids. Because the non-naturally encoded amino acids typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-naturally encoded amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature-including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Another type of modification that can optionally be introduced into the ANGPTL3 polypeptides (e.g. within the polypeptide chain or at either the N- or C-terminal), e.g., to extend in vivo half-life, is PEGylation or incorporation of long-chain polyethylene glycol polymers (PEG). Introduction of PEG or long chain polymers of PEG increases the effective molecular weight of the present polypeptides, for example, to prevent rapid filtration into the urine. In some embodiments, a Lysine residue in the ANGPTL3 sequence is conjugated to PEG directly or through a linker. Such linker can be, for example, a Glu residue or an acyl residue containing a thiol functional group for linkage to the appropriately modified PEG chain. An alternative method for introducing a PEG chain is to first introduce a Cys residue at the C-terminus or at solvent exposed residues such as replacements for Arg or Lys residues. This Cys residue is then site-specifically attached to a PEG chain containing, for example, a maleimide function. Methods for incorporating PEG or long chain polymers of PEG are well known in the art (described, for example, in Veronese, F. M., et al., *Drug Disc. Today* 10: 1451-8 (2005); Greenwald, R. B., et al., *Adv. Drug Deliv. Rev.* 55: 217-50 (2003); Roberts, M. J., et al., *Adv. Drug Deliv. Rev.*, 54: 459-76 (2002)), the contents of which is incorporated herein by reference. Other methods of polymer conjugations known in the art can also be used in the present invention. In some embodiments, poly(2-methacryloyloxyethyl phosphorylcholine) (PMPC) is introduced as a polymer conjugate with the ANGPTL3 polypeptide (see, e.g., WO2008/098930; Lewis, et al., *Bioconjug Chem.*, 19: 2144-55 (2008)). In some embodiments, a phosphorylcholine-containing polymer conjugate with the ANGPTL3 polypeptide can be used in the present invention. A person of skill would readily recognize that other biocompatible polymer conjugates can be utilized.

A more recently reported alternative approach for incorporating PEG or PEG polymers through incorporation of non-natural amino acids (as described above) can be performed with the present polypeptides. This approach utilizes an evolved tRNA/tRNA synthetase pair and is coded in the expression plasmid by the amber suppressor codon (Deiters, A, et al. (2004). *Bio-org. Med. Chem. Lett.* 14, 5743-5). For example, p-azidophenylalanine can be incorporated into the present polypeptides and then reacted with a PEG polymer having an acetylene moiety in the presence of a reducing agent and copper ions to facilitate an organic reaction known as "Huisgen [3+2]cycloaddition."

In certain embodiments, the present invention also contemplates specific mutations of the ANGPTL3 polypeptide so as to alter the glycosylation of the polypeptide. Such mutations may be selected so as to introduce or eliminate one or more glycosylation sites, including but not limited to, O-linked or N-linked glycosylation sites. In certain embodiments, the ANGPTL3 polypeptide has glycosylation sites and patterns unaltered relative to the naturally-occurring ANGPTL3 proteins. In certain embodiments, a variant of ANGPTL3 polypeptide includes a glycosylation variant wherein the number and/or type of glycosylation sites have been altered relative to the naturally-occurring ANGPTL3 proteins. In certain embodiments, a variant of a polypeptide comprises a greater or a lesser number of N-linked glycosylation sites relative to a native polypeptide. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. In certain embodiments, a rearrangement of N-linked carbohydrate chains is provided, wherein one or more N-linked glycosylation sites (typically those that are naturally occurring) are eliminated and one or more new N-linked sites are created.

In some embodiments, functional variants or modified forms of the ANGPTL3 polypeptides include fusion proteins of an ANGPTL3 polypeptide and one or more fusion domains. Well known examples of fusion domains include, but are not limited to, polyhistidine, Glu-Glu, glutathione S transferase (GST), thioredoxin, protein A, protein G, an immunoglobulin heavy chain constant region (Fc), maltose binding protein (MBP), and/or human serum albumin (HSA). A fusion domain or a fragment thereof may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QLAexpress™ system (Qiagen) useful with ($HIS_6$ (SEQ ID NO: 44)) fusion partners. In another example, a fusion domain may be selected so as to facilitate detection of the ANGPTL3 polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, an ANGPTL3 polypeptide is fused with a domain that stabilizes the ANGPTL3 polypeptide in vivo (a "stabilizer" domain). By "stabilizing" is meant anything that increases serum half-life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, as desired). Fusions may be constructed such that the heterologous peptide is fused at the amino terminus of an ANGPTL3 polypeptide and/or at the carboxy terminus of an ANGPTL3 polypeptide.

Method of Treatment and Therapeutic Use

Provided here are methods of treating arthritis or cartilage damage in a subject (e.g., a human subject) comprising administering to a joint of the subject (e.g., a human subject) an intra-articular dose of a protease-resistant ANGPTL3 polypeptide with chrongenic activity described herein or a composition comprising a protease-resistant ANGPTL3 polypeptide with chrongenic activity. In some embodiments, the subject has cartilage damage. In some embodiments, the subject has arthritis, e.g., osteoarthritis, trauma arthritis or autoimmune arthritis. In some embodiments, the patient has arthritis or cartilage injury. In some embodiments, the individual does not have, but is at risk for, arthritis or cartilage injury.

In some embodiments, the ANGPTL3 polypeptide is administered according to a dosage regimen described herein. Dosage regimens are adjusted to provide the optimum desired response (e.g., a therapeutic response). The efficient dosages and the dosage regimens for the ANGPTL3 polypeptide used in the present invention depend on the disease or condition to be treated.

In some embodiments, the ANGPTL3 polypeptide is administered to the joint of the subject (e.g., human subject) in a single injection. In some embodiments, the ANGPTL3 polypeptide is administered to the joint of the subject (e.g., human subject) in multiple injections. In some embodiments, the ANGPTL3 polypeptide is administered once every two weeks for a time period sufficient to treat the arthritis or cartilage damage. In some embodiments, the ANGPTL3 polypeptide is administered monthly for a time period sufficient to treat the arthritis or cartilage damage. In some embodiments, the ANGPTL3 polypeptide is administered weekly for a time period sufficient to treat the arthritis or cartilage damage.

Accordingly, provided herein are methods of treating arthritis or cartilage damage (e.g., articular cartilage damage) in a subject (e.g., a human subject) by administering to a joint of the subject an intra-articular dose of about 0.2-200 mg of a protease-resistant ANGPTL3 polypeptide with chrongenic activity described herein. For example, the ANGPTL3 polypeptide can be administered intra-articularly at a dose of about 0.2-200 mg, about 0.2-150 mg, about 0.2-120 mg, about 0.2-100 mg, about 0.2-90 mg, about 0.2-80 mg, about 0.2-70 mg, about 0.2-60 mg, about 0.2-50 mg, about 0.2-40 mg, about 0.2-30 mg, about 0.2-20 mg, about 0.2-10 mg, about 0.2-2 mg, about 2-200 mg, about 2-150 mg, about 2-120 mg, about 2-100 mg, about 2-90 mg, about 2-80 mg, about 2-70 mg, about 2-60 mg, about 2-50 mg, about 2-40 mg, about 2-30 mg, about 2-20 mg, about 2-10 mg, about 10-200 mg, about 10-150 mg, about 10-120 mg, about 10-100 mg, about 10-90 mg, about 10-80 mg, about 10-70 mg, about 10-60 mg, about 10-50 mg, about 10-40 mg, about 10-30 mg, about 10-20 mg, about 20-200 mg, about 20-150 mg, about 20-120 mg, about 20-100 mg, about 20-90 mg, about 20-80 mg, about 20-70 mg, about 20-60 mg, about 20-50 mg, about 20-40 mg, about 20-30 mg, about 40-200 mg, about 40-150 mg, about 40-120 mg, about 40-100 mg, about 40-90 mg, about 40-80 mg, about 40-70 mg, about 40-60 mg, about 40-50 mg, about 50-200 mg, about 50-150 mg, about 50-120 mg, about 50-100 mg, about 50-90 mg, about 50-80 mg, about 50-70 mg, about 50-60 mg, about 60-200 mg, about 60-150 mg, about 60-120 mg, about 60-100 mg, about 60-90 mg, about 60-80 mg, about 60-70 mg, about 70-200 mg, about 70-150 mg, about 70-120 mg, about 70-100 mg, about 70-90 mg, about 70-80 mg, about 80-200 mg, about 80-150 mg, about 80-120 mg, about 80-100 mg, about 80-90 mg, about 90-200 mg, about 90-150 mg, about 90-120 mg, about 90-100 mg, about 100-200 mg, about 100-150 mg, about 100-120 mg, about 120-200 mg, about 120-150 mg, or about 150-200 mg.

In some embodiments, provided herein are methods of treating arthritis or cartilage damage (e.g., articular cartilage damage) in a subject (e.g., a human subject) by administering to a joint of the subject an intra-articular dose of about 0.2-60 mg of a protease-resistant ANGPTL3 polypeptide with chrongenic activity described herein. For example, the ANGPTL3 polypeptide can be administered intra-articularly at a dose of about 0.2-60 mg, about 0.2-55 mg, about 0.2-50 mg, about 0.2-45 mg, about 0.2-40 mg, about 0.2-35 mg, about 0.2-30 mg, about 0.2-25 mg, about 0.2-20 mg, about 0.2-15 mg, about 0.2-10 mg, about 0.2-5 mg, about 0.2-2 mg, about 2-60 mg, about 2-55 mg, about 2-50 mg, about 2-45 mg, about 2-40 mg, about 2-35 mg, about 2-30 mg, about 2-25 mg, about 2-20 mg, about 2-15 mg, about 2-10 mg, about 2-5 mg, about 5-60 mg, about 5-55 mg, about 5-50 mg, about 5-45 mg, about 5-40 mg, about 5-35 mg, about 5-30 mg, about 5-25 mg, about 5-20 mg, about 5-15 mg, about 5-10 mg, about 10-60 mg, about 10-55 mg, about 10-50 mg, about 10-45 mg, about 10-40 mg, about 10-35 mg, about 10-30 mg, about 10-25 mg, about 10-20 mg, about 10-15 mg, about 15-60 mg, about 15-55 mg, about 15-50 mg, about 15-45 mg, about 15-40 mg, about 15-35 mg, about 15-30 mg, about 15-25 mg, about 15-20 mg, about 20-60 mg, about 20-55 mg, about 20-50 mg, about 20-45 mg, about 20-40 mg, about 20-35 mg, about 20-30 mg, about 20-25 mg, about 25-60 mg, about 25-55 mg, about 25-50 mg, about 25-45 mg, about 25-40 mg, about 25-35 mg, about 25-30 mg, about 30-60 mg, about 30-55 mg, about 30-50 mg, about 30-45 mg, about 30-40 mg, about 30-35 mg, about 35-60 mg, about 35-55 mg, about 35-50 mg, about 35-45 mg, about 35-40 mg, about 40-60 mg, about 40-55 mg, about 40-50 mg, about 40-45 mg, about 45-60 mg, about 45-55 mg, about 45-50 mg, about 50-60 mg, about 50-55 mg, about 55-60 mg, about 0.2 mg, about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, or about 60 mg.

In some embodiments, provided herein are methods of treating arthritis or cartilage damage (e.g., articular cartilage damage) in a subject (e.g., a human subject) by administering to a joint of the subject an intra-articular dose of about 0.2-40 mg of a protease-resistant ANGPTL3 polypeptide with chrongenic activity described herein. For example, the ANGPTL3 polypeptide can be administered intra-articularly at a dose of about 0.2-40 mg, about 0.2-35 mg, about 0.2-30 mg, about 0.2-25 mg, about 0.2-20 mg, about 0.2-15 mg, about 0.2-10 mg, about 0.2-5 mg, about 0.2-2 mg, about 2-40 mg, about 2-35 mg, about 2-30 mg, about 2-25 mg, about 2-20 mg, about 2-15 mg, about 2-10 mg, about 2-5 mg, about 5-40 mg, about 5-35 mg, about 5-30 mg, about 5-25 mg, about 5-20 mg, about 5-15 mg, about 5-10 mg, about 10-40 mg, about 10-35 mg, about 10-30 mg, about 10-25 mg, about 10-20 mg, about 10-15 mg, about 15-40 mg, about 15-35 mg, about 15-30 mg, about 15-25 mg, about 15-20 mg, about 20-40 mg, about 20-35 mg, about 20-30 mg, about 20-25 mg, about 25-60 mg, about 25-55 mg, about 25-50 mg, about 25-45 mg, about 25-40 mg, about 25-35 mg, about 25-30 mg, about 30-40 mg, about 30-35 mg, about 35-40 mg, about 0.2 mg, about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, or about 40 mg.

In some embodiments, the intra-articular dose of a protease-resistant ANGPTL3 polypeptide is about 0.2-100 mg. In some embodiments, the intra-articular dose of a protease-resistant ANGPTL3 polypeptide is about 0.2-60 mg. In some embodiments, the intra-articular dose of a protease-resistant ANGPTL3 polypeptide is about 0.2-40 mg. In some embodiments, the intra-articular dose of a protease-resistant ANGPTL3 polypeptide is about 2-40 mg. In some embodiments, the intra-articular dose of a protease-resistant ANGPTL3 polypeptide is about 10-40 mg. In some embodiments, the intra-articular dose of a protease-resistant ANGPTL3 polypeptide is about 20-40 mg. In some embodiments, the intra-articular dose of a protease-resistant ANGPTL3 polypeptide is about 40-60 mg. In some embodiments, the intra-articular dose of a protease-resistant ANGPTL3 polypeptide is about 0.2 mg. In some embodiments, the intra-articular dose of a protease-resistant ANGPTL3 polypeptide is about 2 mg. In some embodiments, the intra-articular dose of a protease-resistant ANGPTL3 polypeptide is about 10 mg. In some embodiments, the intra-articular dose of a protease-resistant ANGPTL3 polypeptide is about 20 mg. In some embodiments, the intra-articular dose of a protease-resistant ANGPTL3 polypeptide is about 40 mg. In some embodiments, the intra-articular dose of a protease-resistant ANGPTL3 polypeptide is about 60 mg.

In some embodiments, the protease-resistant ANGPTL3 polypeptide comprises an amino acid sequence that has at least 95% identity, or at least 96%, 97%, 98%, or 99% identity, to an amino acid sequence listed in TABLE 1, wherein the polypeptide comprises an amino acid that is a polar amino acid other than K or R at position 423, as determined with reference to SEQ ID NO:1, and the polypeptide has chondrogenic activity. In some embodiments, the protease-resistant ANGPTL3 polypeptide comprises an amino acid sequence that has at least 95% identity, or at least 96%, 97%, 98%, or 99% identity, to an amino acid sequence listed in TABLE 1, wherein the amino acid residue corresponding to position 423 of SEQ ID NO: 1 is Q or S or deleted.

In some embodiments, the protease-resistant ANGPTL3 polypeptide comprises an amino acid sequence selected from any one of the sequences listed in TABLE 1. In some embodiments, the protease-resistant ANGPTL3 polypeptide consists of an amino acid sequence selected from any one of the sequences listed in TABLE 1. In some embodiments, the protease-resistant ANGPTL3 polypeptide comprises SEQ ID NO: 17. In some embodiments, the protease-resistant ANGPTL3 polypeptide consists of SEQ ID NO: 17.

In some embodiments, provided herein are methods of treating arthritis or cartilage damage (e.g., articular cartilage damage) in a subject (e.g., a human subject) by administering to a joint of the subject an intra-articular dose of about 0.2-200 mg of a polypeptide comprising SEQ ID NO: 17. For example, the polypeptide comprising SEQ ID NO: 17 can be administered intra-articularly at a dose of about 0.2-200 mg, about 0.2-150 mg, about 0.2-120 mg, about 0.2-100 mg, about 0.2-90 mg, about 0.2-80 mg, about 0.2-70 mg, about 0.2-60 mg, about 0.2-50 mg, about 0.2-40 mg, about 0.2-30 mg, about 0.2-20 mg, about 0.2-10 mg, about 0.2-2 mg, about 2-200 mg, about 2-150 mg, about 2-120 mg, about 2-100 mg, about 2-90 mg, about 2-80 mg, about 2-70 mg, about 2-60 mg, about 2-50 mg, about 2-40 mg, about 2-30 mg, about 2-20 mg, about 2-10 mg, about 10-200 mg, about 10-150 mg, about 10-120 mg, about 10-100 mg, about 10-90 mg, about 10-80 mg, about 10-70 mg, about 10-60 mg, about 10-50 mg, about 10-40 mg, about 10-30 mg, about 10-20 mg, about 20-200 mg, about 20-150 mg, about 20-120 mg, about 20-100 mg, about 20-90 mg, about 20-80 mg, about 20-70 mg, about 20-60 mg, about 20-50 mg, about 20-40 mg, about 20-30 mg, about 40-200 mg, about 40-150 mg, about 40-120 mg, about 40-100 mg, about 40-90 mg, about 40-80 mg, about 40-70 mg, about 40-60 mg, about 40-50 mg, about 50-200 mg, about 50-150 mg, about 50-120 mg, about 50-100 mg, about 50-90 mg, about 50-80 mg, about 50-70 mg, about 50-60 mg, about 60-200 mg, about 60-150 mg, about 60-120 mg, about 60-100 mg, about 60-90 mg, about 60-80 mg, about 60-70 mg, about 70-200 mg, about 70-150 mg, about 70-120 mg, about 70-100 mg, about 70-90 mg, about 70-80 mg, about 80-200 mg, about 80-150 mg, about 80-120 mg, about 80-100 mg, about 80-90 mg, about 90-200 mg, about 90-150 mg, about 90-120 mg, about 90-100 mg, about 100-200 mg, about 100-150 mg, about 100-120 mg, about 120-200 mg, about 120-150 mg, or about 150-200 mg.

In some embodiments, provided herein are methods of treating arthritis or cartilage damage (e.g., articular cartilage damage) in a subject (e.g., a human subject) by administering to a joint of the subject an intra-articular dose of about 0.2-60 mg of a polypeptide comprising SEQ ID NO: 17. For example, the a polypeptide comprising SEQ ID NO: 17 can be administered intra-articularly at a dose of about 0.2-60 mg, about 0.2-55 mg, about 0.2-50 mg, about 0.2-45 mg, about 0.2-40 mg, about 0.2-35 mg, about 0.2-30 mg, about 0.2-25 mg, about 0.2-20 mg, about 0.2-15 mg, about 0.2-10 mg, about 0.2-5 mg, about 0.2-2 mg, about 2-60 mg, about 2-55 mg, about 2-50 mg, about 2-45 mg, about 2-40 mg, about 2-35 mg, about 2-30 mg, about 2-25 mg, about 2-20 mg, about 2-15 mg, about 2-10 mg, about 2-5 mg, about 5-60 mg, about 5-55 mg, about 5-50 mg, about 5-45 mg, about 5-40 mg, about 5-35 mg, about 5-30 mg, about 5-25 mg, about 5-20 mg, about 5-15 mg, about 5-10 mg, about 10-60 mg, about 10-55 mg, about 10-50 mg, about 10-45 mg, about 10-40 mg, about 10-35 mg, about 10-30 mg, about 10-25 mg, about 10-20 mg, about 10-15 mg, about 15-60 mg, about 15-55 mg, about 15-50 mg, about 15-45 mg, about 15-40 mg, about 15-35 mg, about 15-30 mg, about 15-25 mg, about 15-20 mg, about 20-60 mg, about 20-55 mg, about 20-50 mg, about 20-45 mg, about 20-40 mg, about 20-35 mg, about 20-30 mg, about 20-25 mg, about 25-60 mg, about 25-55 mg, about 25-50 mg, about 25-45 mg, about 25-40 mg, about 25-35 mg, about 25-30 mg, about 30-60 mg, about 30-55 mg, about 30-50 mg, about 30-45 mg, about 30-40 mg, about 30-35 mg, about 35-60 mg, about 35-55 mg, about 35-50 mg, about 35-45 mg, about 35-40 mg, about 40-60 mg, about 40-55 mg, about 40-50 mg, about 40-45 mg, about 45-60 mg, about 45-55 mg, about 45-50 mg, about 50-60 mg, about 50-55 mg, about 55-60 mg, about 0.2 mg, about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, or about 60 mg.

In some embodiments, provided herein are methods of treating arthritis or cartilage damage (e.g., articular cartilage damage) in a subject (e.g., a human subject) by administering to a joint of the subject an intra-articular dose of about 0.2-40 mg of a polypeptide comprising SEQ ID NO: 17. For example, the polypeptide comprising SEQ ID NO: 17 can be administered intra-articularly at a dose of about 0.2-40 mg, about 0.2-35 mg, about 0.2-30 mg, about 0.2-25 mg, about 0.2-20 mg, about 0.2-15 mg, about 0.2-10 mg, about 0.2-5 mg, about 0.2-2 mg, about 2-40 mg, about 2-35 mg, about 2-30 mg, about 2-25 mg, about 2-20 mg, about 2-15 mg, about 2-10 mg, about 2-5 mg, about 5-40 mg, about 5-35 mg, about 5-30 mg, about 5-25 mg, about 5-20 mg, about 5-15 mg, about 5-10 mg, about 10-40 mg, about 10-35 mg, about 10-30 mg, about 10-25 mg, about 10-20 mg, about 10-15 mg, about 15-40 mg, about 15-35 mg, about 15-30 mg, about 15-25 mg, about 15-20 mg, about 20-40 mg, about 20-35 mg, about 20-30 mg, about 20-25 mg, about 25-60 mg, about 25-55 mg, about 25-50 mg, about 25-45 mg, about 25-40 mg, about 25-35 mg, about 25-30 mg, about 30-40 mg, about 30-35 mg, about 35-40 mg, about 0.2 mg, about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, or about 40 mg.

In some embodiments, provided herein are methods of treating arthritis or cartilage damage (e.g., articular cartilage damage) in a subject (e.g., a human subject) by administering to a joint of the subject an intra-articular dose of about 0.2-200 mg of a polypeptide consisting of SEQ ID NO: 17. For example, the polypeptide consisting of SEQ ID NO: 17 can be administered intra-articularly at a dose of about 0.2-200 mg, about 0.2-150 mg, about 0.2-120 mg, about 0.2-100 mg, about 0.2-90 mg, about 0.2-80 mg, about 0.2-70 mg, about 0.2-60 mg, about 0.2-50 mg, about 0.2-40 mg, about 0.2-30 mg, about 0.2-20 mg, about 0.2-10 mg, about 0.2-2 mg, about 2-200 mg, about 2-150 mg, about 2-120 mg, about 2-100 mg, about 2-90 mg, about 2-80 mg, about 2-70 mg, about 2-60 mg, about 2-50 mg, about 2-40 mg, about 2-30 mg, about 2-20 mg, about 2-10 mg, about 10-200 mg, about 10-150 mg, about 10-120 mg, about 10-100 mg, about 10-90 mg, about 10-80 mg, about 10-70 mg, about 10-60 mg, about 10-50 mg, about 10-40 mg, about 10-30 mg, about 10-20 mg, about 20-200 mg, about 20-150 mg, about 20-120 mg, about 20-100 mg, about 20-90 mg, about 20-80 mg, about 20-70 mg, about 20-60 mg, about 20-50 mg, about 20-40 mg, about 20-30 mg, about 40-200 mg, about 40-150 mg, about 40-120 mg, about 40-100 mg, about 40-90 mg, about 40-80 mg, about 40-70 mg, about 40-60 mg, about 40-50 mg, about 50-200 mg, about 50-150 mg, about 50-120 mg, about 50-100 mg, about 50-90 mg, about 50-80 mg, about 50-70 mg, about 50-60 mg, about 60-200 mg, about 60-150 mg, about 60-120 mg, about 60-100 mg, about 60-90 mg, about 60-80 mg, about 60-70 mg, about 70-200 mg, about 70-150 mg, about 70-120 mg, about 70-100 mg, about 70-90 mg, about 70-80 mg, about 80-200 mg, about 80-150 mg, about 80-120 mg, about 80-100 mg, about 80-90 mg, about 90-200 mg, about 90-150 mg, about 90-120 mg, about 90-100 mg, about 100-200 mg, about 100-150 mg, about 100-120 mg, about 120-200 mg, about 120-150 mg, or about 150-200 mg.

In some embodiments, provided herein are methods of treating arthritis or cartilage damage (e.g., articular cartilage damage) in a subject (e.g., a human subject) by administering to a joint of the subject an intra-articular dose of about 0.2-60 mg of a polypeptide consisting of SEQ ID NO: 17. For example, the a polypeptide consisting of SEQ ID NO: 17 can be administered intra-articularly at a dose of about 0.2-60 mg, about 0.2-55 mg, about 0.2-50 mg, about 0.2-45 mg, about 0.2-40 mg, about 0.2-35 mg, about 0.2-30 mg, about 0.2-25 mg, about 0.2-20 mg, about 0.2-15 mg, about 0.2-10 mg, about 0.2-5 mg, about 0.2-2 mg, about 2-60 mg, about 2-55 mg, about 2-50 mg, about 2-45 mg, about 2-40 mg, about 2-35 mg, about 2-30 mg, about 2-25 mg, about 2-20 mg, about 2-15 mg, about 2-10 mg, about 2-5 mg, about 5-60 mg, about 5-55 mg, about 5-50 mg, about 5-45 mg, about 5-40 mg, about 5-35 mg, about 5-30 mg, about 5-25 mg, about 5-20 mg, about 5-15 mg, about 5-10 mg, about 10-60 mg, about 10-55 mg, about 10-50 mg, about 10-45 mg, about 10-40 mg, about 10-35 mg, about 10-30 mg, about 10-25 mg, about 10-20 mg, about 10-15 mg, about 15-60 mg, about 15-55 mg, about 15-50 mg, about 15-45 mg, about 15-40 mg, about 15-35 mg, about 15-30 mg, about 15-25 mg, about 15-20 mg, about 20-60 mg, about 20-55 mg, about 20-50 mg, about 20-45 mg, about 20-40 mg, about 20-35 mg, about 20-30 mg, about 20-25 mg, about 25-60 mg, about 25-55 mg, about 25-50 mg, about 25-45 mg, about 25-40 mg, about 25-35 mg, about 25-30 mg, about 30-60 mg, about 30-55 mg, about 30-50 mg, about 30-45 mg, about 30-40 mg, about 30-35 mg, about 35-60 mg, about 35-55 mg, about 35-50 mg, about 35-45 mg, about 35-40 mg, about 40-60 mg, about 40-55 mg, about 40-50 mg, about 40-45 mg, about 45-60 mg, about 45-55 mg, about 45-50 mg, about 50-60 mg, about 50-55 mg, about 55-60 mg, about 0.2 mg, about 0.5 mg, about 1 mg, about 2 mg, about 3 mg, about 4 mg, about 5 mg, about 6 mg, about 7 mg, about 8 mg, about 9 mg, about 10 mg, about 1 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, or about 60 mg.

In some embodiments, provided herein are methods of treating arthritis or cartilage damage (e.g., articular cartilage damage) in a subject (e.g., a human subject) by administering to a joint of the subject an intra-articular dose of about 0.2-40 mg of a polypeptide consisting of SEQ ID NO: 17. For example, the polypeptide consisting of SEQ ID NO: 17 can be administered intra-articularly at a dose of about 0.2-40 mg, about 0.2-35 mg, about 0.2-30 mg, about 0.2-25 mg, about 0.2-20 mg, about 0.2-15 mg, about 0.2-10 mg, about 0.2-5 mg, about 0.2-2 mg, about 2-40 mg, about 2-35 mg, about 2-30 mg, about 2-25 mg, about 2-20 mg, about 2-15 mg, about 2-10 mg, about 2-5 mg, about 5-40 mg, about 5-35 mg, about 5-30 mg, about 5-25 mg, about 5-20 mg, about 5-15 mg, about 5-10 mg, about 10-40 mg, about 10-35 mg, about 10-30 mg, about 10-25 mg, about 10-20 mg, about 10-15 mg, about 15-40 mg, about 15-35 mg, about 15-30 mg, about 15-25 mg, about 15-20 mg, about 20-40 mg, about 20-35 mg, about 20-30 mg, about 20-25 mg, about 25-60 mg, about 25-55 mg, about 25-50 mg, about 25-45 mg, about 25-40 mg, about 25-35 mg, about 25-30 mg, about 30-40 mg, about 30-35 mg, about 35-40 mg, about 0.2 mg, about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, or about 40 mg.

In some embodiments, the intra-articular dose of the polypeptide comprising or consisting of SEQ ID NO: 17 is about 0.2-100 mg. In some embodiments, the intra-articular dose of the polypeptide comprising or consisting of SEQ ID NO: 17 is about 0.2-60 mg. In some embodiments, the intra-articular dose of the polypeptide comprising or consisting of SEQ ID NO: 17 is about 0.2-40 mg. In some embodiments, the intra-articular dose of the polypeptide comprising or consisting of SEQ ID NO: 17 is about 2-40 mg. In some embodiments, the intra-articular dose of the polypeptide comprising or consisting of SEQ ID NO: 17 is about 10-40 mg. In some embodiments, the intra-articular dose of the polypeptide comprising or consisting of SEQ ID NO: 17 is about 20-40 mg. In some embodiments, the intra-articular dose of the polypeptide comprising or consisting of SEQ ID NO: 17 is about 40-60 mg. In some embodiments, the intra-articular dose of the polypeptide comprising or consisting of SEQ ID NO: 17 is about 0.2 mg. In some embodiments, the intra-articular dose of the polypeptide comprising or consisting of SEQ ID NO: 17 is about 2 mg. In some embodiments, the intra-articular dose of the polypeptide comprising or consisting of SEQ ID NO: 17 is about 10 mg. In some embodiments, the intra-articular dose of the polypeptide comprising or consisting of SEQ ID NO: 17 is about 20 mg. In some embodiments, the intra-articular dose of the polypeptide comprising or consisting of SEQ ID NO: 17 is about 40 mg. In some embodiments, the intra-articular dose of the polypeptide comprising or consisting of SEQ ID NO: 17 is about 60 mg.

In some embodiments, the methods further comprise performing a surgical procedure to an affected joint in the subject. The polypeptide or composition can be administered before, during or after the surgical procedure.

In some embodiments, the methods further comprise an additional procedure. For example, the polypeptide or composition can be administered in conjunction with any one of bone marrow stimulation, cartilage replacement, autologous chondrocyte implantation (ACI), or matrix-induced autologous chondrocyte implantation (MACI). In some embodiments, the polypeptide or composition can be administered in conjunction with ACI.

Also provided are compositions comprising a protease-resistant ANGPTL3 polypeptide with chrongenic activity described herein for use in the treatment of arthritis or cartilage damage (e.g., articular cartilage damage). For example, such compositions can comprise an ANGPTL3 polypeptide comprising an amino acid sequence that has at least 95% identity, or at least 96%, 97%, 98%, or 99% identity, to an amino acid sequence listed in TABLE 1, wherein the polypeptide comprises an amino acid that is a polar amino acid other than K or R at position 423, as determined with reference to SEQ ID NO:1, and the polypeptide has chondrogenic activity. In some embodiments, such compositions comprise an ANGPTL3 polypeptide comprising an amino acid sequence that has at least 95% identity, or at least 96%, 97%, 98%, or 99% identity, to an amino acid sequence listed in TABLE 1, wherein the amino acid residue corresponding to position 423 of SEQ ID NO:1 is Q or S or deleted. In some embodiments, such compositions comprise an ANGPTL3 polypeptide comprising an amino acid sequence selected from any one of the sequences listed in TABLE 1. In some embodiments, such compositions comprise an ANGPTL3 polypeptide consisting of an amino acid sequence selected from any one of the sequences listed in TABLE 1.

Such compositions can comprise about 0.2-200 mg (e.g., 0.2-200 mg, about 0.2-150 mg, about 0.2-120 mg, about 0.2-100 mg, about 0.2-90 mg, about 0.2-80 mg, about 0.2-70 mg, about 0.2-60 mg, about 0.2-50 mg, about 0.2-40 mg, about 0.2-30 mg, about 0.2-20 mg, about 0.2-10 mg, about 0.2-2 mg, about 2-200 mg, about 2-150 mg, about 2-120 mg, about 2-100 mg, about 2-90 mg, about 2-80 mg, about 2-70 mg, about 2-60 mg, about 2-50 mg, about 2-40 mg, about 2-30 mg, about 2-20 mg, about 2-10 mg, about 10-200 mg, about 10-150 mg, about 10-120 mg, about 10-100 mg, about 10-90 mg, about 10-80 mg, about 10-70 mg, about 10-60 mg, about 10-50 mg, about 10-40 mg, about 10-30 mg, about 10-20 mg, about 20-200 mg, about 20-150 mg, about 20-120 mg, about 20-100 mg, about 20-90 mg, about 20-80 mg, about 20-70 mg, about 20-60 mg, about 20-50 mg, about 20-40 mg, about 20-30 mg, about 40-200 mg, about 40-150 mg, about 40-120 mg, about 40-100 mg, about 40-90 mg, about 40-80 mg, about 40-70 mg, about 40-60 mg, about 40-50 mg, about 50-200 mg, about 50-150 mg, about 50-120 mg, about 50-100 mg, about 50-90 mg, about 50-80 mg, about 50-70 mg, about 50-60 mg, about 60-200 mg, about 60-150 mg, about 60-120 mg, about 60-100 mg, about 60-90 mg, about 60-80 mg, about 60-70 mg, about 70-200 mg, about 70-150 mg, about 70-120 mg, about 70-100 mg, about 70-90 mg, about 70-80 mg, about 80-200 mg, about 80-150 mg, about 80-120 mg, about 80-100 mg, about 80-90 mg, about 90-200 mg, about 90-150 mg, about 90-120 mg, about 90-100 mg, about 100-200 mg, about 100-150 mg, about 100-120 mg, about 120-200 mg, about 120-150 mg, about 150-200 mg) of a protease-resistant ANGPTL3 polypeptide with chondrogenic activity described herein.

In some embodiments, such compositions comprise about 0.2-60 mg (e.g., about 0.2-60 mg, about 0.2-55 mg, about 0.2-50 mg, about 0.2-45 mg, about 0.2-40 mg, about 0.2-35 mg, about 0.2-30 mg, about 0.2-25 mg, about 0.2-20 mg, about 0.2-15 mg, about 0.2-10 mg, about 0.2-5 mg, about 0.2-2 mg, about 2-60 mg, about 2-55 mg, about 2-50 mg, about 2-45 mg, about 2-40 mg, about 2-35 mg, about 2-30 mg, about 2-25 mg, about 2-20 mg, about 2-15 mg, about 2-10 mg, about 2-5 mg, about 5-60 mg, about 5-55 mg, about 5-50 mg, about 5-45 mg, about 5-40 mg, about 5-35 mg, about 5-30 mg, about 5-25 mg, about 5-20 mg, about 5-15 mg, about 5-10 mg, about 10-60 mg, about 10-55 mg, about 10-50 mg, about 10-45 mg, about 10-40 mg, about 10-35 mg, about 10-30 mg, about 10-25 mg, about 10-20 mg, about 10-15 mg, about 15-60 mg, about 15-55 mg, about 15-50 mg, about 15-45 mg, about 15-40 mg, about 15-35 mg, about 15-30 mg, about 15-25 mg, about 15-20 mg, about 20-60 mg, about 20-55 mg, about 20-50 mg, about 20-45 mg, about 20-40 mg, about 20-35 mg, about 20-30 mg, about 20-25 mg, about 25-60 mg, about 25-55 mg, about 25-50 mg, about 25-45 mg, about 25-40 mg, about 25-35 mg, about 25-30 mg, about 30-60 mg, about 30-55 mg, about 30-50 mg, about 30-45 mg, about 30-40 mg, about 30-35 mg, about 35-60 mg, about 35-55 mg, about 35-50 mg, about 35-45 mg, about 35-40 mg, about 40-60 mg, about 40-55 mg, about 40-50 mg, about 40-45 mg, about 45-60 mg, about 45-55 mg, about 45-50 mg, about 50-60 mg, about 50-55 mg, about 55-60 mg, about 0.2 mg, about 0.5 mg, about 1 mg, about 2 mg, about 3 mg, about 4 mg, about 5 mg, about 6 mg, about 7 mg, about 8 mg, about 9 mg, about 10 mg, about 1 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg) of a protease-resistant ANGPTL3 polypeptide with chondrogenic activity described herein.

In some embodiments, such compositions comprise about 0.2-40 mg (e.g., about 0.2-40 mg, about 0.2-35 mg, about 0.2-30 mg, about 0.2-25 mg, about 0.2-20 mg, about 0.2-15 mg, about 0.2-10 mg, about 0.2-5 mg, about 0.2-2 mg, about 2-40 mg, about 2-35 mg, about 2-30 mg, about 2-25 mg, about 2-20 mg, about 2-15 mg, about 2-10 mg, about 2-5 mg, about 5-40 mg, about 5-35 mg, about 5-30 mg, about 5-25 mg, about 5-20 mg, about 5-15 mg, about 5-10 mg, about 10-40 mg, about 10-35 mg, about 10-30 mg, about 10-25 mg, about 10-20 mg, about 10-15 mg, about 15-40 mg, about 15-35 mg, about 15-30 mg, about 15-25 mg, about 15-20 mg, about 20-40 mg, about 20-35 mg, about 20-30 mg, about 20-25 mg, about 25-60 mg, about 25-55 mg, about 25-50 mg, about 25-45 mg, about 25-40 mg, about 25-35 mg, about 25-30 mg, about 30-40 mg, about 30-35 mg, about 35-40 mg, about 0.2 mg, about 0.5 mg, about 1 mg, about 2 mg, about 3 mg, about 4 mg, about 5 mg, about 6 mg, about 7 mg, about 8 mg, about 9 mg, about 10 mg, about 1 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg) of a protease-resistant ANGPTL3 polypeptide with chondrogenic activity described herein.

In some embodiments, provided are compositions comprising a polypeptide comprising SEQ ID NO: 17 for use in the treatment of arthritis or cartilage damage (e.g., articular cartilage damage). In some embodiments, provided are compositions comprising a polypeptide consisting of SEQ ID NO: 17 for use in the treatment of arthritis or cartilage damage (e.g., articular cartilage damage).

Such compositions can comprise about 0.2-200 mg (e.g., 0.2-200 mg, about 0.2-150 mg, about 0.2-120 mg, about 0.2-100 mg, about 0.2-90 mg, about 0.2-80 mg, about 0.2-70 mg, about 0.2-60 mg, about 0.2-50 mg, about 0.2-40 mg, about 0.2-30 mg, about 0.2-20 mg, about 0.2-10 mg, about 0.2-2 mg, about 2-200 mg, about 2-150 mg, about 2-120 mg, about 2-100 mg, about 2-90 mg, about 2-80 mg, about 2-70 mg, about 2-60 mg, about 2-50 mg, about 2-40 mg, about 2-30 mg, about 2-20 mg, about 2-10 mg, about 10-200 mg, about 10-150 mg, about 10-120 mg, about 10-100 mg, about 10-90 mg, about 10-80 mg, about 10-70 mg, about 10-60 mg, about 10-50 mg, about 10-40 mg, about 10-30 mg, about 10-20 mg, about 20-200 mg, about 20-150 mg, about 20-120 mg, about 20-100 mg, about 20-90 mg, about 20-80 mg, about 20-70 mg, about 20-60 mg, about 20-50 mg, about 20-40 mg, about 20-30 mg, about 40-200 mg, about 40-150 mg, about 40-120 mg, about 40-100 mg, about 40-90 mg, about 40-80 mg, about 40-70 mg, about 40-60 mg, about 40-50 mg, about 50-200 mg, about 50-150 mg, about 50-120 mg, about 50-100 mg, about 50-90 mg, about 50-80 mg, about 50-70 mg, about 50-60 mg, about 60-200 mg, about 60-150 mg, about 60-120 mg, about 60-100 mg, about 60-90 mg, about 60-80 mg, about 60-70 mg, about 70-200 mg, about 70-150 mg, about 70-120 mg, about 70-100 mg, about 70-90 mg, about 70-80 mg, about 80-200 mg, about 80-150 mg, about 80-120 mg, about 80-100 mg, about 80-90 mg, about 90-200 mg, about 90-150 mg, about 90-120 mg, about 90-100 mg, about 100-200 mg, about 100-150 mg, about 100-120 mg, about 120-200 mg, about 120-150 mg, about 150-200 mg) of a polypeptide comprising SEQ ID NO: 17.

In some embodiments, such compositions comprise about 0.2-60 mg (e.g., about 0.2-60 mg, about 0.2-55 mg, about 0.2-50 mg, about 0.2-45 mg, about 0.2-40 mg, about 0.2-35 mg, about 0.2-30 mg, about 0.2-25 mg, about 0.2-20 mg, about 0.2-15 mg, about 0.2-10 mg, about 0.2-5 mg, about 0.2-2 mg, about 2-60 mg, about 2-55 mg, about 2-50 mg, about 2-45 mg, about 2-40 mg, about 2-35 mg, about 2-30 mg, about 2-25 mg, about 2-20 mg, about 2-15 mg, about 2-10 mg, about 2-5 mg, about 5-60 mg, about 5-55 mg, about 5-50 mg, about 5-45 mg, about 5-40 mg, about 5-35 mg, about 5-30 mg, about 5-25 mg, about 5-20 mg, about 5-15 mg, about 5-10 mg, about 10-60 mg, about 10-55 mg, about 10-50 mg, about 10-45 mg, about 10-40 mg, about 10-35 mg, about 10-30 mg, about 10-25 mg, about 10-20 mg, about 10-15 mg, about 15-60 mg, about 15-55 mg, about 15-50 mg, about 15-45 mg, about 15-40 mg, about 15-35 mg, about 15-30 mg, about 15-25 mg, about 15-20 mg, about 20-60 mg, about 20-55 mg, about 20-50 mg, about 20-45 mg, about 20-40 mg, about 20-35 mg, about 20-30 mg, about 20-25 mg, about 25-60 mg, about 25-55 mg, about 25-50 mg, about 25-45 mg, about 25-40 mg, about 25-35 mg, about 25-30 mg, about 30-60 mg, about 30-55 mg, about 30-50 mg, about 30-45 mg, about 30-40 mg, about 30-35 mg, about 35-60 mg, about 35-55 mg, about 35-50 mg, about 35-45 mg, about 35-40 mg, about 40-60 mg, about 40-55 mg, about 40-50 mg, about 40-45 mg, about 45-60 mg, about 45-55 mg, about 45-50 mg, about 50-60 mg, about 50-55 mg, about 55-60 mg, about 0.2 mg, about 0.5 mg, about 1 mg, about 2 mg, about 3 mg, about 4 mg, about 5 mg, about 6 mg, about 7 mg, about 8 mg, about 9 mg, about 10 mg, about 1 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg) of a polypeptide comprising SEQ ID NO: 17.

In some embodiments, such compositions comprise about 0.2-40 mg (e.g., about 0.2-40 mg, about 0.2-35 mg, about 0.2-30 mg, about 0.2-25 mg, about 0.2-20 mg, about 0.2-15 mg, about 0.2-10 mg, about 0.2-5 mg, about 0.2-2 mg, about 2-40 mg, about 2-35 mg, about 2-30 mg, about 2-25 mg, about 2-20 mg, about 2-15 mg, about 2-10 mg, about 2-5 mg, about 5-40 mg, about 5-35 mg, about 5-30 mg, about 5-25 mg, about 5-20 mg, about 5-15 mg, about 5-10 mg, about 10-40 mg, about 10-35 mg, about 10-30 mg, about 10-25 mg, about 10-20 mg, about 10-15 mg, about 15-40 mg, about 15-35 mg, about 15-30 mg, about 15-25 mg, about 15-20 mg, about 20-40 mg, about 20-35 mg, about 20-30 mg, about 20-25 mg, about 25-60 mg, about 25-55 mg, about 25-50 mg, about 25-45 mg, about 25-40 mg, about 25-35 mg, about 25-30 mg, about 30-40 mg, about 30-35 mg, about 35-40 mg, about 0.2 mg, about 0.5 mg, about 1 mg, about 2 mg, about 3 mg, about 4 mg, about 5 mg, about 6 mg, about 7 mg, about 8 mg, about 9 mg, about 10 mg, about 1 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg) of a polypeptide comprising SEQ ID NO: 17.

Such compositions can comprise about 0.2-200 mg (e.g., 0.2-200 mg, about 0.2-150 mg, about 0.2-120 mg, about 0.2-100 mg, about 0.2-90 mg, about 0.2-80 mg, about 0.2-70 mg, about 0.2-60 mg, about 0.2-50 mg, about 0.2-40 mg, about 0.2-30 mg, about 0.2-20 mg, about 0.2-10 mg, about 0.2-2 mg, about 2-200 mg, about 2-150 mg, about 2-120 mg, about 2-100 mg, about 2-90 mg, about 2-80 mg, about 2-70 mg, about 2-60 mg, about 2-50 mg, about 2-40 mg, about 2-30 mg, about 2-20 mg, about 2-10 mg, about 10-200 mg, about 10-150 mg, about 10-120 mg, about 10-100 mg, about 10-90 mg, about 10-80 mg, about 10-70 mg, about 10-60 mg, about 10-50 mg, about 10-40 mg, about 10-30 mg, about 10-20 mg, about 20-200 mg, about 20-150 mg, about 20-120 mg, about 20-100 mg, about 20-90 mg, about 20-80 mg, about 20-70 mg, about 20-60 mg, about 20-50 mg, about 20-40 mg, about 20-30 mg, about 40-200 mg, about 40-150 mg, about 40-120 mg, about 40-100 mg, about 40-90 mg, about 40-80 mg, about 40-70 mg, about 40-60 mg, about 40-50 mg, about 50-200 mg, about 50-150 mg, about 50-120 mg, about 50-100 mg, about 50-90 mg, about 50-80 mg, about 50-70 mg, about 50-60 mg, about 60-200 mg, about 60-150 mg, about 60-120 mg, about 60-100 mg, about 60-90 mg, about 60-80 mg, about 60-70 mg, about 70-200 mg, about 70-150 mg, about 70-120 mg, about 70-100 mg, about 70-90 mg, about 70-80 mg, about 80-200 mg, about 80-150 mg, about 80-120 mg, about 80-100 mg, about 80-90 mg, about 90-200 mg, about 90-150 mg, about 90-120 mg, about 90-100 mg, about 100-200 mg, about 100-150 mg, about 100-120 mg, about 120-200 mg, about 120-150 mg, about 150-200 mg) of a polypeptide consisting of SEQ ID NO: 17.

In some embodiments, such compositions comprise about 0.2-60 mg (e.g., about 0.2-60 mg, about 0.2-55 mg, about 0.2-50 mg, about 0.2-45 mg, about 0.2-40 mg, about 0.2-35 mg, about 0.2-30 mg, about 0.2-25 mg, about 0.2-20 mg, about 0.2-15 mg, about 0.2-10 mg, about 0.2-5 mg, about 0.2-2 mg, about 2-60 mg, about 2-55 mg, about 2-50 mg, about 2-45 mg, about 2-40 mg, about 2-35 mg, about 2-30 mg, about 2-25 mg, about 2-20 mg, about 2-15 mg, about 2-10 mg, about 2-5 mg, about 5-60 mg, about 5-55 mg, about 5-50 mg, about 5-45 mg, about 5-40 mg, about 5-35 mg, about 5-30 mg, about 5-25 mg, about 5-20 mg, about 5-15 mg, about 5-10 mg, about 10-60 mg, about 10-55 mg, about 10-50 mg, about 10-45 mg, about 10-40 mg, about 10-35 mg, about 10-30 mg, about 10-25 mg, about 10-20 mg, about 10-15 mg, about 15-60 mg, about 15-55 mg, about 15-50 mg, about 15-45 mg, about 15-40 mg, about 15-35 mg, about 15-30 mg, about 15-25 mg, about 15-20 mg, about 20-60 mg, about 20-55 mg, about 20-50 mg, about 20-45 mg, about 20-40 mg, about 20-35 mg, about 20-30 mg, about 20-25 mg, about 25-60 mg, about 25-55 mg, about 25-50 mg, about 25-45 mg, about 25-40 mg, about 25-35 mg, about 25-30 mg, about 30-60 mg, about 30-55 mg, about 30-50 mg, about 30-45 mg, about 30-40 mg, about 30-35 mg, about 35-60 mg, about 35-55 mg, about 35-50 mg, about 35-45 mg, about 35-40 mg, about 40-60 mg, about 40-55 mg, about 40-50 mg, about 40-45 mg, about 45-60 mg, about 45-55 mg, about 45-50 mg, about 50-60 mg, about 50-55 mg, about 55-60 mg, about 0.2 mg, about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg) of a polypeptide consisting of SEQ ID NO: 17.

In some embodiments, such compositions comprise about 0.2-40 mg (e.g., about 0.2-40 mg, about 0.2-35 mg, about 0.2-30 mg, about 0.2-25 mg, about 0.2-20 mg, about 0.2-15 mg, about 0.2-10 mg, about 0.2-5 mg, about 0.2-2 mg, about 2-40 mg, about 2-35 mg, about 2-30 mg, about 2-25 mg, about 2-20 mg, about 2-15 mg, about 2-10 mg, about 2-5 mg, about 5-40 mg, about 5-35 mg, about 5-30 mg, about 5-25 mg, about 5-20 mg, about 5-15 mg, about 5-10 mg, about 10-40 mg, about 10-35 mg, about 10-30 mg, about 10-25 mg, about 10-20 mg, about 10-15 mg, about 15-40 mg, about 15-35 mg, about 15-30 mg, about 15-25 mg, about 15-20 mg, about 20-40 mg, about 20-35 mg, about 20-30 mg, about 20-25 mg, about 25-60 mg, about 25-55 mg, about 25-50 mg, about 25-45 mg, about 25-40 mg, about 25-35 mg, about 25-30 mg, about 30-40 mg, about 30-35 mg, about 35-40 mg, about 0.2 mg, about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg) of a polypeptide consisting of SEQ ID NO: 17.

It is contemplated that polypeptides, compositions, and methods of the present invention may be used to treat any type of articular cartilage damage (e.g., joint damage or injury), including, for example, damage arising from a traumatic event or tendon or ligament tear. In some embodiments, polypeptides, compositions and methods are used to treat joint damage (e.g., articular cartilage damage). In particular embodiments, joint damage is traumatic joint injury (e.g., traumatic cartilage damage). In other embodiments, joint damage or articular cartilage damage is damage arising from age or inactivity or genetic factors. In yet other embodiments joint damage or articular cartilage damage is damage arising from an autoimmune disorder. In some embodiments of the invention, polypeptides, compositions, and methods of the present invention may be used to treat osteoarthritis.

In some embodiments, polypeptides, compositions, and methods of the present invention provide a method for stimulating chondrocyte proliferation and/or cartilage production in cartilagenous tissues that have been damaged, e.g., due to traumatic injury or chondropathy. In particular embodiments polypeptides, compositions, and methods of the present invention are useful for treatment of cartilage damage in joints (e.g., articular cartilage damage), e.g., at articulated surfaces, e.g., spine, shoulder, elbow, wrist, joints of the fingers, hip, knee, ankle, and joints of the feet. Examples of diseases or disorders that may benefit from treatment include osteoarthritis, rheumatoid arthritis, other autoimmune diseases, or osteochondritis dessicans. In addition, cartilage damage or disruption occurs as a result of certain genetic or metabolic disorders, cartilage malformation is often seen in forms of dwarfism in humans, and/or cartilage damage or disruption is often a result of reconstructive surgery, thus polypeptides, compositions, and methods would be useful therapy in these patients, whether alone or in connection with other approaches.

It is further contemplated that polypeptides, compositions, and methods of the present invention may be used to treat various cartilagenous disorders and/or associated symptoms or effects of such conditions. Exemplary conditions or disorders for treatment with polypeptides, compositions, and methods described herein, include, but are not limited to rheumatoid arthritis, juvenile chronic arthritis, osteoarthritis, degenerative disc disease, spondyloarthropathies, Ehlers Danlos syndrome, systemic sclerosis (scleroderma) or tendon disease.

In some embodiments, polypeptides and compositions of the present invention are applied by direct injection into the synovial fluid of a joint, or directly into a cartilage defect. Polypeptides, compositions, and methods of the present invention can also be used in conjunction with a surgical procedure at an affected joint. Administration of a polypeptide of the invention may occur prior to, during or in conjunction with, and/or after a surgical procedure. For example, polypeptides, compositions and methods of the invention can be used to expand chondrocyte populations in culture for autologous or allogenic chondrocyte implantation. Chondrocytes can be optionally implanted with concurrent treatment consisting of administration of polypeptides and compositions of the present invention. In these procedures, for example, chondrocytes can be harvested arthroscopically from an uninjured minor load-bearing area of a damaged joint, and can be cultured in vitro, optionally in the presence of polypeptides and compositions of the present invention and/or other growth factors to increase the number of cells prior to transplantation. Expanded cultures are then optionally admixed with polypeptides and compositions of the present invention and/or placed in the joint space or directly into the defect. In certain embodiments, expanded cultures (optionally with polypeptides of the present invention) are placed in the joint space suspended in a matrix or membrane. In other embodiments, polypeptides and compositions of the present invention can be used in combination with one or more periosteal or perichondrial grafts that contain cartilage forming cells and/or help to hold the transplanted chondrocytes or chondrocyte precursor cells in place. In some embodiments, polypeptides and compositions of the present invention are used to repair cartilage damage (e.g., articular cartilage damage) in conjunction with other procedures, including but not limited to lavage of a joint, stimulation of bone marrow, abrasion arthroplasty, subchondral drilling, or microfracture of proximal subchondral bone. Optionally, following administration of polypeptides and compositions of the present invention and growth of cartilage, additional surgical treatment may be beneficial to suitably contour newly formed cartilage surface(s).

Pharmaceutical Composition

Provided here are also compositions, e.g., pharmaceutical compositions, comprising one or more protease-resistant ANGPTL3 polypeptides with chondrogenic activity described herein. Such compositions can comprise one or more excipients or carriers, e.g., a pharmaceutically acceptable excipient or carrier.

In some embodiments, pharmaceutical compositions that comprise a therapeutically effective amount of a protein or peptide in admixture are formulated with one or more pharmaceutically acceptable excipient or carrier, selected for suitability with the mode of administration, delivery format, and desired dosage.

In some embodiments, pharmaceutical compositions comprising a protease-resistant ANGPTL3 polypeptides with chondrogenic activity are suitable for intra-articular administration.

The pharmaceutical compositions may be in a variety of forms. These include, for example, liquid, semi-solid, or solid forms. The form depends on the intended mode of administration and therapeutic application. In some embodiments, the pharmaceutical composition is a liquid solution, e.g., an injectable solution. In some embodiments, the pharmaceutical composition is a powder, e.g., a lyophilisate. Lyophilized pharmaceutical compositions typically do not require particular conditions, such as refrigeration, for storage. Lyophilization is useful for developing pharmaceutical drug products that are reconstituted and administered to a patient by injection. For example, a lyophilized drug product can be reconstituted by adding a suitable administration diluent (e.g., sterile water) just prior to injection.

Provided herein are compositions, e.g., pharmaceutical compositions, comprising about 0.2-200 mg of a protease-resistant ANGPTL3 polypeptide with chondrogenic activity described herein. For example, such compositions can comprise about 0.2-200 mg, about 0.2-150 mg, about 0.2-120 mg, about 0.2-100 mg, about 0.2-90 mg, about 0.2-80 mg, about 0.2-70 mg, about 0.2-60 mg, about 0.2-50 mg, about 0.2-40 mg, about 0.2-30 mg, about 0.2-20 mg, about 0.2-10 mg, about 0.2-2 mg, about 2-200 mg, about 2-150 mg, about 2-120 mg, about 2-100 mg, about 2-90 mg, about 2-80 mg, about 2-70 mg, about 2-60 mg, about 2-50 mg, about 2-40 mg, about 2-30 mg, about 2-20 mg, about 2-10 mg, about 10-200 mg, about 10-150 mg, about 10-120 mg, about 10-100 mg, about 10-90 mg, about 10-80 mg, about 10-70 mg, about 10-60 mg, about 10-50 mg, about 10-40 mg, about 10-30 mg, about 10-20 mg, about 20-200 mg, about 20-150 mg, about 20-120 mg, about 20-100 mg, about 20-90 mg, about 20-80 mg, about 20-70 mg, about 20-60 mg, about 20-50 mg, about 20-40 mg, about 20-30 mg, about 40-200 mg, about 40-150 mg, about 40-120 mg, about 40-100 mg, about 40-90 mg, about 40-80 mg, about 40-70 mg, about 40-60 mg, about 40-50 mg, about 50-200 mg, about 50-150 mg, about 50-120 mg, about 50-100 mg, about 50-90 mg, about 50-80 mg, about 50-70 mg, about 50-60 mg, about 60-200 mg, about 60-150 mg, about 60-120 mg, about 60-100 mg, about 60-90 mg, about 60-80 mg, about 60-70 mg, about 70-200 mg, about 70-150 mg, about 70-120 mg, about 70-100 mg, about 70-90 mg, about 70-80 mg, about 80-200 mg, about 80-150 mg, about 80-120 mg, about 80-100 mg, about 80-90 mg, about 90-200 mg, about 90-150 mg, about 90-120 mg, about 90-100 mg, about 100-200 mg, about 100-150 mg, about 100-120 mg, about 120-200 mg, about 120-150 mg, about 150-200 mg, of a protease-resistant ANGPTL3 polypeptide with chondrogenic activity.

In some embodiments, provided herein are compositions, e.g., pharmaceutical compositions, comprising about 0.2-60 mg (e.g., about 0.2-60 mg, about 0.2-55 mg, about 0.2-50 mg, about 0.2-45 mg, about 0.2-40 mg, about 0.2-35 mg, about 0.2-30 mg, about 0.2-25 mg, about 0.2-20 mg, about 0.2-15 mg, about 0.2-10 mg, about 0.2-5 mg, about 0.2-2 mg, about 2-60 mg, about 2-55 mg, about 2-50 mg, about 2-45 mg, about 2-40 mg, about 2-35 mg, about 2-30 mg, about 2-25 mg, about 2-20 mg, about 2-15 mg, about 2-10 mg, about 2-5 mg, about 5-60 mg, about 5-55 mg, about 5-50 mg, about 5-45 mg, about 5-40 mg, about 5-35 mg, about 5-30 mg, about 5-25 mg, about 5-20 mg, about 5-15 mg, about 5-10 mg, about 10-60 mg, about 10-55 mg, about 10-50 mg, about 10-45 mg, about 10-40 mg, about 10-35 mg, about 10-30 mg, about 10-25 mg, about 10-20 mg, about 10-15 mg, about 15-60 mg, about 15-55 mg, about 15-50 mg, about 15-45 mg, about 15-40 mg, about 15-35 mg, about 15-30 mg, about 15-25 mg, about 15-20 mg, about 20-60 mg, about 20-55 mg, about 20-50 mg, about 20-45 mg, about 20-40 mg, about 20-35 mg, about 20-30 mg, about 20-25 mg, about 25-60 mg, about 25-55 mg, about 25-50 mg, about 25-45 mg, about 25-40 mg, about 25-35 mg, about 25-30 mg, about 30-60 mg, about 30-55 mg, about 30-50 mg, about 30-45 mg, about 30-40 mg, about 30-35 mg, about 35-60 mg, about 35-55 mg, about 35-50 mg, about 35-45 mg, about 35-40 mg, about 40-60 mg, about 40-55 mg, about 40-50 mg, about 40-45 mg, about 45-60 mg, about 45-55 mg, about 45-50 mg, about 50-60 mg, about 50-55 mg, about 55-60 mg, about 0.2 mg, about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg) of a protease-resistant ANGPTL3 polypeptide with chondrogenic activity described herein.

In some embodiments, provided herein are compositions, e.g., pharmaceutical compositions, comprising about 0.2-40 mg (e.g., about 0.2-40 mg, about 0.2-35 mg, about 0.2-30 mg, about 0.2-25 mg, about 0.2-20 mg, about 0.2-15 mg, about 0.2-10 mg, about 0.2-5 mg, about 0.2-2 mg, about 2-40 mg, about 2-35 mg, about 2-30 mg, about 2-25 mg, about 2-20 mg, about 2-15 mg, about 2-10 mg, about 2-5 mg, about 5-40 mg, about 5-35 mg, about 5-30 mg, about 5-25 mg, about 5-20 mg, about 5-15 mg, about 5-10 mg, about 10-40 mg, about 10-35 mg, about 10-30 mg, about 10-25 mg, about 10-20 mg, about 10-15 mg, about 15-40 mg, about 15-35 mg, about 15-30 mg, about 15-25 mg, about 15-20 mg, about 20-40 mg, about 20-35 mg, about 20-30 mg, about 20-25 mg, about 25-60 mg, about 25-55 mg, about 25-50 mg, about 25-45 mg, about 25-40 mg, about 25-35 mg, about 25-30 mg, about 30-40 mg, about 30-35 mg, about 35-40 mg, about 0.2 mg, about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg) of a protease-resistant ANGPTL3 polypeptide with chondrogenic activity described herein.

In some embodiments, the protease-resistant ANGPTL3 polypeptide comprises an amino acid sequence that has at least 95% identity, or at least 96%, 97%, 98%, or 99% identity, to an amino acid sequence listed in TABLE 1, wherein the polypeptide comprises an amino acid that is a polar amino acid other than K or R at position 423, as determined with reference to SEQ ID NO:1, and the polypeptide has chondrogenic activity. In some embodiments, the protease-resistant ANGPTL3 polypeptide comprises an amino acid sequence that has at least 95% identity, or at least 96%, 97%, 98%, or 99% identity, to an amino acid sequence listed in TABLE 1, wherein the amino acid residue corresponding to position 423 of SEQ ID NO: 1 is Q or S or deleted.

In some embodiments, the protease-resistant ANGPTL3 polypeptide comprises an amino acid sequence selected from any one of the sequences listed in TABLE 1. In some embodiments, the protease-resistant ANGPTL3 polypeptide consists of an amino acid sequence selected from any one of the sequences listed in TABLE 1. In some embodiments, the protease-resistant ANGPTL3 polypeptide comprises SEQ ID NO: 17. In some embodiments, the protease-resistant ANGPTL3 polypeptide consists of SEQ ID NO: 17.

In some embodiments, provided herein are compositions, e.g., pharmaceutical compositions, comprising about 0.2-60 mg (e.g., about 0.2-60 mg, about 0.2-55 mg, about 0.2-50 mg, about 0.2-45 mg, about 0.2-40 mg, about 0.2-35 mg, about 0.2-30 mg, about 0.2-25 mg, about 0.2-20 mg, about 0.2-15 mg, about 0.2-10 mg, about 0.2-5 mg, about 0.2-2 mg, about 2-60 mg, about 2-55 mg, about 2-50 mg, about 2-45 mg, about 2-40 mg, about 2-35 mg, about 2-30 mg, about 2-25 mg, about 2-20 mg, about 2-15 mg, about 2-10 mg, about 2-5 mg, about 5-60 mg, about 5-55 mg, about 5-50 mg, about 5-45 mg, about 5-40 mg, about 5-35 mg, about 5-30 mg, about 5-25 mg, about 5-20 mg, about 5-15 mg, about 5-10 mg, about 10-60 mg, about 10-55 mg, about 10-50 mg, about 10-45 mg, about 10-40 mg, about 10-35 mg, about 10-30 mg, about 10-25 mg, about 10-20 mg, about 10-15 mg, about 15-60 mg, about 15-55 mg, about 15-50 mg, about 15-45 mg, about 15-40 mg, about 15-35 mg, about 15-30 mg, about 15-25 mg, about 15-20 mg, about 20-60 mg, about 20-55 mg, about 20-50 mg, about 20-45 mg, about 20-40 mg, about 20-35 mg, about 20-30 mg, about 20-25 mg, about 25-60 mg, about 25-55 mg, about 25-50 mg, about 25-45 mg, about 25-40 mg, about 25-35 mg, about 25-30 mg, about 30-60 mg, about 30-55 mg, about 30-50 mg, about 30-45 mg, about 30-40 mg, about 30-35 mg, about 35-60 mg, about 35-55 mg, about 35-50 mg, about 35-45 mg, about 35-40 mg, about 40-60 mg, about 40-55 mg, about 40-50 mg, about 40-45 mg, about 45-60 mg, about 45-55 mg, about 45-50 mg, about 50-60 mg, about 50-55 mg, about 55-60 mg, about 0.2 mg, about 0.5 mg, about 1 mg, about 2 mg, about 3 mg, about 4 mg, about 5 mg, about 6 mg, about 7 mg, about 8 mg, about 9 mg, about 10 mg, about 1 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg) of a polypeptide comprising SEQ ID NO: 17.

In some embodiments, provided herein are compositions, e.g., pharmaceutical compositions, comprising about 0.2-60 mg (e.g., about 0.2-60 mg, about 0.2-55 mg, about 0.2-50 mg, about 0.2-45 mg, about 0.2-40 mg, about 0.2-35 mg, about 0.2-30 mg, about 0.2-25 mg, about 0.2-20 mg, about 0.2-15 mg, about 0.2-10 mg, about 0.2-5 mg, about 0.2-2 mg, about 2-60 mg, about 2-55 mg, about 2-50 mg, about 2-45 mg, about 2-40 mg, about 2-35 mg, about 2-30 mg, about 2-25 mg, about 2-20 mg, about 2-15 mg, about 2-10 mg, about 2-5 mg, about 5-60 mg, about 5-55 mg, about 5-50 mg, about 5-45 mg, about 5-40 mg, about 5-35 mg, about 5-30 mg, about 5-25 mg, about 5-20 mg, about 5-15 mg, about 5-10 mg, about 10-60 mg, about 10-55 mg, about 10-50 mg, about 10-45 mg, about 10-40 mg, about 10-35 mg, about 10-30 mg, about 10-25 mg, about 10-20 mg, about 10-15 mg, about 15-60 mg, about 15-55 mg, about 15-50 mg, about 15-45 mg, about 15-40 mg, about 15-35 mg, about 15-30 mg, about 15-25 mg, about 15-20 mg, about 20-60 mg, about 20-55 mg, about 20-50 mg, about 20-45 mg, about 20-40 mg, about 20-35 mg, about 20-30 mg, about 20-25 mg, about 25-60 mg, about 25-55 mg, about 25-50 mg, about 25-45 mg, about 25-40 mg, about 25-35 mg, about 25-30 mg, about 30-60 mg, about 30-55 mg, about 30-50 mg, about 30-45 mg, about 30-40 mg, about 30-35 mg, about 35-60 mg, about 35-55 mg, about 35-50 mg, about 35-45 mg, about 35-40 mg, about 40-60 mg, about 40-55 mg, about 40-50 mg, about 40-45 mg, about 45-60 mg, about 45-55 mg, about 45-50 mg, about 50-60 mg, about 50-55 mg, about 55-60 mg, about 0.2 mg, about 0.5 mg, about 1 mg, about 2 mg, about 3 mg, about 4 mg, about 5 mg, about 6 mg, about 7 mg, about 8 mg, about 9 mg, about 10 mg, about 1 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg) of a polypeptide consisting of SEQ ID NO: 17.

In some embodiments, provided herein are compositions, e.g., pharmaceutical compositions, comprising about 0.2-40 mg (e.g., about 0.2-40 mg, about 0.2-35 mg, about 0.2-30 mg, about 0.2-25 mg, about 0.2-20 mg, about 0.2-15 mg, about 0.2-10 mg, about 0.2-5 mg, about 0.2-2 mg, about 2-40 mg, about 2-35 mg, about 2-30 mg, about 2-25 mg, about 2-20 mg, about 2-15 mg, about 2-10 mg, about 2-5 mg, about 5-40 mg, about 5-35 mg, about 5-30 mg, about 5-25 mg, about 5-20 mg, about 5-15 mg, about 5-10 mg, about 10-40 mg, about 10-35 mg, about 10-30 mg, about 10-25 mg, about 10-20 mg, about 10-15 mg, about 15-40 mg, about 15-35 mg, about 15-30 mg, about 15-25 mg, about 15-20 mg, about 20-40 mg, about 20-35 mg, about 20-30 mg, about 20-25 mg, about 25-60 mg, about 25-55 mg, about 25-50 mg, about 25-45 mg, about 25-40 mg, about 25-35 mg, about 25-30 mg, about 30-40 mg, about 30-35 mg, about 35-40 mg, about 0.2 mg, about 0.5 mg, about 1 mg, about 2 mg, about 3 mg, about 4 mg, about 5 mg, about 6 mg, about 7 mg, about 8 mg, about 9 mg, about 10 mg, about 1 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg) of a polypeptide comprising SEQ ID NO: 17.

In some embodiments, provided herein are compositions, e.g., pharmaceutical compositions, comprising about 0.2-40 mg (e.g., about 0.2-40 mg, about 0.2-35 mg, about 0.2-30 mg, about 0.2-25 mg, about 0.2-20 mg, about 0.2-15 mg, about 0.2-10 mg, about 0.2-5 mg, about 0.2-2 mg, about 2-40 mg, about 2-35 mg, about 2-30 mg, about 2-25 mg, about 2-20 mg, about 2-15 mg, about 2-10 mg, about 2-5 mg, about 5-40 mg, about 5-35 mg, about 5-30 mg, about 5-25 mg, about 5-20 mg, about 5-15 mg, about 5-10 mg, about 10-40 mg, about 10-35 mg, about 10-30 mg, about 10-25 mg, about 10-20 mg, about 10-15 mg, about 15-40 mg, about 15-35 mg, about 15-30 mg, about 15-25 mg, about 15-20 mg, about 20-40 mg, about 20-35 mg, about 20-30 mg, about 20-25 mg, about 25-60 mg, about 25-55 mg, about 25-50 mg, about 25-45 mg, about 25-40 mg, about 25-35 mg, about 25-30 mg, about 30-40 mg, about 30-35 mg, about 35-40 mg, about 0.2 mg, about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg) of a polypeptide consisting of SEQ ID NO: 17.

In some embodiments, the compositions further comprise a carbohydrate. In some embodiments, the compositions further comprise a buffer or buffer component. In some embodiments, the compositions further comprises a surfactant, e.g., polysorbate 80.

In some embodiments, the compositions described herein contain a buffer or buffer component. Buffers are well known for pH control, both as a means to deliver a drug (e.g., a polypeptide) at a physiologically compatible pH (i.e., to improve tolerability), as well as to provide solution conditions favorable for chemical stability of a drug (e.g., a polypeptide).

Non-limiting examples of buffers that can be used in the compositions described herein include, histidine buffer, phosphate buffer, glycine buffer, acetate buffer, citrate buffer, lactate buffer, tartrate buffer, or hydrochloric acid buffer. In some embodiments, the compositions described herein include a buffer selected from a histidine buffer, a phosphate buffer, a glycine buffer, or an acetate buffer, or a component thereof. A preferred buffer is a histidine buffer, and a preferred buffer component is histidine.

pH can be critical in achieving an optimized protein composition, e.g., a liquid protein composition with increased stability. pH can work by affecting the conformation and/or aggregation and/or degradation and/or the reactivity of the protein. The pH is preferably less than 7.0, more preferably in the range of about 5.0 to about 7.0, more preferably about 5.5 to about 6.1, more preferably about 5.8. In some embodiments, the pH of the composition described herein is between 5.5 and 6.1, e.g., about 5.5, about 5.6, about 5.7, about 5.8, about 5.9, about 6.0, about 6.1. Preferably, the pH of the composition is about 5.8.

In some embodiments, a carbohydrate is included in the composition. A carbohydrate can cause the protein to be more compact, and for example, bury or otherwise hinder access to an active moiety. This can increase protein stability, e.g., by reducing protein aggregation.

In some embodiments, the compositions described herein contain a carbohydrate. Preferred carbohydrate is sucrose. Other preferred carbohydrate suitable for use include: trehalose, maltose, raffinose, glucose, sorbitol, dextran, cyclodextrin, or mannitol. Other suitable substances that can be used to stabilize the protein include: carbohydrates such as lactose and arabinose; polyols such as mannitol, glycerol, and xylitol; amino acids such as glycine, arginine, lysine, histidine, alanine, methionine, and leucine; and polymers such as PEG, poloxomers, dextran, polypropylene glycol, polysaccharides, methylcellulose, sodium carboxymethyl cellulose, polyvinyl pyrrolidone (PVP), hydrolyzed gelatin, and human albumin. In some embodiments, a combination of two or more of these carbohydrates (e.g., sucrose and trehalose) is used in the compositions described herein. The suitability of the combination can be tested for a candidate carbohydrate.

A surfactant can be added to the composition to increase protein stability, e.g., reduce protein degradation, e.g., due to air/liquid interface upon shaking/shipment. A surfactant that increases protein stability, e.g., does not cause protein degradation in a composition, is selected. A surfactant suitable for use is e.g., polysorbate 80.

EXAMPLES

The invention is further described in the following examples, which do not limit the scope of the invention described in the claims.

Example 1: Administration of ANGPTL3 Polypeptides to Primary Osteoarthritis Human Patients A randomized, placebo controlled, double-blind first-in-human single ascending dose study of the ANGPTL3 polypeptide of SEQ ID NO: 17 in primary osteoarthritis patients scheduled for total knee replacement (TKR) is ongoing.

The study design was shown in FIG. 1, which was designed to evaluate the safety and tolerability of ANGPTL3 polypeptide after one intra-articular (i.a.) injection into the knee joint of primary osteoarthritis (OA) patients prior to its removal at total knee replacement (TKR). About 28 patients are to be enrolled into seven cohorts. In each cohort, three patients are treated with ANGPTL3 polypeptide and one patient is treated with placebo. Cohort 1 patients were intra-articularly injected 0.2 mg/knee of the ANGPTL3 polypeptide or placebo about 7 days prior to TKR. Cohort 2 patients were intra-articularly injected 2 mg/knee of the ANGPTL3 polypeptide or placebo about 7 days prior to TKR. Cohort 3 patients were intra-articularly injected 10 mg/knee of the ANGPTL3 polypeptide or placebo about 7 days prior to TKR. Cohort 4 patients were intra-articularly injected 20 mg/knee of the ANGPTL3 polypeptide or placebo about 7 days prior to TKR. Dose and time before surgery for Cohorts 5-7 were selected based on analysis of Cohorts 1-4. Cohort 5 patients will be intra-articularly injected 20 mg/knee of the ANGPTL3 polypeptide or placebo about 2 hours prior to TKR. Cohort 6 patients will be intra-articularly injected 20 mg/knee of the ANGPTL3 polypeptide or placebo about 21 days prior to TKR. Cohort 7 patients will be intra-articularly injected 40 mg/knee of the ANGPTL3 polypeptide or placebo about 7 days prior to TKR. The patient population and Demographic information for Cohorts 1-4 are shown in Table 2 and Table 3.

The starting dose of 0.2 mg/knee for human patient was chosen based on safety and efficacy data obtained from rat and dog dosing studies and is expected to deliver a moderate pharmacological effect.

The 20 mg/knee dose for human patient was chosen based on the volume of joint synovial fluid and solubility of the ANGPTL3 polypeptide of SEQ ID NO: 17 in joint synovial fluid, and dog intra-articular dosing studies. The area of cartilage in a dog knee is estimated to be 196 mm$^2$; while the human knee cartilage area is estimated to be 1215 mm$^2$. Based on dog intra-articular dosing studies, the 20 mg/knee dose has an acceptable safety margin.

For the interim analysis, including all patients from Cohort 1 to 4 up to TKR surgery visit, all safety end points (including adverse events CTC-AE, physical exam, vital signs, ECG, safety laboratory and pain measured using KOOS) were measured up to and including 7 days post-dose. No adverse events was reported to be suspected to be related to the treatment.

In summary, no significant safety findings were observed in Cohorts 1-4. No immunogenicity was observed in the 16 patients administered with the ANGPTL3 polypeptide of SEQ ID NO: 17.

Since the tested dose of 20 mg/knee in Cohort 4 was well tolerated in all treated patients (N=3) without any specific safety concerns, a further dose escalation to 40 mg/knee is planned for Cohort 7. The estimated systemic exposures at the dose of 40 mg/knee will be still associated with an ample safety margin based on toxicity studies in dogs and rats (see Table 4). In addition to the high systemic safety margin, the rationale for including 40 mg/knee is also based on (i) the preclinical pharmacology studies which justify the need to investigate the safety of a potentially more efficacious dose for the ANGPTL3 polypeptide of SEQ ID NO: 17; (ii) the favorable safety profile of the ANGPTL3 polypeptide of SEQ ID NO: 17 up to 20 mg/knee, with no drug-related Adverse Events demonstrated to date; (iii) the local cartilage safety margin from dog studies (see Table 5).

TABLE 2

Patient Population.

| Population | 0.2 mg/knee N = 3 | 2 mg/knee N = 3 | 10 mg/knee N = 3 | 20 mg/knee N = 4* | Placebo** N = 5* |
|---|---|---|---|---|---|
| Randomized | 3 (100.0) | 3 (100.0) | 3 (100.0) | 4 (100.0) | 5 (100.0) |
| Safety analysis set | 3 (100.0) | 3 (100.0) | 3 (100.0) | 3 (75.0) | 4 (80.0) |
| PK analysis set | 3 (100.0) | 3 (100.0) | 3 (100.0) | 3 (75.0) | 4 (80.0) |
| Biomarker analysis set | 3 (100.0) | 3 (100.0) | 3 (100.0) | 3 (75.0) | 4 (80.0) |

*One subject each in 20 mg/knee group and Placebo group was randomized but withdrew consent prior dosing.

TABLE 3

Patient Demographics.

| Parameter | | 0.2 mg/knee N = 3 | 2 mg/knee N = 3 | 10 mg/knee N = 3 | 20 mg/knee N = 3 | Placebo** N = 4 | All Subjects N = 16 |
|---|---|---|---|---|---|---|---|
| Sex | Male | 2 (67%) | 2 (67%) | 0 | 1 (33%) | 1 (25%) | 6 (38%) |
| | Female | 1 (33%) | 1 (33%) | 3 (100%) | 2 (67%) | 3 (75%) | 10 (63%) |
| Age (years) | Mean (SD) | 57.7 (7.23) | 63.3 (3.79) | 67.7 (2.08) | 68.0 (5.20) | 60.3 (9.22) | 63.2 (6.86) |
| | Range | 53-66 | 59-66 | 66-70 | 65-74 | 51-73 | 51-74 |
| Weight (kg) | Mean (SD) | 92.4 (25.14) | 82.2 (1.60) | 70.1 (18.52) | 110.0 (21.21) | 98.2 (11.73) | 91.1 (20.18) |
| | Range | 64-113 | 81-84 | 54-91 | 91-133 | 85-113 | 54-133 |
| Height (cm) | Mean (SD) | 170.6 (10.18) | 174.5 (3.21) | 159.4 (6.85) | 169.3 (12.02) | 168.2 (15.57) | 168.4 (10.67) |
| | Range | 160-180 | 171-178 | 152-165 | 160-183 | 146-182 | 146-183 |
| BMI (kg/m$^2$) | Mean (SD) | 31.9 (8.97) | 27.0 (0.80) | 27.3 (5.16) | 38.1 (2.30) | 35.1 (5.22) | 32.1 (6.30) |
| | Range | 22-39 | 27-28 | 24-33 | 35-40 | 29-40 | 22-40 |

TABLE 4

Systemic Safety Margin

| Species | NOAEL* (mg/kg/day) | HED# (mg/kg/day) | Systemic safety margin at 0.2 mg/knee | Systemic safety margin at 20 mg/knee | Systemic safety margin at 40 mg/knee |
|---|---|---|---|---|---|
| Rat | 50 | 8.06 | 2820 | 28.2 | 14.1 |
| Dog | 20 | 11.1 | 3880 | 38.8 | 19.4 |

*NOAEL = no observed adverse effect level
HED = human equivalent dose

TABLE 5

Local Safety Margin

| Species | NOAEL* (mg/knee) | Tissue | Local safety margin at 0.2 mg/knee | Local safety margin at 20 mg/knee | Local safety margin at 40 mg/knee |
|---|---|---|---|---|---|
| Dog | 4 | Synovial fluid | 140 | 1.40 | 0.70 |
| Dog | 4 | Cartilage | 124 | 1.24 | 0.62 |

*NOAEL = no observed adverse effect level

Unless defined otherwise, the technical and scientific terms used herein have the same meaning as that usually understood by a specialist familiar with the field to which the disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein. Unless indicated otherwise, each of the references cited herein is incorporated in its entirety by reference.

Claims to the invention are non-limiting and are provided below.

Although particular aspects and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the disclosure without departing from the spirit and scope of the disclosure as defined by the claims. The choice of nucleic acid starting material, clone of interest, or library type is believed to be a matter of routine for a person of ordinary skill in the art with knowledge of the aspects described herein. Other aspects, advantages, and modifications considered to be within the scope of the following claims. Those skilled in the art will recognize or be able to ascertain, using no more than routine experimentation, many equivalents of the specific aspects of the invention described herein. Such equivalents are intended to be encompassed by the following claims. Redrafting of claim scope in later filed corresponding applications may be due to limitations by the patent laws of various countries and should not be interpreted as giving up subject matter of the claims.

The invention claimed is:

1. A method of treating arthritis or cartilage damage in a human subject, the method comprising administering to a joint of the human subject an intra-articular dose of about 20 mg of a polypeptide comprising the amino acid sequence of SEQ ID NO: 17, wherein the polypeptide has chondrogenic activity.

2. The method of claim 1, wherein the polypeptide is administered to the joint of the human subject in a single injection.

3. The method of claim 1, wherein administering the polypeptide occurs in conjunction with any one of bone marrow stimulation, cartilage replacement, autologous chondrocyte implantation (ACI), or matrix-induced autologous chondrocyte implantation (MACI).

4. The method of claim 1, wherein the human subject has osteoarthritis, traumatic arthritis, or autoimmune arthritis.

5. The method of claim 1, wherein the human subject has cartilage damage.

6. A method of treating arthritis or cartilage damage in a human subject, the method comprising administering to a joint of the human subject an intra-articular dose of about 40 mg of a polypeptide comprising the amino acid sequence of SEQ ID NO: 17, wherein the polypeptide has chondrogenic activity.

7. The method of claim 6, wherein the polypeptide is administered to the joint of the human subject in a single injection.

8. The method of claim 6, wherein administering the polypeptide occurs in conjunction with any one of bone marrow stimulation, cartilage replacement, autologous chondrocyte implantation (ACI), or matrix-induced autologous chondrocyte implantation (MACI).

9. The method of claim 6, wherein the human subject has osteoarthritis, traumatic arthritis, or autoimmune arthritis.

10. The method of claim 6, wherein the human subject has cartilage damage.

11. A method of treating arthritis or cartilage damage in a human subject, the method comprising administering to a joint of the human subject an intra-articular dose of about 60 mg of a polypeptide comprising the amino acid sequence of SEQ ID NO: 17, wherein the polypeptide has chondrogenic activity.

12. The method of claim 11, wherein the polypeptide is administered to the joint of the human subject in a single injection.

13. The method of claim 11, wherein administering the polypeptide occurs in conjunction with any one of bone marrow stimulation, cartilage replacement, autologous chondrocyte implantation (ACI), or matrix-induced autologous chondrocyte implantation (MACI).

14. The method of claim 11, wherein the human subject has osteoarthritis, traumatic arthritis, or autoimmune arthritis.

15. The method of claim 11, wherein the human subject has cartilage damage.

* * * * *

SEQUENCE LISTING

```
<160> NUMBER OF SEQ ID NOS: 44

<210> SEQ ID NO 1
<211> LENGTH: 460
<212> TYPE: PRT
<213> ORGANISM: Homo sapiens

<400> SEQUENCE: 1

Met Phe Thr Ile Lys Leu Leu Leu Phe Ile Val Pro Leu Val Ile Ser
1               5                   10                  15

Ser Arg Ile Asp Gln Asp Asn Ser Ser Phe Asp Ser Leu Ser Pro Glu
                20                  25                  30

Pro Lys Ser Arg Phe Ala Met Leu Asp Asp Val Lys Ile Leu Ala Asn
            35                  40                  45

Gly Leu Leu Gln Leu Gly His Gly Leu Lys Asp Phe Val His Lys Thr
        50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu Glu
                85                  90                  95

Lys Glu Leu Arg Arg Thr Thr Tyr Lys Leu Gln Val Lys Asn Glu Glu
                100                 105                 110

Val Lys Asn Met Ser Leu Glu Leu Asn Ser Lys Leu Glu Ser Leu Leu
```

```
                    115                 120                 125
Glu Glu Lys Ile Leu Gln Gln Lys Val Lys Tyr Leu Glu Glu Gln
            130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Leu Leu Gln Thr Val Glu Asp Gln Tyr Lys Gln Leu Asn Gln Gln
            180                 185                 190

His Ser Gln Ile Lys Glu Ile Glu Asn Gln Leu Arg Arg Thr Ser Ile
        195                 200                 205

Gln Glu Pro Thr Glu Ile Ser Leu Ser Ser Lys Pro Arg Ala Pro Arg
    210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
        275                 280                 285

Ile Asp Gly Ser Gln Asn Phe Asn Glu Thr Trp Glu Asn Tyr Lys Tyr
    290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
        355                 360                 365

Val Pro Asn Ala Ile Pro Glu Asn Lys Asp Leu Val Phe Ser Thr Trp
    370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Lys Ser Lys Pro Glu Arg Arg Arg Gly Leu
            420                 425                 430

Ser Trp Lys Ser Gln Asn Gly Arg Leu Tyr Ser Ile Lys Ser Thr Lys
        435                 440                 445

Met Leu Ile His Pro Thr Asp Ser Glu Ser Phe Glu
    450                 455                 460

<210> SEQ ID NO 2
<211> LENGTH: 2951
<212> TYPE: DNA
<213> ORGANISM: Homo sapiens

<400> SEQUENCE: 2
atatatagag ttaagaagtc taggtctgct tccagaagaa aacagttcca cgttgcttga      60
aattgaaaat caagataaaa atgttcacaa ttagctcct tctttttatt gttcctctag     120
ttatttcctc cagaattgat caagacaatt catcatttga ttctctatct ccagagccaa    180
```

```
aatcaagatt tgctatgtta gacgatgtaa aaattttagc caatggcctc cttcagttgg      240
gacatggtct taaagacttt gtccataaga cgaagggcca aattaatgac atatttcaaa      300
aactcaacat atttgatcag tcttttatg atctatcgct gcaaaccagt gaaatcaaag       360
aagaagaaaa ggaactgaga agaactacat ataaactaca agtcaaaaat gaagaggtaa      420
agaatatgtc acttgaactc aactcaaaac ttgaaagcct cctagaagaa aaaattctac      480
ttcaacaaaa agtgaaatat ttagaagagc aactaactaa cttaattcaa aatcaacctg      540
aaactccaga acacccagaa gtaacttcac ttaaaacttt tgtagaaaaa caagataata      600
gcatcaaaga ccttctccag accgtggaag accaatataa acaattaaac caacagcata      660
gtcaaataaa agaaatagaa aatcagctca gaaggactag tattcaagaa cccacagaaa      720
tttctctatc ttccaagcca agagcaccaa gaactactcc cttcttcag ttgaatgaaa        780 taagaaatgt aaaacatgat ggcattcctg ctgaatgtac caccatttat aacagaggtg      840
aacatacaag tggcatgtat gccatcagac ccagcaactc tcaagttttt catgtctact      900
gtgatgttat atcaggtagt ccatggacat taattcaaca tcgaatagat ggatcacaaa      960
acttcaatga aacgtgggag aactacaaat atggttttgg gaggcttgat ggagaatttt     1020
ggttgggcct agagaagata tactccatag tgaagcaatc taattatgtt ttacgaattg      1080
agttggaaga ctggaaagac aacaaacatt atattgaata ttcttttta cttgggaaatc      1140 acgaaaccaa ctatacgcta catctagttg cgattactgg caatgtcccc aatgcaatcc      1200
cggaaaacaa agatttggtg ttttctactt gggatcacaa agcaaaagga cacttcaact      1260
gtccagaggg ttattcagga ggctggtggt ggcatgatga gtgtggagaa acaacctaa        1320 atggtaaata taacaaacca agagcaaaat ctaagccaga gaggagaaga ggattatctt      1380
ggaagtctca aaatggaagg ttatactcta taaaatcaac caaaatgttg atccatccaa      1440
cagattcaga aagctttgaa tgaactgagg caaatttaaa aggcaataat ttaaacatta      1500
acctcattcc aagttaatgt ggtctaataa tctggtatta aatccttaag agaaagcttg      1560
agaaatagat ttttttatc ttaaagtcac tgtctattta agattaaaca tacaatcaca       1620
taaccttaaa gaataccgtt tacatttctc aatcaaaatt cttataatac tatttgtttt      1680
aaattttgtg atgtgggaat caattttaga tggtcacaat ctagattata atcaataggt      1740
gaacttatta ataacttttt ctaaataaaa aatttagaga cttttatttt aaaaggcatc      1800
atatgagcta atatcacaac tttcccagtt taaaaaacta gtactcttgt taaaactcta      1860
aacttgacta aatacagagg actggtaatt gtacagttct taaatgttgt agtattaatt      1920
tcaaaactaa aaatcgtcag cacagagtat gtgtaaaaat ctgtaataca aattttaaa      1980 ctgatgcttc attttgctac aaaataattt ggagtaaatg tttgatatga tttatttatg     2040
aaacctaatg aagcagaatt aaatactgta ttaaaataag ttcgctgtct ttaaacaaat     2100
ggagatgact actaagtcac attgacttta acatgaggta tcactatacc ttatttgtta      2160
aaatatatac tgtatacatt ttatatattt taacacttaa tactatgaaa acaaataatt      2220
gtaaaggaat cttgtcagat tacagtaaga atgaacatat tgtggcatc gagttaaagt       2280 ttatatttcc cctaaatatg ctgtgattct aatacattcg tgtaggtttt caagtagaaa      2340
taaacctcgt aacaagttac tgaacgttta aacagcctga caagcatgta tatatgttta     2400
aaattcaata aacaaagacc cagtcccctaa attatagaaa tttaaattat tcttgcatgt    2460
ttatcgacat cacaacagat ccctaaatcc ctaaatccct aaagattaga tacaaatttt    2520
ttaccacagt atcacttgtc agaatttatt tttaaatatg attttttaaa actgccagta      2580
```

-continued

```
agaaatttta aattaaaccc atttgttaaa ggatatagtg cccaagttat atggtgacct    2640 accttttgtca atacttagca ttatgtattt caaattatcc aatatacatg tcatatatat    2700
ttttatatgt cacatatata aaagatatgt atgatctatg tgaatcctaa gtaaatattt    2760
tgttccagaa aagtacaaaa taataaaggt aaaaataatc tataatttc aggaccacag     2820 actaagctgt cgaaattaac gctgattttt ttagggccag aataccaaaa tggctcctct    2880
cttcccccaa aattggacaa tttcaaatgc aaaataattc attatttaat atatgagttg    2940
cttcctctat t                                                         2951
```

<210> SEQ ID NO 3
<211> LENGTH: 253
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 3

```
Ile Gln Glu Pro Thr Glu Ile Ser Leu Ser Ser Lys Pro Arg Ala Pro
1               5                  10                  15

Arg Thr Thr Pro Phe Leu Gln Leu Asn Glu Ile Arg Asn Val Lys His
            20                  25                  30

Asp Gly Ile Pro Ala Glu Cys Thr Thr Ile Tyr Asn Arg Gly Glu His
        35                  40                  45

Thr Ser Gly Met Tyr Ala Ile Arg Pro Ser Asn Ser Gln Val Phe His
    50                  55                  60

Val Tyr Cys Asp Val Ile Ser Gly Ser Pro Trp Thr Leu Ile Gln His
65                  70                  75                  80

Arg Ile Asp Gly Ser Gln Asn Phe Asn Glu Thr Trp Glu Asn Tyr Lys
                85                  90                  95

Tyr Gly Phe Gly Arg Leu Asp Gly Glu Phe Trp Leu Gly Leu Glu Lys
            100                 105                 110

Ile Tyr Ser Ile Val Lys Gln Ser Asn Tyr Val Leu Arg Ile Glu Leu
        115                 120                 125

Glu Asp Trp Lys Asp Asn Lys His Tyr Ile Glu Tyr Ser Phe Tyr Leu
    130                 135                 140

Gly Asn His Glu Thr Asn Tyr Thr Leu His Leu Val Ala Ile Thr Gly
145                 150                 155                 160

Asn Val Pro Asn Ala Ile Pro Glu Asn Lys Asp Leu Val Phe Ser Thr
                165                 170                 175

Trp Asp His Lys Ala Lys Gly His Phe Asn Cys Pro Glu Gly Tyr Ser
            180                 185                 190

Gly Gly Trp Trp Trp His Asp Glu Cys Gly Glu Asn Asn Leu Asn Gly
        195                 200                 205

Lys Tyr Asn Lys Pro Arg Ala Gln Ser Lys Pro Glu Arg Arg Arg Gly
    210                 215                 220

Leu Ser Trp Lys Ser Gln Asn Gly Arg Leu Tyr Ser Ile Lys Ser Thr
225                 230                 235                 240

Lys Met Leu Ile His Pro Thr Asp Ser Glu Ser Phe Glu
                245                 250
```

<210> SEQ ID NO 4
<211> LENGTH: 253
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Ile Gln Glu Pro Thr Glu Ile Ser Leu Ser Ser Lys Pro Arg Ala Pro
1               5                   10                  15

Arg Thr Thr Pro Phe Leu Gln Leu Asn Glu Ile Arg Asn Val Lys His
                20                  25                  30

Asp Gly Ile Pro Ala Glu Cys Thr Thr Ile Tyr Asn Arg Gly Glu His
            35                  40                  45

Thr Ser Gly Met Tyr Ala Ile Arg Pro Ser Asn Ser Gln Val Phe His
    50                  55                  60

Val Tyr Cys Asp Val Ile Ser Gly Ser Pro Trp Thr Leu Ile Gln His
65                  70                  75                  80

Arg Ile Asp Gly Ser Gln Asn Phe Asn Glu Thr Trp Glu Asn Tyr Lys
                85                  90                  95

Tyr Gly Phe Gly Arg Leu Asp Gly Glu Phe Trp Leu Gly Leu Glu Lys
                100                 105                 110

Ile Tyr Ser Ile Val Lys Gln Ser Asn Tyr Val Leu Arg Ile Glu Leu
            115                 120                 125

Glu Asp Trp Lys Asp Asn Lys His Tyr Ile Glu Tyr Ser Phe Tyr Leu
    130                 135                 140

Gly Asn His Glu Thr Asn Tyr Thr Leu His Leu Val Ala Ile Thr Gly
145                 150                 155                 160

Asn Val Pro Asn Ala Ile Pro Glu Asn Lys Asp Leu Val Phe Ser Thr
                165                 170                 175

Trp Asp His Lys Ala Lys Gly His Phe Asn Cys Pro Glu Gly Tyr Ser
                180                 185                 190

Gly Gly Trp Trp Trp His Asp Glu Cys Gly Glu Asn Asn Leu Asn Gly
            195                 200                 205

Lys Tyr Asn Lys Pro Arg Ala Ser Ser Lys Pro Glu Arg Arg Arg Gly
    210                 215                 220

Leu Ser Trp Lys Ser Gln Asn Gly Arg Leu Tyr Ser Ile Lys Ser Thr
225                 230                 235                 240

Lys Met Leu Ile His Pro Thr Asp Ser Glu Ser Phe Glu
                245                 250

<210> SEQ ID NO 5
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Thr Thr Pro Phe Leu Gln Leu Asn Glu Ile Arg Asn Val Lys His Asp
1               5                   10                  15

Gly Ile Pro Ala Glu Cys Thr Thr Ile Tyr Asn Arg Gly Glu His Thr
                20                  25                  30

Ser Gly Met Tyr Ala Ile Arg Pro Ser Asn Ser Gln Val Phe His Val
            35                  40                  45

Tyr Cys Asp Val Ile Ser Gly Ser Pro Trp Thr Leu Ile Gln His Arg
    50                  55                  60
```

Ile Asp Gly Ser Gln Asn Phe Asn Glu Thr Trp Glu Asn Tyr Lys Tyr
65                  70                  75                  80

Gly Phe Gly Arg Leu Asp Gly Glu Phe Trp Leu Gly Leu Glu Lys Ile
                85                  90                  95

Tyr Ser Ile Val Lys Gln Ser Asn Tyr Val Leu Arg Ile Glu Leu Glu
            100                 105                 110

Asp Trp Lys Asp Asn Lys His Tyr Ile Glu Tyr Ser Phe Tyr Leu Gly
            115                 120                 125

Asn His Glu Thr Asn Tyr Thr Leu His Leu Val Ala Ile Thr Gly Asn
        130                 135                 140

Val Pro Asn Ala Ile Pro Glu Asn Lys Asp Leu Val Phe Ser Thr Trp
145                 150                 155                 160

Asp His Lys Ala Lys Gly His Phe Asn Cys Pro Glu Gly Tyr Ser Gly
                165                 170                 175

Gly Trp Trp Trp His Asp Glu Cys Gly Glu Asn Asn Leu Asn Gly Lys
                180                 185                 190

Tyr Asn Lys Pro Arg Ala Gln Ser Lys Pro Glu Arg Arg Arg Gly Leu
            195                 200                 205

Ser Trp Lys Ser Gln Asn Gly Arg Leu Tyr Ser Ile Lys Ser Thr Lys
        210                 215                 220

Met Leu Ile His Pro Thr Asp Ser Glu Ser Phe Glu
225                 230                 235

<210> SEQ ID NO 6
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Thr Thr Pro Phe Leu Gln Leu Asn Glu Ile Arg Asn Val Lys His Asp
1               5                   10                  15

Gly Ile Pro Ala Glu Cys Thr Thr Ile Tyr Asn Arg Gly Glu His Thr
            20                  25                  30

Ser Gly Met Tyr Ala Ile Arg Pro Ser Asn Ser Gln Val Phe His Val
        35                  40                  45

Tyr Cys Asp Val Ile Ser Gly Ser Pro Trp Thr Leu Ile Gln His Arg
    50                  55                  60

Ile Asp Gly Ser Gln Asn Phe Asn Glu Thr Trp Glu Asn Tyr Lys Tyr
65                  70                  75                  80

Gly Phe Gly Arg Leu Asp Gly Glu Phe Trp Leu Gly Leu Glu Lys Ile
                85                  90                  95

Tyr Ser Ile Val Lys Gln Ser Asn Tyr Val Leu Arg Ile Glu Leu Glu
            100                 105                 110

Asp Trp Lys Asp Asn Lys His Tyr Ile Glu Tyr Ser Phe Tyr Leu Gly
            115                 120                 125

Asn His Glu Thr Asn Tyr Thr Leu His Leu Val Ala Ile Thr Gly Asn
        130                 135                 140

Val Pro Asn Ala Ile Pro Glu Asn Lys Asp Leu Val Phe Ser Thr Trp
145                 150                 155                 160

Asp His Lys Ala Lys Gly His Phe Asn Cys Pro Glu Gly Tyr Ser Gly
                165                 170                 175

```
Gly Trp Trp Trp His Asp Glu Cys Gly Glu Asn Asn Leu Asn Gly Lys
            180                 185                 190

Tyr Asn Lys Pro Arg Ala Ser Ser Lys Pro Glu Arg Arg Gly Leu
            195                 200                 205

Ser Trp Lys Ser Gln Asn Gly Arg Leu Tyr Ser Ile Lys Ser Thr Lys
210                 215                 220

Met Leu Ile His Pro Thr Asp Ser Glu Ser Phe Glu
225                 230                 235
```

<210> SEQ ID NO 7
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Thr Thr Pro Phe Leu Gln Leu Asn Glu Ile Arg Asn Val Lys His Asp
1               5                   10                  15

Gly Ile Pro Ala Glu Cys Thr Thr Ile Tyr Asn Arg Gly Glu His Thr
            20                  25                  30

Ser Gly Met Tyr Ala Ile Arg Pro Ser Asn Ser Gln Val Phe His Val
        35                  40                  45

Tyr Cys Asp Val Ile Ser Ser Pro Trp Thr Leu Ile Gln His Arg
50                  55                  60

Ile Asp Gly Ser Gln Asn Phe Asn Glu Thr Trp Glu Asn Tyr Lys Tyr
65                  70                  75                  80

Gly Phe Gly Arg Leu Asp Gly Glu Phe Trp Leu Gly Leu Glu Lys Ile
            85                  90                  95

Tyr Ser Ile Val Lys Gln Ser Asn Tyr Val Leu Arg Ile Glu Leu Glu
            100                 105                 110

Asp Trp Lys Asp Asn Lys His Tyr Ile Glu Tyr Ser Phe Tyr Leu Gly
            115                 120                 125

Asn His Glu Thr Asn Tyr Thr Leu His Leu Val Ala Ile Thr Gly Asn
130                 135                 140

Val Pro Asn Ala Ile Pro Glu Asn Lys Asp Leu Val Phe Ser Thr Trp
145                 150                 155                 160

Asp His Lys Ala Lys Gly His Phe Asn Cys Pro Glu Gly Tyr Ser Gly
            165                 170                 175

Gly Trp Trp Trp His Asp Glu Cys Gly Glu Asn Asn Leu Asn Gly Lys
            180                 185                 190

Tyr Asn Lys Pro Arg Ala Lys Thr Lys Pro Glu Arg Arg Gly Leu
            195                 200                 205

Ser Trp Lys Ser Gln Asn Gly Arg Leu Tyr Ser Ile Lys Ser Thr Lys
210                 215                 220

Met Leu Ile His Pro Thr Asp Ser Glu Ser Phe Glu
225                 230                 235
```

<210> SEQ ID NO 8
<211> LENGTH: 235
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

```
<400> SEQUENCE: 8

Thr Pro Phe Leu Gln Leu Asn Glu Ile Arg Asn Val Lys His Asp Gly
1               5                   10                  15

Ile Pro Ala Glu Cys Thr Thr Ile Tyr Asn Arg Gly Glu His Thr Ser
            20                  25                  30

Gly Met Tyr Ala Ile Arg Pro Ser Asn Ser Gln Val Phe His Val Tyr
        35                  40                  45

Cys Asp Val Ile Ser Gly Ser Pro Trp Thr Leu Ile Gln His Arg Ile
50                  55                  60

Asp Gly Ser Gln Asn Phe Asn Glu Thr Trp Glu Asn Tyr Lys Tyr Gly
65                  70                  75                  80

Phe Gly Arg Leu Asp Gly Glu Phe Trp Leu Gly Leu Glu Lys Ile Tyr
                85                  90                  95

Ser Ile Val Lys Gln Ser Asn Tyr Val Leu Arg Ile Glu Leu Glu Asp
            100                 105                 110

Trp Lys Asp Asn Lys His Tyr Ile Glu Tyr Ser Phe Tyr Leu Gly Asn
        115                 120                 125

His Glu Thr Asn Tyr Thr Leu His Leu Val Ala Ile Thr Gly Asn Val
130                 135                 140

Pro Asn Ala Ile Pro Glu Asn Lys Asp Leu Val Phe Ser Thr Trp Asp
145                 150                 155                 160

His Lys Ala Lys Gly His Phe Asn Cys Pro Glu Gly Tyr Ser Gly Gly
                165                 170                 175

Trp Trp Trp His Asp Glu Cys Gly Glu Asn Asn Leu Asn Gly Lys Tyr
            180                 185                 190

Asn Lys Pro Arg Ala Gln Ser Lys Pro Glu Arg Arg Arg Gly Leu Ser
        195                 200                 205

Trp Lys Ser Gln Asn Gly Arg Leu Tyr Ser Ile Lys Ser Thr Lys Met
210                 215                 220

Leu Ile His Pro Thr Asp Ser Glu Ser Phe Glu
225                 230                 235

<210> SEQ ID NO 9
<211> LENGTH: 235
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Thr Pro Phe Leu Gln Leu Asn Glu Ile Arg Asn Val Lys His Asp Gly
1               5                   10                  15

Ile Pro Ala Glu Cys Thr Thr Ile Tyr Asn Arg Gly Glu His Thr Ser
            20                  25                  30

Gly Met Tyr Ala Ile Arg Pro Ser Asn Ser Gln Val Phe His Val Tyr
        35                  40                  45

Cys Asp Val Ile Ser Gly Ser Pro Trp Thr Leu Ile Gln His Arg Ile
50                  55                  60

Asp Gly Ser Gln Asn Phe Asn Glu Thr Trp Glu Asn Tyr Lys Tyr Gly
65                  70                  75                  80

Phe Gly Arg Leu Asp Gly Glu Phe Trp Leu Gly Leu Glu Lys Ile Tyr
                85                  90                  95

Ser Ile Val Lys Gln Ser Asn Tyr Val Leu Arg Ile Glu Leu Glu Asp
            100                 105                 110
```

```
Trp Lys Asp Asn Lys His Tyr Ile Glu Tyr Ser Phe Tyr Leu Gly Asn
            115                 120                 125

His Glu Thr Asn Tyr Thr Leu His Leu Val Ala Ile Thr Gly Asn Val
        130                 135                 140

Pro Asn Ala Ile Pro Glu Asn Lys Asp Leu Val Phe Ser Thr Trp Asp
145                 150                 155                 160

His Lys Ala Lys Gly His Phe Asn Cys Pro Glu Gly Tyr Ser Gly Gly
                165                 170                 175

Trp Trp Trp His Asp Glu Cys Gly Glu Asn Asn Leu Asn Gly Lys Tyr
            180                 185                 190

Asn Lys Pro Arg Ala Ser Ser Lys Pro Glu Arg Arg Gly Leu Ser
                195                 200                 205

Trp Lys Ser Gln Asn Gly Arg Leu Tyr Ser Ile Lys Ser Thr Lys Met
            210                 215                 220

Leu Ile His Pro Thr Asp Ser Glu Ser Phe Glu
225                 230                 235

<210> SEQ ID NO 10
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Phe Leu Gln Leu Asn Glu Ile Arg Asn Val Lys His Asp Gly Ile Pro
1               5                   10                  15

Ala Glu Cys Thr Thr Ile Tyr Asn Arg Gly Glu His Thr Ser Gly Met
            20                  25                  30

Tyr Ala Ile Arg Pro Ser Asn Ser Gln Val Phe His Val Tyr Cys Asp
        35                  40                  45

Val Ile Ser Gly Ser Pro Trp Thr Leu Ile Gln His Arg Ile Asp Gly
    50                  55                  60

Ser Gln Asn Phe Asn Glu Thr Trp Glu Asn Tyr Lys Tyr Gly Phe Gly
65                  70                  75                  80

Arg Leu Asp Gly Glu Phe Trp Leu Gly Leu Glu Lys Ile Tyr Ser Ile
                85                  90                  95

Val Lys Gln Ser Asn Tyr Val Leu Arg Ile Glu Leu Glu Asp Trp Lys
            100                 105                 110

Asp Asn Lys His Tyr Ile Glu Tyr Ser Phe Tyr Leu Gly Asn His Glu
        115                 120                 125

Thr Asn Tyr Thr Leu His Leu Val Ala Ile Thr Gly Asn Val Pro Asn
    130                 135                 140

Ala Ile Pro Glu Asn Lys Asp Leu Val Phe Ser Thr Trp Asp His Lys
145                 150                 155                 160

Ala Lys Gly His Phe Asn Cys Pro Glu Gly Tyr Ser Gly Gly Trp Trp
                165                 170                 175

Trp His Asp Glu Cys Gly Glu Asn Asn Leu Asn Gly Lys Tyr Asn Lys
            180                 185                 190

Pro Arg Ala Gln Ser Lys Pro Glu Arg Arg Arg Gly Leu Ser Trp Lys
        195                 200                 205

Ser Gln Asn Gly Arg Leu Tyr Ser Ile Lys Ser Thr Lys Met Leu Ile
    210                 215                 220
```

```
His Pro Thr Asp Ser Glu Ser Phe Glu
225                 230
```

<210> SEQ ID NO 11
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

```
Phe Leu Gln Leu Asn Glu Ile Arg Asn Val Lys His Asp Gly Ile Pro
1               5                   10                  15

Ala Glu Cys Thr Thr Ile Tyr Asn Arg Gly Glu His Thr Ser Gly Met
            20                  25                  30

Tyr Ala Ile Arg Pro Ser Asn Ser Gln Val Phe His Val Tyr Cys Asp
        35                  40                  45

Val Ile Ser Gly Ser Pro Trp Thr Leu Ile Gln His Arg Ile Asp Gly
    50                  55                  60

Ser Gln Asn Phe Asn Glu Thr Trp Glu Asn Tyr Lys Tyr Gly Phe Gly
65                  70                  75                  80

Arg Leu Asp Gly Glu Phe Trp Leu Gly Leu Glu Lys Ile Tyr Ser Ile
                85                  90                  95

Val Lys Gln Ser Asn Tyr Val Leu Arg Ile Glu Leu Glu Asp Trp Lys
            100                 105                 110

Asp Asn Lys His Tyr Ile Glu Tyr Ser Phe Tyr Leu Gly Asn His Glu
        115                 120                 125

Thr Asn Tyr Thr Leu His Leu Val Ala Ile Thr Gly Asn Val Pro Asn
    130                 135                 140

Ala Ile Pro Glu Asn Lys Asp Leu Val Phe Ser Thr Trp Asp His Lys
145                 150                 155                 160

Ala Lys Gly His Phe Asn Cys Pro Glu Gly Tyr Ser Gly Gly Trp Trp
                165                 170                 175

Trp His Asp Glu Cys Gly Glu Asn Asn Leu Asn Gly Lys Tyr Asn Lys
            180                 185                 190

Pro Arg Ala Ser Ser Lys Pro Glu Arg Arg Arg Gly Leu Ser Trp Lys
        195                 200                 205

Ser Gln Asn Gly Arg Leu Tyr Ser Ile Lys Ser Thr Lys Met Leu Ile
    210                 215                 220

His Pro Thr Asp Ser Glu Ser Phe Glu
225                 230
```

<210> SEQ ID NO 12
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

```
Phe Leu Gln Leu Asn Glu Ile Arg Asn Val Lys His Asp Gly Ile Pro
1               5                   10                  15

Ala Glu Cys Thr Thr Ile Tyr Asn Arg Gly Glu His Thr Ser Gly Met
            20                  25                  30

Tyr Ala Ile Arg Pro Ser Asn Ser Gln Val Phe His Val Tyr Cys Asp
```

```
                35                  40                  45
Val Ile Ser Gly Ser Pro Trp Thr Leu Ile Gln His Arg Ile Asp Gly
 50                  55                  60

Ser Gln Asn Phe Asn Glu Thr Trp Glu Asn Tyr Lys Tyr Gly Phe Gly
 65                  70                  75                  80

Arg Leu Asp Gly Glu Phe Trp Leu Gly Leu Glu Lys Ile Tyr Ser Ile
                 85                  90                  95

Val Lys Gln Ser Asn Tyr Val Leu Arg Ile Glu Leu Glu Asp Trp Lys
                100                 105                 110

Asp Asn Lys His Tyr Ile Glu Tyr Ser Phe Tyr Leu Gly Asn His Glu
            115                 120                 125

Thr Asn Tyr Thr Leu His Leu Val Ala Ile Thr Gly Asn Val Pro Asn
130                 135                 140

Ala Ile Pro Glu Asn Lys Asp Leu Val Phe Ser Thr Trp Asp His Lys
145                 150                 155                 160

Ala Lys Gly His Phe Asn Cys Pro Glu Gly Tyr Ser Gly Gly Trp Trp
                165                 170                 175

Trp His Asp Glu Cys Gly Glu Asn Asn Leu Asn Gly Lys Tyr Asn Lys
            180                 185                 190

Pro Arg Ala Lys Thr Lys Pro Glu Arg Arg Gly Leu Ser Trp Lys
        195                 200                 205

Ser Gln Asn Gly Arg Leu Tyr Ser Ile Lys Ser Thr Lys Met Leu Ile
    210                 215                 220

His Pro Thr Asp Ser Glu Ser Phe Glu
225                 230
```

<210> SEQ ID NO 13
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 13

```
Glu Ile Arg Asn Val Lys His Asp Gly Ile Pro Ala Glu Cys Thr Thr
 1               5                  10                  15

Ile Tyr Asn Arg Gly Glu His Thr Ser Gly Met Tyr Ala Ile Arg Pro
                20                  25                  30

Ser Asn Ser Gln Val Phe His Val Tyr Cys Asp Val Ile Ser Gly Ser
             35                  40                  45

Pro Trp Thr Leu Ile Gln His Arg Ile Asp Gly Ser Gln Asn Phe Asn
 50                  55                  60

Glu Thr Trp Glu Asn Tyr Lys Tyr Gly Phe Gly Arg Leu Asp Gly Glu
 65                  70                  75                  80

Phe Trp Leu Gly Leu Glu Lys Ile Tyr Ser Ile Val Lys Gln Ser Asn
                 85                  90                  95

Tyr Val Leu Arg Ile Glu Leu Glu Asp Trp Lys Asp Asn Lys His Tyr
                100                 105                 110

Ile Glu Tyr Ser Phe Tyr Leu Gly Asn His Glu Thr Asn Tyr Thr Leu
            115                 120                 125

His Leu Val Ala Ile Thr Gly Asn Val Pro Asn Ala Ile Pro Glu Asn
130                 135                 140

Lys Asp Leu Val Phe Ser Thr Trp Asp His Lys Ala Lys Gly His Phe
145                 150                 155                 160
```

Asn Cys Pro Glu Gly Tyr Ser Gly Gly Trp Trp His Asp Glu Cys
            165                 170                 175

Gly Glu Asn Asn Leu Asn Gly Lys Tyr Asn Lys Pro Arg Ala Gln Ser
            180                 185                 190

Lys Pro Glu Arg Arg Arg Gly Leu Ser Trp Lys Ser Gln Asn Gly Arg
            195                 200                 205

Leu Tyr Ser Ile Lys Ser Thr Lys Met Leu Ile His Pro Thr Asp Ser
            210                 215                 220

Glu Ser Phe Glu
225

<210> SEQ ID NO 14
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Glu Ile Arg Asn Val Lys His Asp Gly Ile Pro Ala Glu Cys Thr Thr
1               5                   10                  15

Ile Tyr Asn Arg Gly Glu His Thr Ser Gly Met Tyr Ala Ile Arg Pro
            20                  25                  30

Ser Asn Ser Gln Val Phe His Val Tyr Cys Asp Val Ile Ser Gly Ser
            35                  40                  45

Pro Trp Thr Leu Ile Gln His Arg Ile Asp Gly Ser Gln Asn Phe Asn
50                  55                  60

Glu Thr Trp Glu Asn Tyr Lys Tyr Gly Phe Gly Arg Leu Asp Gly Glu
65                  70                  75                  80

Phe Trp Leu Gly Leu Glu Lys Ile Tyr Ser Ile Val Lys Gln Ser Asn
                85                  90                  95

Tyr Val Leu Arg Ile Glu Leu Glu Asp Trp Lys Asp Asn Lys His Tyr
            100                 105                 110

Ile Glu Tyr Ser Phe Tyr Leu Gly Asn His Glu Thr Asn Tyr Thr Leu
            115                 120                 125

His Leu Val Ala Ile Thr Gly Asn Val Pro Asn Ala Ile Pro Glu Asn
        130                 135                 140

Lys Asp Leu Val Phe Ser Thr Trp Asp His Lys Ala Lys Gly His Phe
145                 150                 155                 160

Asn Cys Pro Glu Gly Tyr Ser Gly Gly Trp Trp His Asp Glu Cys
            165                 170                 175

Gly Glu Asn Asn Leu Asn Gly Lys Tyr Asn Lys Pro Arg Ala Ser Ser
            180                 185                 190

Lys Pro Glu Arg Arg Arg Gly Leu Ser Trp Lys Ser Gln Asn Gly Arg
            195                 200                 205

Leu Tyr Ser Ile Lys Ser Thr Lys Met Leu Ile His Pro Thr Asp Ser
            210                 215                 220

Glu Ser Phe Glu
225

<210> SEQ ID NO 15
<211> LENGTH: 220
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 15
```

Gly Ile Pro Ala Glu Cys Thr Thr Ile Tyr Asn Arg Gly Glu His Thr
1               5                   10                  15

Ser Gly Met Tyr Ala Ile Arg Pro Ser Asn Ser Gln Val Phe His Val
            20                  25                  30

Tyr Cys Asp Val Ile Ser Gly Ser Pro Trp Thr Leu Ile Gln His Arg
        35                  40                  45

Ile Asp Gly Ser Gln Asn Phe Asn Glu Thr Trp Glu Asn Tyr Lys Tyr
    50                  55                  60

Gly Phe Gly Arg Leu Asp Gly Glu Phe Trp Leu Gly Leu Glu Lys Ile
65                  70                  75                  80

Tyr Ser Ile Val Lys Gln Ser Asn Tyr Val Leu Arg Ile Glu Leu Glu
                85                  90                  95

Asp Trp Lys Asp Asn Lys His Tyr Ile Glu Tyr Ser Phe Tyr Leu Gly
            100                 105                 110

Asn His Glu Thr Asn Tyr Thr Leu His Leu Val Ala Ile Thr Gly Asn
        115                 120                 125

Val Pro Asn Ala Ile Pro Glu Asn Lys Asp Leu Val Phe Ser Thr Trp
    130                 135                 140

Asp His Lys Ala Lys Gly His Phe Asn Cys Pro Glu Gly Tyr Ser Gly
145                 150                 155                 160

Gly Trp Trp Trp His Asp Glu Cys Gly Glu Asn Asn Leu Asn Gly Lys
                165                 170                 175

Tyr Asn Lys Pro Arg Ala Gln Ser Lys Pro Glu Arg Arg Arg Gly Leu
            180                 185                 190

Ser Trp Lys Ser Gln Asn Gly Arg Leu Tyr Ser Ile Lys Ser Thr Lys
        195                 200                 205

Met Leu Ile His Pro Thr Asp Ser Glu Ser Phe Glu
    210                 215                 220

```
<210> SEQ ID NO 16
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16
```

Gly Ile Pro Ala Glu Cys Thr Thr Ile Tyr Asn Arg Gly Glu His Thr
1               5                   10                  15

Ser Gly Met Tyr Ala Ile Arg Pro Ser Asn Ser Gln Val Phe His Val
            20                  25                  30

Tyr Cys Asp Val Ile Ser Gly Ser Pro Trp Thr Leu Ile Gln His Arg
        35                  40                  45

Ile Asp Gly Ser Gln Asn Phe Asn Glu Thr Trp Glu Asn Tyr Lys Tyr
    50                  55                  60

Gly Phe Gly Arg Leu Asp Gly Glu Phe Trp Leu Gly Leu Glu Lys Ile
65                  70                  75                  80

Tyr Ser Ile Val Lys Gln Ser Asn Tyr Val Leu Arg Ile Glu Leu Glu
                85                  90                  95

Asp Trp Lys Asp Asn Lys His Tyr Ile Glu Tyr Ser Phe Tyr Leu Gly

```
                    100                 105                 110
Asn His Glu Thr Asn Tyr Thr Leu His Leu Val Ala Ile Thr Gly Asn
                115                 120                 125

Val Pro Asn Ala Ile Pro Glu Asn Lys Asp Leu Val Phe Ser Thr Trp
    130                 135                 140

Asp His Lys Ala Lys Gly His Phe Asn Cys Pro Glu Gly Tyr Ser Gly
145                 150                 155                 160

Gly Trp Trp Trp His Asp Glu Cys Gly Glu Asn Asn Leu Asn Gly Lys
                165                 170                 175

Tyr Asn Lys Pro Arg Ala Ser Ser Lys Pro Glu Arg Arg Arg Gly Leu
                180                 185                 190

Ser Trp Lys Ser Gln Asn Gly Arg Leu Tyr Ser Ile Lys Ser Thr Lys
            195                 200                 205

Met Leu Ile His Pro Thr Asp Ser Glu Ser Phe Glu
        210                 215                 220

<210> SEQ ID NO 17
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Ile Pro Ala Glu Cys Thr Thr Ile Tyr Asn Arg Gly Glu His Thr Ser
1               5                   10                  15

Gly Met Tyr Ala Ile Arg Pro Ser Asn Ser Gln Val Phe His Val Tyr
                20                  25                  30

Cys Asp Val Ile Ser Gly Ser Pro Trp Thr Leu Ile Gln His Arg Ile
            35                  40                  45

Asp Gly Ser Gln Asn Phe Asn Glu Thr Trp Glu Asn Tyr Lys Tyr Gly
        50                  55                  60

Phe Gly Arg Leu Asp Gly Glu Phe Trp Leu Gly Leu Glu Lys Ile Tyr
65                  70                  75                  80

Ser Ile Val Lys Gln Ser Asn Tyr Val Leu Arg Ile Glu Leu Glu Asp
                85                  90                  95

Trp Lys Asp Asn Lys His Tyr Ile Glu Tyr Ser Phe Tyr Leu Gly Asn
            100                 105                 110

His Glu Thr Asn Tyr Thr Leu His Leu Val Ala Ile Thr Gly Asn Val
        115                 120                 125

Pro Asn Ala Ile Pro Glu Asn Lys Asp Leu Val Phe Ser Thr Trp Asp
    130                 135                 140

His Lys Ala Lys Gly His Phe Asn Cys Pro Glu Gly Tyr Ser Gly Gly
145                 150                 155                 160

Trp Trp Trp His Asp Glu Cys Gly Glu Asn Asn Leu Asn Gly Lys Tyr
                165                 170                 175

Asn Lys Pro Arg Ala Gln Ser Lys Pro Glu Arg Arg Arg Gly Leu Ser
            180                 185                 190

Trp Lys Ser Gln Asn Gly Arg Leu Tyr Ser Ile Lys Ser Thr Lys Met
        195                 200                 205

Leu Ile His Pro Thr Asp Ser Glu Ser Phe Glu
    210                 215

<210> SEQ ID NO 18
```

<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 18

```
Ile Pro Ala Glu Cys Thr Thr Ile Tyr Asn Arg Gly Glu His Thr Ser
1               5                   10                  15

Gly Met Tyr Ala Ile Arg Pro Ser Asn Ser Gln Val Phe His Val Tyr
            20                  25                  30

Cys Asp Val Ile Ser Gly Ser Pro Trp Thr Leu Ile Gln His Arg Ile
        35                  40                  45

Asp Gly Ser Gln Asn Phe Asn Glu Thr Trp Glu Asn Tyr Lys Tyr Gly
    50                  55                  60

Phe Gly Arg Leu Asp Gly Glu Phe Trp Leu Gly Leu Glu Lys Ile Tyr
65                  70                  75                  80

Ser Ile Val Lys Gln Ser Asn Tyr Val Leu Arg Ile Glu Leu Glu Asp
                85                  90                  95

Trp Lys Asp Asn Lys His Tyr Ile Glu Tyr Ser Phe Tyr Leu Gly Asn
            100                 105                 110

His Glu Thr Asn Tyr Thr Leu His Leu Val Ala Ile Thr Gly Asn Val
        115                 120                 125

Pro Asn Ala Ile Pro Glu Asn Lys Asp Leu Val Phe Ser Thr Trp Asp
    130                 135                 140

His Lys Ala Lys Gly His Phe Asn Cys Pro Glu Gly Tyr Ser Gly Gly
145                 150                 155                 160

Trp Trp Trp His Asp Glu Cys Gly Glu Asn Asn Leu Asn Gly Lys Tyr
                165                 170                 175

Asn Lys Pro Arg Ala Ser Ser Lys Pro Glu Arg Arg Arg Gly Leu Ser
            180                 185                 190

Trp Lys Ser Gln Asn Gly Arg Leu Tyr Ser Ile Lys Ser Thr Lys Met
        195                 200                 205

Leu Ile His Pro Thr Asp Ser Glu Ser Phe Glu
    210                 215
```

<210> SEQ ID NO 19
<211> LENGTH: 231
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

```
Thr Thr Pro Phe Leu Gln Leu Asn Glu Ile Arg Asn Val Lys His Asp
1               5                   10                  15

Gly Ile Pro Ala Glu Cys Thr Thr Ile Tyr Asn Arg Gly Glu His Thr
            20                  25                  30

Ser Gly Met Tyr Ala Ile Arg Pro Ser Asn Ser Gln Val Phe His Val
        35                  40                  45

Tyr Cys Asp Val Ile Ser Gly Ser Pro Trp Thr Leu Ile Gln His Arg
    50                  55                  60

Ile Asp Gly Ser Gln Asn Phe Asn Glu Thr Trp Glu Asn Tyr Lys Tyr
65                  70                  75                  80
```

Gly Phe Gly Arg Leu Asp Gly Glu Phe Trp Leu Gly Leu Glu Lys Ile
            85                  90                  95

Tyr Ser Ile Val Lys Gln Ser Asn Tyr Val Leu Arg Ile Glu Leu Glu
            100                 105                 110

Asp Trp Lys Asp Asn Lys His Tyr Ile Glu Tyr Ser Phe Tyr Leu Gly
            115                 120                 125

Asn His Glu Thr Asn Tyr Thr Leu His Leu Val Ala Ile Thr Gly Asn
        130                 135                 140

Val Pro Asn Ala Ile Pro Glu Asn Lys Asp Leu Val Phe Ser Thr Trp
145                 150                 155                 160

Asp His Lys Ala Lys Gly His Phe Asn Cys Pro Glu Gly Tyr Ser Gly
            165                 170                 175

Gly Trp Trp Trp His Asp Glu Cys Gly Glu Asn Asn Leu Asn Gly Lys
            180                 185                 190

Tyr Asn Lys Pro Arg Ala Gln Ser Lys Pro Glu Arg Arg Arg Gly Leu
            195                 200                 205

Ser Trp Lys Ser Gln Asn Gly Arg Leu Tyr Ser Ile Lys Ser Thr Lys
            210                 215                 220

Met Leu Ile His Pro Thr Asp
225                 230

<210> SEQ ID NO 20
<211> LENGTH: 231
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Thr Thr Pro Phe Leu Gln Leu Asn Glu Ile Arg Asn Val Lys His Asp
1               5                   10                  15

Gly Ile Pro Ala Glu Cys Thr Thr Ile Tyr Asn Arg Gly Glu His Thr
            20                  25                  30

Ser Gly Met Tyr Ala Ile Arg Pro Ser Asn Ser Gln Val Phe His Val
        35                  40                  45

Tyr Cys Asp Val Ile Ser Gly Ser Pro Trp Thr Leu Ile Gln His Arg
50                  55                  60

Ile Asp Gly Ser Gln Asn Phe Asn Glu Thr Trp Glu Asn Tyr Lys Tyr
65                  70                  75                  80

Gly Phe Gly Arg Leu Asp Gly Glu Phe Trp Leu Gly Leu Glu Lys Ile
            85                  90                  95

Tyr Ser Ile Val Lys Gln Ser Asn Tyr Val Leu Arg Ile Glu Leu Glu
            100                 105                 110

Asp Trp Lys Asp Asn Lys His Tyr Ile Glu Tyr Ser Phe Tyr Leu Gly
            115                 120                 125

Asn His Glu Thr Asn Tyr Thr Leu His Leu Val Ala Ile Thr Gly Asn
        130                 135                 140

Val Pro Asn Ala Ile Pro Glu Asn Lys Asp Leu Val Phe Ser Thr Trp
145                 150                 155                 160

Asp His Lys Ala Lys Gly His Phe Asn Cys Pro Glu Gly Tyr Ser Gly
            165                 170                 175

Gly Trp Trp Trp His Asp Glu Cys Gly Glu Asn Asn Leu Asn Gly Lys
            180                 185                 190

Tyr Asn Lys Pro Arg Ala Ser Ser Lys Pro Glu Arg Arg Arg Gly Leu

```
                    195                 200                 205

Ser Trp Lys Ser Gln Asn Gly Arg Leu Tyr Ser Ile Lys Ser Thr Lys
    210                 215                 220

Met Leu Ile His Pro Thr Asp
225                 230

<210> SEQ ID NO 21
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Thr Pro Phe Leu Gln Leu Asn Glu Ile Arg Asn Val Lys His Asp Gly
1               5                   10                  15

Ile Pro Ala Glu Cys Thr Thr Ile Tyr Asn Arg Gly Glu His Thr Ser
                20                  25                  30

Gly Met Tyr Ala Ile Arg Pro Ser Asn Ser Gln Val Phe His Val Tyr
            35                  40                  45

Cys Asp Val Ile Ser Gly Ser Pro Trp Thr Leu Ile Gln His Arg Ile
    50                  55                  60

Asp Gly Ser Gln Asn Phe Asn Glu Thr Trp Glu Asn Tyr Lys Tyr Gly
65                  70                  75                  80

Phe Gly Arg Leu Asp Gly Glu Phe Trp Leu Gly Leu Glu Lys Ile Tyr
                85                  90                  95

Ser Ile Val Lys Gln Ser Asn Tyr Val Leu Arg Ile Glu Leu Glu Asp
            100                 105                 110

Trp Lys Asp Asn Lys His Tyr Ile Glu Tyr Ser Phe Tyr Leu Gly Asn
        115                 120                 125

His Glu Thr Asn Tyr Thr Leu His Leu Val Ala Ile Thr Gly Asn Val
    130                 135                 140

Pro Asn Ala Ile Pro Glu Asn Lys Asp Leu Val Phe Ser Thr Trp Asp
145                 150                 155                 160

His Lys Ala Lys Gly His Phe Asn Cys Pro Glu Gly Tyr Ser Gly Gly
                165                 170                 175

Trp Trp Trp His Asp Glu Cys Gly Glu Asn Asn Leu Asn Gly Lys Tyr
            180                 185                 190

Asn Lys Pro Arg Ala Gln Ser Lys Pro Glu Arg Arg Arg Gly Leu Ser
        195                 200                 205

Trp Lys Ser Gln Asn Gly Arg Leu Tyr Ser Ile Lys Ser Thr Lys Met
    210                 215                 220

Leu Ile His Pro Thr Asp
225                 230

<210> SEQ ID NO 22
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Thr Pro Phe Leu Gln Leu Asn Glu Ile Arg Asn Val Lys His Asp Gly
1               5                   10                  15
```

Ile Pro Ala Glu Cys Thr Thr Ile Tyr Asn Arg Gly Glu His Thr Ser
                20                  25                  30

Gly Met Tyr Ala Ile Arg Pro Ser Asn Ser Gln Val Phe His Val Tyr
            35                  40                  45

Cys Asp Val Ile Ser Gly Ser Pro Trp Thr Leu Ile Gln His Arg Ile
 50                  55                  60

Asp Gly Ser Gln Asn Phe Asn Glu Thr Trp Glu Asn Tyr Lys Tyr Gly
 65                  70                  75                  80

Phe Gly Arg Leu Asp Gly Glu Phe Trp Leu Gly Leu Glu Lys Ile Tyr
                85                  90                  95

Ser Ile Val Lys Gln Ser Asn Tyr Val Leu Arg Ile Glu Leu Glu Asp
                100                 105                 110

Trp Lys Asp Asn Lys His Tyr Ile Glu Tyr Ser Phe Tyr Leu Gly Asn
                115                 120                 125

His Glu Thr Asn Tyr Thr Leu His Leu Val Ala Ile Thr Gly Asn Val
130                 135                 140

Pro Asn Ala Ile Pro Glu Asn Lys Asp Leu Val Phe Ser Thr Trp Asp
145                 150                 155                 160

His Lys Ala Lys Gly His Phe Asn Cys Pro Glu Gly Tyr Ser Gly Gly
                165                 170                 175

Trp Trp Trp His Asp Glu Cys Gly Glu Asn Asn Leu Asn Gly Lys Tyr
                180                 185                 190

Asn Lys Pro Arg Ala Ser Ser Lys Pro Glu Arg Arg Arg Gly Leu Ser
                195                 200                 205

Trp Lys Ser Gln Asn Gly Arg Leu Tyr Ser Ile Lys Ser Thr Lys Met
210                 215                 220

Leu Ile His Pro Thr Asp
225                 230

<210> SEQ ID NO 23
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Phe Leu Gln Leu Asn Glu Ile Arg Asn Val Lys His Asp Gly Ile Pro
 1               5                   10                  15

Ala Glu Cys Thr Thr Ile Tyr Asn Arg Gly Glu His Thr Ser Gly Met
                20                  25                  30

Tyr Ala Ile Arg Pro Ser Asn Ser Gln Val Phe His Val Tyr Cys Asp
            35                  40                  45

Val Ile Ser Gly Ser Pro Trp Thr Leu Ile Gln His Arg Ile Asp Gly
 50                  55                  60

Ser Gln Asn Phe Asn Glu Thr Trp Glu Asn Tyr Lys Tyr Gly Phe Gly
 65                  70                  75                  80

Arg Leu Asp Gly Glu Phe Trp Leu Gly Leu Glu Lys Ile Tyr Ser Ile
                85                  90                  95

Val Lys Gln Ser Asn Tyr Val Leu Arg Ile Glu Leu Glu Asp Trp Lys
                100                 105                 110

Asp Asn Lys His Tyr Ile Glu Tyr Ser Phe Tyr Leu Gly Asn His Glu
                115                 120                 125

```
Thr Asn Tyr Thr Leu His Leu Val Ala Ile Thr Gly Asn Val Pro Asn
    130                 135                 140

Ala Ile Pro Glu Asn Lys Asp Leu Val Phe Ser Thr Trp Asp His Lys
145                 150                 155                 160

Ala Lys Gly His Phe Asn Cys Pro Glu Gly Tyr Ser Gly Gly Trp Trp
                165                 170                 175

Trp His Asp Glu Cys Gly Glu Asn Asn Leu Asn Gly Lys Tyr Asn Lys
                180                 185                 190

Pro Arg Ala Gln Ser Lys Pro Glu Arg Arg Gly Leu Ser Trp Lys
                195                 200                 205

Ser Gln Asn Gly Arg Leu Tyr Ser Ile Lys Ser Thr Lys Met Leu Ile
    210                 215                 220

His Pro Thr Asp
225

<210> SEQ ID NO 24
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Phe Leu Gln Leu Asn Glu Ile Arg Asn Val Lys His Asp Gly Ile Pro
1               5                   10                  15

Ala Glu Cys Thr Thr Ile Tyr Asn Arg Gly Glu His Thr Ser Gly Met
                20                  25                  30

Tyr Ala Ile Arg Pro Ser Asn Ser Gln Val Phe His Val Tyr Cys Asp
            35                  40                  45

Val Ile Ser Gly Ser Pro Trp Thr Leu Ile Gln His Arg Ile Asp Gly
    50                  55                  60

Ser Gln Asn Phe Asn Glu Thr Trp Glu Asn Tyr Lys Tyr Gly Phe Gly
65                  70                  75                  80

Arg Leu Asp Gly Glu Phe Trp Leu Gly Leu Glu Lys Ile Tyr Ser Ile
                85                  90                  95

Val Lys Gln Ser Asn Tyr Val Leu Arg Ile Glu Leu Glu Asp Trp Lys
                100                 105                 110

Asp Asn Lys His Tyr Ile Glu Tyr Ser Phe Tyr Leu Gly Asn His Glu
            115                 120                 125

Thr Asn Tyr Thr Leu His Leu Val Ala Ile Thr Gly Asn Val Pro Asn
    130                 135                 140

Ala Ile Pro Glu Asn Lys Asp Leu Val Phe Ser Thr Trp Asp His Lys
145                 150                 155                 160

Ala Lys Gly His Phe Asn Cys Pro Glu Gly Tyr Ser Gly Gly Trp Trp
                165                 170                 175

Trp His Asp Glu Cys Gly Glu Asn Asn Leu Asn Gly Lys Tyr Asn Lys
                180                 185                 190

Pro Arg Ala Ser Ser Lys Pro Glu Arg Arg Gly Leu Ser Trp Lys
                195                 200                 205

Ser Gln Asn Gly Arg Leu Tyr Ser Ile Lys Ser Thr Lys Met Leu Ile
    210                 215                 220

His Pro Thr Asp
225
```

```
<210> SEQ ID NO 25
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Glu Ile Arg Asn Val Lys His Asp Gly Ile Pro Ala Glu Cys Thr Thr
1               5                   10                  15

Ile Tyr Asn Arg Gly Glu His Thr Ser Gly Met Tyr Ala Ile Arg Pro
            20                  25                  30

Ser Asn Ser Gln Val Phe His Val Tyr Cys Asp Val Ile Ser Gly Ser
        35                  40                  45

Pro Trp Thr Leu Ile Gln His Arg Ile Asp Gly Ser Gln Asn Phe Asn
    50                  55                  60

Glu Thr Trp Glu Asn Tyr Lys Tyr Gly Phe Gly Arg Leu Asp Gly Glu
65                  70                  75                  80

Phe Trp Leu Gly Leu Glu Lys Ile Tyr Ser Ile Val Lys Gln Ser Asn
                85                  90                  95

Tyr Val Leu Arg Ile Glu Leu Glu Asp Trp Lys Asp Asn Lys His Tyr
            100                 105                 110

Ile Glu Tyr Ser Phe Tyr Leu Gly Asn His Glu Thr Asn Tyr Thr Leu
        115                 120                 125

His Leu Val Ala Ile Thr Gly Asn Val Pro Asn Ala Ile Pro Glu Asn
    130                 135                 140

Lys Asp Leu Val Phe Ser Thr Trp Asp His Lys Ala Lys Gly His Phe
145                 150                 155                 160

Asn Cys Pro Glu Gly Tyr Ser Gly Gly Trp Trp His Asp Glu Cys
                165                 170                 175

Gly Glu Asn Asn Leu Asn Gly Lys Tyr Asn Lys Pro Arg Ala Gln Ser
            180                 185                 190

Lys Pro Glu Arg Arg Arg Gly Leu Ser Trp Lys Ser Gln Asn Gly Arg
        195                 200                 205

Leu Tyr Ser Ile Lys Ser Thr Lys Met Leu Ile His Pro Thr Asp
    210                 215                 220

<210> SEQ ID NO 26
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Glu Ile Arg Asn Val Lys His Asp Gly Ile Pro Ala Glu Cys Thr Thr
1               5                   10                  15

Ile Tyr Asn Arg Gly Glu His Thr Ser Gly Met Tyr Ala Ile Arg Pro
            20                  25                  30

Ser Asn Ser Gln Val Phe His Val Tyr Cys Asp Val Ile Ser Gly Ser
        35                  40                  45

Pro Trp Thr Leu Ile Gln His Arg Ile Asp Gly Ser Gln Asn Phe Asn
    50                  55                  60

Glu Thr Trp Glu Asn Tyr Lys Tyr Gly Phe Gly Arg Leu Asp Gly Glu
65                  70                  75                  80
```

Phe Trp Leu Gly Leu Glu Lys Ile Tyr Ser Ile Val Lys Gln Ser Asn
                85                  90                  95

Tyr Val Leu Arg Ile Glu Leu Glu Asp Trp Lys Asp Asn Lys His Tyr
            100                 105                 110

Ile Glu Tyr Ser Phe Tyr Leu Gly Asn His Glu Thr Asn Tyr Thr Leu
            115                 120                 125

His Leu Val Ala Ile Thr Gly Asn Val Pro Asn Ala Ile Pro Glu Asn
130                 135                 140

Lys Asp Leu Val Phe Ser Thr Trp Asp His Lys Ala Lys Gly His Phe
145                 150                 155                 160

Asn Cys Pro Glu Gly Tyr Ser Gly Gly Trp Trp Trp His Asp Glu Cys
            165                 170                 175

Gly Glu Asn Asn Leu Asn Gly Lys Tyr Asn Lys Pro Arg Ala Ser Ser
            180                 185                 190

Lys Pro Glu Arg Arg Arg Gly Leu Ser Trp Lys Ser Gln Asn Gly Arg
            195                 200                 205

Leu Tyr Ser Ile Lys Ser Thr Lys Met Leu Ile His Pro Thr Asp
            210                 215                 220

<210> SEQ ID NO 27
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gly Ile Pro Ala Glu Cys Thr Thr Ile Tyr Asn Arg Gly Glu His Thr
1               5                   10                  15

Ser Gly Met Tyr Ala Ile Arg Pro Ser Asn Ser Gln Val Phe His Val
            20                  25                  30

Tyr Cys Asp Val Ile Ser Gly Ser Pro Trp Thr Leu Ile Gln His Arg
            35                  40                  45

Ile Asp Gly Ser Gln Asn Phe Asn Glu Thr Trp Glu Asn Tyr Lys Tyr
        50                  55                  60

Gly Phe Gly Arg Leu Asp Gly Glu Phe Trp Leu Gly Leu Glu Lys Ile
65                  70                  75                  80

Tyr Ser Ile Val Lys Gln Ser Asn Tyr Val Leu Arg Ile Glu Leu Glu
                85                  90                  95

Asp Trp Lys Asp Asn Lys His Tyr Ile Glu Tyr Ser Phe Tyr Leu Gly
            100                 105                 110

Asn His Glu Thr Asn Tyr Thr Leu His Leu Val Ala Ile Thr Gly Asn
            115                 120                 125

Val Pro Asn Ala Ile Pro Glu Asn Lys Asp Leu Val Phe Ser Thr Trp
130                 135                 140

Asp His Lys Ala Lys Gly His Phe Asn Cys Pro Glu Gly Tyr Ser Gly
145                 150                 155                 160

Gly Trp Trp Trp His Asp Glu Cys Gly Glu Asn Asn Leu Asn Gly Lys
            165                 170                 175

Tyr Asn Lys Pro Arg Ala Gln Ser Lys Pro Glu Arg Arg Arg Gly Leu
            180                 185                 190

Ser Trp Lys Ser Gln Asn Gly Arg Leu Tyr Ser Ile Lys Ser Thr Lys
            195                 200                 205

```
Met Leu Ile His Pro Thr Asp
    210                 215
```

<210> SEQ ID NO 28
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

```
Gly Ile Pro Ala Glu Cys Thr Thr Ile Tyr Asn Arg Gly Glu His Thr
1               5                   10                  15

Ser Gly Met Tyr Ala Ile Arg Pro Ser Asn Ser Gln Val Phe His Val
            20                  25                  30

Tyr Cys Asp Val Ile Ser Gly Ser Pro Trp Thr Leu Ile Gln His Arg
        35                  40                  45

Ile Asp Gly Ser Gln Asn Phe Asn Glu Thr Trp Glu Asn Tyr Lys Tyr
    50                  55                  60

Gly Phe Gly Arg Leu Asp Gly Glu Phe Trp Leu Gly Leu Glu Lys Ile
65                  70                  75                  80

Tyr Ser Ile Val Lys Gln Ser Asn Tyr Val Leu Arg Ile Glu Leu Glu
                85                  90                  95

Asp Trp Lys Asp Asn Lys His Tyr Ile Glu Tyr Ser Phe Tyr Leu Gly
            100                 105                 110

Asn His Glu Thr Asn Tyr Thr Leu His Leu Val Ala Ile Thr Gly Asn
        115                 120                 125

Val Pro Asn Ala Ile Pro Glu Asn Lys Asp Leu Val Phe Ser Thr Trp
    130                 135                 140

Asp His Lys Ala Lys Gly His Phe Asn Cys Pro Glu Gly Tyr Ser Gly
145                 150                 155                 160

Gly Trp Trp Trp His Asp Glu Cys Gly Glu Asn Asn Leu Asn Gly Lys
                165                 170                 175

Tyr Asn Lys Pro Arg Ala Ser Ser Lys Pro Glu Arg Arg Arg Gly Leu
            180                 185                 190

Ser Trp Lys Ser Gln Asn Gly Arg Leu Tyr Ser Ile Lys Ser Thr Lys
        195                 200                 205

Met Leu Ile His Pro Thr Asp
    210                 215
```

<210> SEQ ID NO 29
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

```
Ile Pro Ala Glu Cys Thr Thr Ile Tyr Asn Arg Gly Glu His Thr Ser
1               5                   10                  15

Gly Met Tyr Ala Ile Arg Pro Ser Asn Ser Gln Val Phe His Val Tyr
            20                  25                  30

Cys Asp Val Ile Ser Gly Ser Pro Trp Thr Leu Ile Gln His Arg Ile
        35                  40                  45

Asp Gly Ser Gln Asn Phe Asn Glu Thr Trp Glu Asn Tyr Lys Tyr Gly
```

```
            50                  55                  60
Phe Gly Arg Leu Asp Gly Glu Phe Trp Leu Gly Leu Glu Lys Ile Tyr
 65                  70                  75                  80

Ser Ile Val Lys Gln Ser Asn Tyr Val Leu Arg Ile Glu Leu Glu Asp
                 85                  90                  95

Trp Lys Asp Asn Lys His Tyr Ile Glu Tyr Ser Phe Tyr Leu Gly Asn
                100                 105                 110

His Glu Thr Asn Tyr Thr Leu His Leu Val Ala Ile Thr Gly Asn Val
            115                 120                 125

Pro Asn Ala Ile Pro Glu Asn Lys Asp Leu Val Phe Ser Thr Trp Asp
        130                 135                 140

His Lys Ala Lys Gly His Phe Asn Cys Pro Glu Gly Tyr Ser Gly Gly
145                 150                 155                 160

Trp Trp Trp His Asp Glu Cys Gly Glu Asn Asn Leu Asn Gly Lys Tyr
                165                 170                 175

Asn Lys Pro Arg Ala Gln Ser Lys Pro Glu Arg Arg Arg Gly Leu Ser
                180                 185                 190

Trp Lys Ser Gln Asn Gly Arg Leu Tyr Ser Ile Lys Ser Thr Lys Met
            195                 200                 205

Leu Ile His Pro Thr Asp
        210

<210> SEQ ID NO 30
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Ile Pro Ala Glu Cys Thr Thr Ile Tyr Asn Arg Gly Glu His Thr Ser
 1               5                  10                  15

Gly Met Tyr Ala Ile Arg Pro Ser Asn Ser Gln Val Phe His Val Tyr
                20                  25                  30

Cys Asp Val Ile Ser Gly Ser Pro Trp Thr Leu Ile Gln His Arg Ile
            35                  40                  45

Asp Gly Ser Gln Asn Phe Asn Glu Thr Trp Glu Asn Tyr Lys Tyr Gly
        50                  55                  60

Phe Gly Arg Leu Asp Gly Glu Phe Trp Leu Gly Leu Glu Lys Ile Tyr
 65                  70                  75                  80

Ser Ile Val Lys Gln Ser Asn Tyr Val Leu Arg Ile Glu Leu Glu Asp
                 85                  90                  95

Trp Lys Asp Asn Lys His Tyr Ile Glu Tyr Ser Phe Tyr Leu Gly Asn
                100                 105                 110

His Glu Thr Asn Tyr Thr Leu His Leu Val Ala Ile Thr Gly Asn Val
            115                 120                 125

Pro Asn Ala Ile Pro Glu Asn Lys Asp Leu Val Phe Ser Thr Trp Asp
        130                 135                 140

His Lys Ala Lys Gly His Phe Asn Cys Pro Glu Gly Tyr Ser Gly Gly
145                 150                 155                 160

Trp Trp Trp His Asp Glu Cys Gly Glu Asn Asn Leu Asn Gly Lys Tyr
                165                 170                 175

Asn Lys Pro Arg Ala Ser Ser Lys Pro Glu Arg Arg Arg Gly Leu Ser
                180                 185                 190
```

```
Trp Lys Ser Gln Asn Gly Arg Leu Tyr Ser Ile Lys Ser Thr Lys Met
        195                 200                 205

Leu Ile His Pro Thr Asp
    210
```

<210> SEQ ID NO 31
<211> LENGTH: 252
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 31

```
Ile Gln Glu Pro Thr Glu Ile Ser Leu Ser Ser Lys Pro Arg Ala Pro
1               5                   10                  15

Arg Thr Thr Pro Phe Leu Gln Leu Asn Glu Ile Arg Asn Val Lys His
            20                  25                  30

Asp Gly Ile Pro Ala Glu Cys Thr Thr Ile Tyr Asn Arg Gly Glu His
        35                  40                  45

Thr Ser Gly Met Tyr Ala Ile Arg Pro Ser Asn Ser Gln Val Phe His
    50                  55                  60

Val Tyr Cys Asp Val Ile Ser Gly Ser Pro Trp Thr Leu Ile Gln His
65                  70                  75                  80

Arg Ile Asp Gly Ser Gln Asn Phe Asn Glu Thr Trp Glu Asn Tyr Lys
                85                  90                  95

Tyr Gly Phe Gly Arg Leu Asp Gly Glu Phe Trp Leu Gly Leu Glu Lys
            100                 105                 110

Ile Tyr Ser Ile Val Lys Gln Ser Asn Tyr Val Leu Arg Ile Glu Leu
        115                 120                 125

Glu Asp Trp Lys Asp Asn Lys His Tyr Ile Glu Tyr Ser Phe Tyr Leu
    130                 135                 140

Gly Asn His Glu Thr Asn Tyr Thr Leu His Leu Val Ala Ile Thr Gly
145                 150                 155                 160

Asn Val Pro Asn Ala Ile Pro Glu Asn Lys Asp Leu Val Phe Ser Thr
                165                 170                 175

Trp Asp His Lys Ala Lys Gly His Phe Asn Cys Pro Glu Gly Tyr Ser
            180                 185                 190

Gly Gly Trp Trp Trp His Asp Glu Cys Gly Glu Asn Asn Leu Asn Gly
        195                 200                 205

Lys Tyr Asn Lys Pro Arg Ala Ser Lys Pro Glu Arg Arg Arg Gly Leu
    210                 215                 220

Ser Trp Lys Ser Gln Asn Gly Arg Leu Tyr Ser Ile Lys Ser Thr Lys
225                 230                 235                 240

Met Leu Ile His Pro Thr Asp Ser Glu Ser Phe Glu
                245                 250
```

<210> SEQ ID NO 32
<211> LENGTH: 235
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 32

Thr Thr Pro Phe Leu Gln Leu Asn Glu Ile Arg Asn Val Lys His Asp
1               5                   10                  15

Gly Ile Pro Ala Glu Cys Thr Thr Ile Tyr Asn Arg Gly Glu His Thr
                20                  25                  30

Ser Gly Met Tyr Ala Ile Arg Pro Ser Asn Ser Gln Val Phe His Val
            35                  40                  45

Tyr Cys Asp Val Ile Ser Gly Ser Pro Trp Thr Leu Ile Gln His Arg
    50                  55                  60

Ile Asp Gly Ser Gln Asn Phe Asn Glu Thr Trp Glu Asn Tyr Lys Tyr
65                  70                  75                  80

Gly Phe Gly Arg Leu Asp Gly Glu Phe Trp Leu Gly Leu Glu Lys Ile
                85                  90                  95

Tyr Ser Ile Val Lys Gln Ser Asn Tyr Val Leu Arg Ile Glu Leu Glu
            100                 105                 110

Asp Trp Lys Asp Asn Lys His Tyr Ile Glu Tyr Ser Phe Tyr Leu Gly
            115                 120                 125

Asn His Glu Thr Asn Tyr Thr Leu His Leu Val Ala Ile Thr Gly Asn
            130                 135                 140

Val Pro Asn Ala Ile Pro Glu Asn Lys Asp Leu Val Phe Ser Thr Trp
145                 150                 155                 160

Asp His Lys Ala Lys Gly His Phe Asn Cys Pro Glu Gly Tyr Ser Gly
                165                 170                 175

Gly Trp Trp Trp His Asp Glu Cys Gly Glu Asn Asn Leu Asn Gly Lys
                180                 185                 190

Tyr Asn Lys Pro Arg Ala Ser Lys Pro Glu Arg Arg Arg Gly Leu Ser
            195                 200                 205

Trp Lys Ser Gln Asn Gly Arg Leu Tyr Ser Ile Lys Ser Thr Lys Met
210                 215                 220

Leu Ile His Pro Thr Asp Ser Glu Ser Phe Glu
225                 230                 235

<210> SEQ ID NO 33
<211> LENGTH: 234
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Thr Pro Phe Leu Gln Leu Asn Glu Ile Arg Asn Val Lys His Asp Gly
1               5                   10                  15

Ile Pro Ala Glu Cys Thr Thr Ile Tyr Asn Arg Gly Glu His Thr Ser
                20                  25                  30

Gly Met Tyr Ala Ile Arg Pro Ser Asn Ser Gln Val Phe His Val Tyr
            35                  40                  45

Cys Asp Val Ile Ser Gly Ser Pro Trp Thr Leu Ile Gln His Arg Ile
    50                  55                  60

Asp Gly Ser Gln Asn Phe Asn Glu Thr Trp Glu Asn Tyr Lys Tyr Gly
65                  70                  75                  80

Phe Gly Arg Leu Asp Gly Glu Phe Trp Leu Gly Leu Glu Lys Ile Tyr
                85                  90                  95

Ser Ile Val Lys Gln Ser Asn Tyr Val Leu Arg Ile Glu Leu Glu Asp
            100                 105                 110

Trp Lys Asp Asn Lys His Tyr Ile Glu Tyr Ser Phe Tyr Leu Gly Asn

```
                    115                 120                 125
His Glu Thr Asn Tyr Thr Leu His Leu Val Ala Ile Thr Gly Asn Val
    130                 135                 140
Pro Asn Ala Ile Pro Glu Asn Lys Asp Leu Val Phe Ser Thr Trp Asp
145                 150                 155                 160
His Lys Ala Lys Gly His Phe Asn Cys Pro Glu Gly Tyr Ser Gly Gly
                165                 170                 175
Trp Trp Trp His Asp Glu Cys Gly Glu Asn Asn Leu Asn Gly Lys Tyr
            180                 185                 190
Asn Lys Pro Arg Ala Ser Lys Pro Glu Arg Arg Gly Leu Ser Trp
        195                 200                 205
Lys Ser Gln Asn Gly Arg Leu Tyr Ser Ile Lys Ser Thr Lys Met Leu
    210                 215                 220
Ile His Pro Thr Asp Ser Glu Ser Phe Glu
225                 230

<210> SEQ ID NO 34
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Phe Leu Gln Leu Asn Glu Ile Arg Asn Val Lys His Asp Gly Ile Pro
1               5                   10                  15
Ala Glu Cys Thr Thr Ile Tyr Asn Arg Gly Glu His Thr Ser Gly Met
            20                  25                  30
Tyr Ala Ile Arg Pro Ser Asn Ser Gln Val Phe His Val Tyr Cys Asp
        35                  40                  45
Val Ile Ser Gly Ser Pro Trp Thr Leu Ile Gln His Arg Ile Asp Gly
    50                  55                  60
Ser Gln Asn Phe Asn Glu Thr Trp Glu Asn Tyr Lys Tyr Gly Phe Gly
65                  70                  75                  80
Arg Leu Asp Gly Glu Phe Trp Leu Gly Leu Glu Lys Ile Tyr Ser Ile
                85                  90                  95
Val Lys Gln Ser Asn Tyr Val Leu Arg Ile Glu Leu Glu Asp Trp Lys
            100                 105                 110
Asp Asn Lys His Tyr Ile Glu Tyr Ser Phe Tyr Leu Gly Asn His Glu
        115                 120                 125
Thr Asn Tyr Thr Leu His Leu Val Ala Ile Thr Gly Asn Val Pro Asn
    130                 135                 140
Ala Ile Pro Glu Asn Lys Asp Leu Val Phe Ser Thr Trp Asp His Lys
145                 150                 155                 160
Ala Lys Gly His Phe Asn Cys Pro Glu Gly Tyr Ser Gly Gly Trp Trp
                165                 170                 175
Trp His Asp Glu Cys Gly Glu Asn Asn Leu Asn Gly Lys Tyr Asn Lys
            180                 185                 190
Pro Arg Ala Ser Lys Pro Glu Arg Arg Gly Leu Ser Trp Lys Ser
        195                 200                 205
Gln Asn Gly Arg Leu Tyr Ser Ile Lys Ser Thr Lys Met Leu Ile His
    210                 215                 220
Pro Thr Asp Ser Glu Ser Phe Glu
225                 230
```

<210> SEQ ID NO 35
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 35

Glu Ile Arg Asn Val Lys His Asp Gly Ile Pro Ala Glu Cys Thr Thr
1               5                   10                  15

Ile Tyr Asn Arg Gly Glu His Thr Ser Gly Met Tyr Ala Ile Arg Pro
            20                  25                  30

Ser Asn Ser Gln Val Phe His Val Tyr Cys Asp Val Ile Ser Gly Ser
        35                  40                  45

Pro Trp Thr Leu Ile Gln His Arg Ile Asp Gly Ser Gln Asn Phe Asn
    50                  55                  60

Glu Thr Trp Glu Asn Tyr Lys Tyr Gly Phe Gly Arg Leu Asp Gly Glu
65                  70                  75                  80

Phe Trp Leu Gly Leu Glu Lys Ile Tyr Ser Ile Val Lys Gln Ser Asn
                85                  90                  95

Tyr Val Leu Arg Ile Glu Leu Glu Asp Trp Lys Asp Asn Lys His Tyr
            100                 105                 110

Ile Glu Tyr Ser Phe Tyr Leu Gly Asn His Glu Thr Asn Tyr Thr Leu
        115                 120                 125

His Leu Val Ala Ile Thr Gly Asn Val Pro Asn Ala Ile Pro Glu Asn
    130                 135                 140

Lys Asp Leu Val Phe Ser Thr Trp Asp His Lys Ala Lys Gly His Phe
145                 150                 155                 160

Asn Cys Pro Glu Gly Tyr Ser Gly Gly Trp Trp Trp His Asp Glu Cys
                165                 170                 175

Gly Glu Asn Asn Leu Asn Gly Lys Tyr Asn Lys Pro Arg Ala Ser Lys
            180                 185                 190

Pro Glu Arg Arg Arg Gly Leu Ser Trp Lys Ser Gln Asn Gly Arg Leu
        195                 200                 205

Tyr Ser Ile Lys Ser Thr Lys Met Leu Ile His Pro Thr Asp Ser Glu
    210                 215                 220

Ser Phe Glu
225

<210> SEQ ID NO 36
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 36

Gly Ile Pro Ala Glu Cys Thr Thr Ile Tyr Asn Arg Gly Glu His Thr
1               5                   10                  15

Ser Gly Met Tyr Ala Ile Arg Pro Ser Asn Ser Gln Val Phe His Val
            20                  25                  30

Tyr Cys Asp Val Ile Ser Gly Ser Pro Trp Thr Leu Ile Gln His Arg
        35                  40                  45

Ile Asp Gly Ser Gln Asn Phe Asn Glu Thr Trp Glu Asn Tyr Lys Tyr
    50                  55                  60

Gly Phe Gly Arg Leu Asp Gly Glu Phe Trp Leu Gly Leu Glu Lys Ile
65                  70                  75                  80

Tyr Ser Ile Val Lys Gln Ser Asn Tyr Val Leu Arg Ile Glu Leu Glu
                85                  90                  95

Asp Trp Lys Asp Asn Lys His Tyr Ile Glu Tyr Ser Phe Tyr Leu Gly
                100                 105                 110

Asn His Glu Thr Asn Tyr Thr Leu His Leu Val Ala Ile Thr Gly Asn
                115                 120                 125

Val Pro Asn Ala Ile Pro Glu Asn Lys Asp Leu Val Phe Ser Thr Trp
130                 135                 140

Asp His Lys Ala Lys Gly His Phe Asn Cys Pro Glu Gly Tyr Ser Gly
145                 150                 155                 160

Gly Trp Trp Trp His Asp Glu Cys Gly Glu Asn Asn Leu Asn Gly Lys
                165                 170                 175

Tyr Asn Lys Pro Arg Ala Ser Lys Pro Glu Arg Arg Arg Gly Leu Ser
                180                 185                 190

Trp Lys Ser Gln Asn Gly Arg Leu Tyr Ser Ile Lys Ser Thr Lys Met
                195                 200                 205

Leu Ile His Pro Thr Asp Ser Glu Ser Phe Glu
210                 215

<210> SEQ ID NO 37
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Ile Pro Ala Glu Cys Thr Thr Ile Tyr Asn Arg Gly Glu His Thr Ser
1               5                   10                  15

Gly Met Tyr Ala Ile Arg Pro Ser Asn Ser Gln Val Phe His Val Tyr
                20                  25                  30

Cys Asp Val Ile Ser Gly Ser Pro Trp Thr Leu Ile Gln His Arg Ile
                35                  40                  45

Asp Gly Ser Gln Asn Phe Asn Glu Thr Trp Glu Asn Tyr Lys Tyr Gly
    50                  55                  60

Phe Gly Arg Leu Asp Gly Glu Phe Trp Leu Gly Leu Glu Lys Ile Tyr
65                  70                  75                  80

Ser Ile Val Lys Gln Ser Asn Tyr Val Leu Arg Ile Glu Leu Glu Asp
                85                  90                  95

Trp Lys Asp Asn Lys His Tyr Ile Glu Tyr Ser Phe Tyr Leu Gly Asn
                100                 105                 110

His Glu Thr Asn Tyr Thr Leu His Leu Val Ala Ile Thr Gly Asn Val
                115                 120                 125

Pro Asn Ala Ile Pro Glu Asn Lys Asp Leu Val Phe Ser Thr Trp Asp
130                 135                 140

His Lys Ala Lys Gly His Phe Asn Cys Pro Glu Gly Tyr Ser Gly Gly
145                 150                 155                 160

Trp Trp Trp His Asp Glu Cys Gly Glu Asn Asn Leu Asn Gly Lys Tyr
                165                 170                 175

Asn Lys Pro Arg Ala Ser Lys Pro Glu Arg Arg Arg Gly Leu Ser Trp

```
                180                 185                 190
Lys Ser Gln Asn Gly Arg Leu Tyr Ser Ile Lys Ser Thr Lys Met Leu
        195                 200                 205
Ile His Pro Thr Asp Ser Glu Ser Phe Glu
        210                 215

<210> SEQ ID NO 38
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Thr Thr Pro Phe Leu Gln Leu Asn Glu Ile Arg Asn Val Lys His Asp
1               5                   10                  15

Gly Ile Pro Ala Glu Cys Thr Thr Ile Tyr Asn Arg Gly Glu His Thr
            20                  25                  30

Ser Gly Met Tyr Ala Ile Arg Pro Ser Asn Ser Gln Val Phe His Val
        35                  40                  45

Tyr Cys Asp Val Ile Ser Gly Ser Pro Trp Thr Leu Ile Gln His Arg
    50                  55                  60

Ile Asp Gly Ser Gln Asn Phe Asn Glu Thr Trp Glu Asn Tyr Lys Tyr
65                  70                  75                  80

Gly Phe Gly Arg Leu Asp Gly Glu Phe Trp Leu Gly Leu Glu Lys Ile
                85                  90                  95

Tyr Ser Ile Val Lys Gln Ser Asn Tyr Val Leu Arg Ile Glu Leu Glu
            100                 105                 110

Asp Trp Lys Asp Asn Lys His Tyr Ile Glu Tyr Ser Phe Tyr Leu Gly
        115                 120                 125

Asn His Glu Thr Asn Tyr Thr Leu His Leu Val Ala Ile Thr Gly Asn
    130                 135                 140

Val Pro Asn Ala Ile Pro Glu Asn Lys Asp Leu Val Phe Ser Thr Trp
145                 150                 155                 160

Asp His Lys Ala Lys Gly His Phe Asn Cys Pro Glu Gly Tyr Ser Gly
                165                 170                 175

Gly Trp Trp Trp His Asp Glu Cys Gly Glu Asn Asn Leu Asn Gly Lys
            180                 185                 190

Tyr Asn Lys Pro Arg Ala Ser Lys Pro Glu Arg Arg Arg Gly Leu Ser
        195                 200                 205

Trp Lys Ser Gln Asn Gly Arg Leu Tyr Ser Ile Lys Ser Thr Lys Met
    210                 215                 220

Leu Ile His Pro Thr Asp
225                 230

<210> SEQ ID NO 39
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Thr Pro Phe Leu Gln Leu Asn Glu Ile Arg Asn Val Lys His Asp Gly
1               5                   10                  15
```

Ile Pro Ala Glu Cys Thr Thr Ile Tyr Asn Arg Gly Glu His Thr Ser
            20                  25                  30

Gly Met Tyr Ala Ile Arg Pro Ser Asn Ser Gln Val Phe His Val Tyr
        35                  40                  45

Cys Asp Val Ile Ser Gly Ser Pro Trp Thr Leu Ile Gln His Arg Ile
50                  55                  60

Asp Gly Ser Gln Asn Phe Asn Glu Thr Trp Glu Asn Tyr Lys Tyr Gly
65                  70                  75                  80

Phe Gly Arg Leu Asp Gly Glu Phe Trp Leu Gly Leu Glu Lys Ile Tyr
                85                  90                  95

Ser Ile Val Lys Gln Ser Asn Tyr Val Leu Arg Ile Glu Leu Glu Asp
            100                 105                 110

Trp Lys Asp Asn Lys His Tyr Ile Glu Tyr Ser Phe Tyr Leu Gly Asn
        115                 120                 125

His Glu Thr Asn Tyr Thr Leu His Leu Val Ala Ile Thr Gly Asn Val
130                 135                 140

Pro Asn Ala Ile Pro Glu Asn Lys Asp Leu Val Phe Ser Thr Trp Asp
145                 150                 155                 160

His Lys Ala Lys Gly His Phe Asn Cys Pro Glu Gly Tyr Ser Gly Gly
                165                 170                 175

Trp Trp Trp His Asp Glu Cys Gly Glu Asn Asn Leu Asn Gly Lys Tyr
            180                 185                 190

Asn Lys Pro Arg Ala Ser Lys Pro Glu Arg Arg Arg Gly Leu Ser Trp
        195                 200                 205

Lys Ser Gln Asn Gly Arg Leu Tyr Ser Ile Lys Ser Thr Lys Met Leu
210                 215                 220

Ile His Pro Thr Asp
225

<210> SEQ ID NO 40
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Phe Leu Gln Leu Asn Glu Ile Arg Asn Val Lys His Asp Gly Ile Pro
1               5                   10                  15

Ala Glu Cys Thr Thr Ile Tyr Asn Arg Gly Glu His Thr Ser Gly Met
            20                  25                  30

Tyr Ala Ile Arg Pro Ser Asn Ser Gln Val Phe His Val Tyr Cys Asp
        35                  40                  45

Val Ile Ser Gly Ser Pro Trp Thr Leu Ile Gln His Arg Ile Asp Gly
50                  55                  60

Ser Gln Asn Phe Asn Glu Thr Trp Glu Asn Tyr Lys Tyr Gly Phe Gly
65                  70                  75                  80

Arg Leu Asp Gly Glu Phe Trp Leu Gly Leu Glu Lys Ile Tyr Ser Ile
                85                  90                  95

Val Lys Gln Ser Asn Tyr Val Leu Arg Ile Glu Leu Glu Asp Trp Lys
            100                 105                 110

Asp Asn Lys His Tyr Ile Glu Tyr Ser Phe Tyr Leu Gly Asn His Glu
        115                 120                 125

```
Thr Asn Tyr Thr Leu His Leu Val Ala Ile Thr Gly Asn Val Pro Asn
        130                 135                 140

Ala Ile Pro Glu Asn Lys Asp Leu Val Phe Ser Thr Trp Asp His Lys
145                 150                 155                 160

Ala Lys Gly His Phe Asn Cys Pro Glu Gly Tyr Ser Gly Gly Trp Trp
                165                 170                 175

Trp His Asp Glu Cys Gly Glu Asn Asn Leu Asn Gly Lys Tyr Asn Lys
                180                 185                 190

Pro Arg Ala Ser Lys Pro Glu Arg Arg Gly Leu Ser Trp Lys Ser
                195                 200                 205

Gln Asn Gly Arg Leu Tyr Ser Ile Lys Ser Thr Lys Met Leu Ile His
210                 215                 220

Pro Thr Asp
225

<210> SEQ ID NO 41
<211> LENGTH: 222
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Glu Ile Arg Asn Val Lys His Asp Gly Ile Pro Ala Glu Cys Thr Thr
1               5                   10                  15

Ile Tyr Asn Arg Gly Glu His Thr Ser Gly Met Tyr Ala Ile Arg Pro
            20                  25                  30

Ser Asn Ser Gln Val Phe His Val Tyr Cys Asp Val Ile Ser Gly Ser
        35                  40                  45

Pro Trp Thr Leu Ile Gln His Arg Ile Asp Gly Ser Gln Asn Phe Asn
    50                  55                  60

Glu Thr Trp Glu Asn Tyr Lys Tyr Gly Phe Gly Arg Leu Asp Gly Glu
65                  70                  75                  80

Phe Trp Leu Gly Leu Glu Lys Ile Tyr Ser Ile Val Lys Gln Ser Asn
                85                  90                  95

Tyr Val Leu Arg Ile Glu Leu Glu Asp Trp Lys Asp Asn Lys His Tyr
            100                 105                 110

Ile Glu Tyr Ser Phe Tyr Leu Gly Asn His Glu Thr Asn Tyr Thr Leu
        115                 120                 125

His Leu Val Ala Ile Thr Gly Asn Val Pro Asn Ala Ile Pro Glu Asn
    130                 135                 140

Lys Asp Leu Val Phe Ser Thr Trp Asp His Lys Ala Lys Gly His Phe
145                 150                 155                 160

Asn Cys Pro Glu Gly Tyr Ser Gly Gly Trp Trp His Asp Glu Cys
                165                 170                 175

Gly Glu Asn Asn Leu Asn Gly Lys Tyr Asn Lys Pro Arg Ala Ser Lys
            180                 185                 190

Pro Glu Arg Arg Gly Leu Ser Trp Lys Ser Gln Asn Gly Arg Leu
        195                 200                 205

Tyr Ser Ile Lys Ser Thr Lys Met Leu Ile His Pro Thr Asp
    210                 215                 220

<210> SEQ ID NO 42
<211> LENGTH: 214
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 42

```
Gly Ile Pro Ala Glu Cys Thr Thr Ile Tyr Asn Arg Gly Glu His Thr
1               5                   10                  15

Ser Gly Met Tyr Ala Ile Arg Pro Ser Asn Ser Gln Val Phe His Val
            20                  25                  30

Tyr Cys Asp Val Ile Ser Gly Ser Pro Trp Thr Leu Ile Gln His Arg
        35                  40                  45

Ile Asp Gly Ser Gln Asn Phe Asn Glu Thr Trp Glu Asn Tyr Lys Tyr
    50                  55                  60

Gly Phe Gly Arg Leu Asp Gly Glu Phe Trp Leu Gly Leu Glu Lys Ile
65                  70                  75                  80

Tyr Ser Ile Val Lys Gln Ser Asn Tyr Val Leu Arg Ile Glu Leu Glu
                85                  90                  95

Asp Trp Lys Asp Asn Lys His Tyr Ile Glu Tyr Ser Phe Tyr Leu Gly
            100                 105                 110

Asn His Glu Thr Asn Tyr Thr Leu His Leu Val Ala Ile Thr Gly Asn
        115                 120                 125

Val Pro Asn Ala Ile Pro Glu Asn Lys Asp Leu Val Phe Ser Thr Trp
    130                 135                 140

Asp His Lys Ala Lys Gly His Phe Asn Cys Pro Glu Gly Tyr Ser Gly
145                 150                 155                 160

Gly Trp Trp Trp His Asp Glu Cys Gly Glu Asn Asn Leu Asn Gly Lys
                165                 170                 175

Tyr Asn Lys Pro Arg Ala Ser Lys Pro Glu Arg Arg Arg Gly Leu Ser
            180                 185                 190

Trp Lys Ser Gln Asn Gly Arg Leu Tyr Ser Ile Lys Ser Thr Lys Met
        195                 200                 205

Leu Ile His Pro Thr Asp
    210
```

<210> SEQ ID NO 43
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 43

```
Ile Pro Ala Glu Cys Thr Thr Ile Tyr Asn Arg Gly Glu His Thr Ser
1               5                   10                  15

Gly Met Tyr Ala Ile Arg Pro Ser Asn Ser Gln Val Phe His Val Tyr
            20                  25                  30

Cys Asp Val Ile Ser Gly Ser Pro Trp Thr Leu Ile Gln His Arg Ile
        35                  40                  45

Asp Gly Ser Gln Asn Phe Asn Glu Thr Trp Glu Asn Tyr Lys Tyr Gly
    50                  55                  60

Phe Gly Arg Leu Asp Gly Glu Phe Trp Leu Gly Leu Glu Lys Ile Tyr
65                  70                  75                  80

Ser Ile Val Lys Gln Ser Asn Tyr Val Leu Arg Ile Glu Leu Glu Asp
                85                  90                  95
```

-continued

```
Trp Lys Asp Asn Lys His Tyr Ile Glu Tyr Ser Phe Tyr Leu Gly Asn
                100             105             110

His Glu Thr Asn Tyr Thr Leu His Leu Val Ala Ile Thr Gly Asn Val
            115             120             125

Pro Asn Ala Ile Pro Glu Asn Lys Asp Leu Val Phe Ser Thr Trp Asp
    130             135             140

His Lys Ala Lys Gly His Phe Asn Cys Pro Glu Gly Tyr Ser Gly Gly
145             150             155             160

Trp Trp Trp His Asp Glu Cys Gly Glu Asn Asn Leu Asn Gly Lys Tyr
                165             170             175

Asn Lys Pro Arg Ala Ser Lys Pro Glu Arg Arg Arg Gly Leu Ser Trp
            180             185             190

Lys Ser Gln Asn Gly Arg Leu Tyr Ser Ile Lys Ser Thr Lys Met Leu
            195             200             205

Ile His Pro Thr Asp
    210

<210> SEQ ID NO 44
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 44

His His His His His His
1               5
```